US009315555B2

(12) United States Patent
Shone et al.

(10) Patent No.: US 9,315,555 B2
(45) Date of Patent: Apr. 19, 2016

(54) CLOSTRIDIUM DIFFICILE ANTIGENS

(71) Applicant: The Secretary of State for Health, London (GB)

(72) Inventors: Clifford Shone, Salisbury (GB); April Roberts, Salisbury (GB); Michael Maynard-Smith, Salisbury (GB)

(73) Assignee: The Secretary of State for Health, London (GB)

(*) Notice: Subject to any disclaimer, the term of this patent is extended or adjusted under 35 U.S.C. 154(b) by 0 days.

(21) Appl. No.: 14/390,528

(22) PCT Filed: Apr. 4, 2013

(86) PCT No.: PCT/GB2013/050886
§ 371 (c)(1),
(2) Date: Oct. 3, 2014

(87) PCT Pub. No.: WO2013/150309
PCT Pub. Date: Oct. 10, 2013

(65) Prior Publication Data
US 2015/0093389 A1 Apr. 2, 2015

(30) Foreign Application Priority Data

Apr. 4, 2012 (GB) .................................. 1206070.3

(51) Int. Cl.
| | | |
|---|---|---|
| *A61K 39/08* | (2006.01) | |
| *C07K 14/33* | (2006.01) | |
| *A61K 39/40* | (2006.01) | |
| *C07K 16/40* | (2006.01) | |
| *A61K 45/06* | (2006.01) | |
| *C12N 9/10* | (2006.01) | |
| *G01N 33/573* | (2006.01) | |
| *G01N 33/569* | (2006.01) | |
| *A61K 39/00* | (2006.01) | |

(52) U.S. Cl.
CPC ................ *C07K 14/33* (2013.01); *A61K 39/08* (2013.01); *A61K 39/40* (2013.01); *A61K 45/06* (2013.01); *C07K 16/40* (2013.01); *C12N 9/1051* (2013.01); *G01N 33/56911* (2013.01); *G01N 33/573* (2013.01); *A61K 2039/505* (2013.01); *A61K 2039/507* (2013.01); *A61K 2039/55566* (2013.01); *G01N 2333/91097* (2013.01); *G01N 2469/10* (2013.01); *G01N 2469/20* (2013.01)

(58) Field of Classification Search
CPC .............. A61K 39/08; A61K 2300/00; A61K 2039/505; A61K 2039/507; A61K 2039/53; A61K 31/4164; A61K 38/14; A61K 39/12; A61K 39/145; A61K 39/40; A61K 45/06; A61K 2039/55561; A61K 2039/55566
See application file for complete search history.

(56) References Cited

U.S. PATENT DOCUMENTS

| | | | |
|---|---|---|---|
| 5,601,823 | A | 2/1997 | Williams |
| 2005/0287150 | A1 | 12/2005 | Ambrosino |
| 2009/0311258 | A1 | 12/2009 | Von Eichelstreiber |
| 2011/0020845 | A1 | 1/2011 | Braun |

FOREIGN PATENT DOCUMENTS

| | | | |
|---|---|---|---|
| WO | 00/61762 | A1 | 10/2000 |
| WO | 01/94599 | A1 | 12/2001 |
| WO | 03/074555 | A2 | 9/2003 |
| WO | 2008/014733 | A1 | 2/2008 |
| WO | 2011/130650 | A2 | 10/2011 |
| WO | 2012/046061 | A2 | 4/2012 |

OTHER PUBLICATIONS

Genth H., et al., "New Method to Generate Enzymatically Deficient Clostridium difficile Toxin B as an Antigen for Immunization," Infection and Immunity 68(3):1094-1101, Mar. 2000.
Kink, J., and Williams, J., "Antibodies to Recombinant Clostridium difficile Toxins A and B are an Effective Treatment and Prevent Relapse of C. difficile-Associated Disease in a Hamster Model of Infection," Infection and Immunity 66(5): 2018-2025, May 1998.
Roberts, A., et al., "Development and Evaluation of an Ovine Antibody-Based Platform for Treatment of Clostridium difficile Infection," Infection and Immunity 80(2):875-882, Dec. 2011.
International Search Report mailed Jul. 19, 2013, issued in corresponding International Application No. PCT/GB2013/050886, filed Apr. 4, 2013, 5 pages.
Written Opinion mailed Mar. 19, 2014, issued in corresponding International Application No. PCT/GB2013/050886, filed Apr. 4, 2013, 8 pages.
International Preliminary Report on Patentability mailed Jun. 25, 2014, issued in corresponding International Application No. PCT/GB2013/050886, filed Apr. 4, 2013, 18 pages.
UniProt entry Q183K2, Entry name: Q183K2_PEPD6 (Peptoclostridium difficile, strain 630), Jul. 25, 2006, <http://www.uniprot.org/uniprot/Q183K2> [retrieved Jun. 22, 2015], 6 pages.

*Primary Examiner* — Padma V Baskar
(74) *Attorney, Agent, or Firm* — Christensen O'Connor Johnson Kindness PLLC

(57) ABSTRACT

The present invention relates to recombinant *Clostridium difficile* antigens based on a polypeptide, consisting of or comprising an amino acid sequence having at least 80% sequence identity with an amino acid sequence consisting of residues 1500-700 of a *C. difficile* Toxin A sequence or a *C. difficile* Toxin B sequence; though with the proviso that the polypeptide does not include one or more Repeat Unit (RU) located between amino acid residues 1851-2710 of *C. difficile* Toxin A and/or residues 1853-2366 of a *C. difficile* Toxin B protein that consists of or comprises a first amino acid sequence and a second amino acid. Also provided is the use of said antigens for the prevention/treatment/suppression of *Clostridium difficile* infection (CDI), together with methods for generating said antigens, methods for generating antibodies that bind to said antigens, and the use of said antibodies for the prevention/treatment/suppression of CDI.

12 Claims, 6 Drawing Sheets

Figure 1 - illustrates the structures of *C. difficile* Toxins A and B showing amino acid residues at the various domain boundaries.
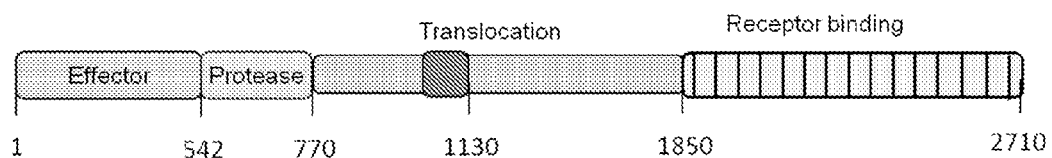
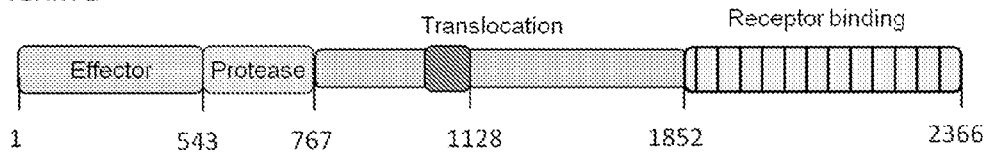

Figure 2 - SDS-PAGE analysis of the nickel affinity purification of the His$_6$TrxTxBcentral from bacterial cell lysate. M = molecular weight markers; sup = protein not precipitated by ammonium sulphate, pptL = precipitate from ammonium sulphate step subsequently loaded onto nickel column. FT = column flow through. Fractions A11 to C8 represent the eluted protein.

Figure 3 - SDS-PAGE and Western blot analysis of purified TxACDP constructs (based on residues 542-1850 of Toxin A). The left hand panel shows the SDS-PAGE; right hand panel Western blot using ovine anti-Toxin A antibody.

Figure 4. Expression and purification of CD2767 (residues 27-401). Purification of CD2767 (residues 27-401) by immobilised metal ion affinity chromatography. Key: column load, L; flow through fraction, FT; eluted purified CD2767 polypeptide, E1. The intense band of the CD2767 polypeptide is illustrative of its high solubility.
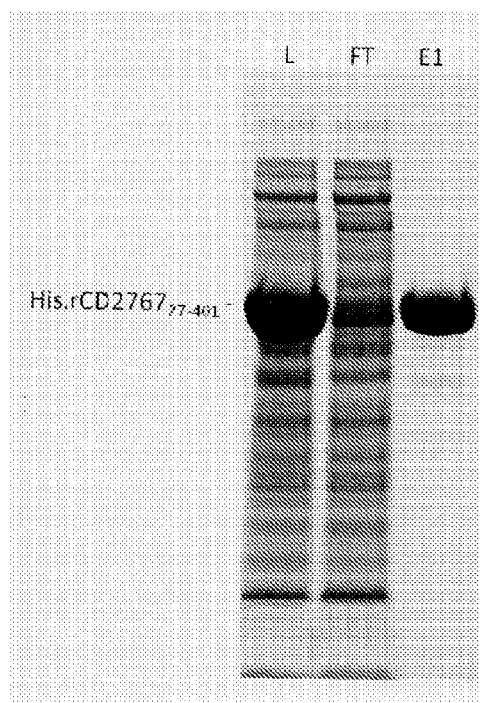

Figure 5. Expression and purification of a fusion protein consisting of CD2767 (residues 27-401) with Toxin A (residues 543-1851). The fusion protein was expressed as a soluble polypeptide (top band in lanes C1 and C2) at approximately 2% of the total protein. C1 and C2 represent duplicate of the soluble fraction of the total expressed protein.

Figure 6. Antibody-mediated neutralisation of Toxin A and Toxin B as measured by the Vero cell $ED_{50}$ assay. The capacity of various dilutions of antiserum to Toxin A (residues 543-1851) (●) to prevent the cytotoxic effects of purified Toxin A (50 ng/ml) was assessed using crystal violet staining to measure cell viability. Reduced absorbance indicates a lack of cell integrity. Neutralisation by Toxin B (residues 767-1852) antiserum (▼) was assessed using Toxin B at 2ng/ml. Each antiserum was a pool obtained from the immunisation of 3 sheep.

CLOSTRIDIUM DIFFICILE ANTIGENS

CROSS-REFERENCE TO RELATED APPLICATION

This application is the National Stage of International Application No. PCT/GB2013/050886, filed Apr. 4, 2013, the disclosure of which is incorporated by reference herein.

STATEMENT REGARDING SEQUENCE LISTING

The sequence listing associated with this application is provided in text format in lieu of a paper copy and is hereby incorporated by reference into the specification. The name of the text file containing the sequence listing is SQL ST25.txt. The text file is 243 KB; was created on Sep. 26, 2014 and is being submitted via EFS-Web with the filing of the specification.

BACKGROUND

The present invention relates to antigens for the prevention/treatment/suppression of *Clostridium difficile* infection (CDI). Also provided are methods for generating said antigens, methods for generating antibodies that bind to said antigens, and the use of said antibodies for the prevention/treatment/suppression of CDI.

*Clostridium difficile* infection (CDI) is now a major problem in hospitals worldwide. The bacterium causes nosocomial, antibiotic-associated disease which manifests itself in several forms ranging from mild self-limiting diarrhoea to potentially life-threatening, severe colitis. Elderly patients are most at risk from these potentially life-threatening diseases and incidents of CDI have increased dramatically over the last 10 years. In 2010 in the UK there were over 21,000 cases of CDI with over 2,700 associated deaths. CDI costs the UK National Health Service in excess of £500M per annum.

The various strains of *C. difficile* may be classified by a number of methods. One of the most commonly used is polymerase chain reaction (PCR) ribotyping in which PCR is used to amplify the 16S-23S rRNA gene intergenic spacer region of *C. difficile*. Reaction products from this provide characteristic band patterns identifying the bacterial ribotype of isolates. Toxinotyping is another typing method in which the restriction patterns derived from DNA coding for the *C. difficile* toxins are used to identify strain toxinotype. The differences in restriction patterns observed between toxin genes of different strains are also indicative of sequence variation within the *C. difficile* toxin family. For example, there is an approximate 13% sequence difference with the C-terminal 60 kDa region of toxinotype 0 Toxin B compared to the same region in toxinotype III Toxin B.

Strains of *C. difficile* produce a variety of virulence factors, notable among which are several protein toxins: Toxin A, Toxin B and, in some strains, a binary toxin which is similar to *Clostridium perfringens* iota toxin. Toxin A is a large protein cytotoxin/enterotoxin which plays a role in the pathology of infection and may influence the gut colonisation process. Outbreaks of CDI have been reported with Toxin A-negative/Toxin B-positive strains, which indicates that Toxin B is also capable of playing a key role in the disease pathology.

The genetic sequences encoding Toxin A and Toxin B (Mw 308k and Mw 269k, respectively) are known—see, for example, Moncrief et al. (1997) Infect. Immun. 63:1105-1108. The two toxins have high sequence homology and are believed to have arisen from gene duplication. The toxins also share a common structure (see FIG. 1), namely an N-terminal glucosyl transferase domain, a central hydrophobic region, four conserved cysteines, and a long series of C-terminal repeating units (RUs).

Both Toxins A and B exert their mechanisms of action via multi-step mechanisms, which include binding to receptors on the cell surface, internalisation followed by translocation and release of the effector domain into the cell cytosol, and finally intracellular action. Said mechanism of action involves the inactivation of small GTPases of the Rho family. In this regard, the toxins catalyse the transfer of a glucose moiety (from UDP-glucose) onto an amino residue of the Rho protein. Toxins A and B also contain a second enzyme activity in the form of a cysteine protease, which appears to play a role in the release of the effector domain into the cytosol after translocation. The *C. difficile* binary toxin modifies cell actin by a mechanism which involves the transfer of an ADP-ribose moiety from NAD onto its target protein.

Current therapies for the treatment of *C. difficile* infection rely on the use of antibiotics, notably metronidazole and vancomycin. However, these antibiotics are not effective in all cases and 20-30% of patients suffer relapse of the disease. Of major concern is the appearance in the UK of more virulent strains, which were first identified in Canada in 2002. These strains, which include those belonging to PCR ribotype 027 and toxinotype III, cause CDI with a directly attributable mortality more than 3-fold that observed previously.

New therapeutics are therefore required especially urgently since the efficacy of current antibiotics appears to be decreasing.

One approach is the use of antibodies which bind to and neutralise the activity of Toxin A and/or Toxin B. This is based on the knowledge that strains of *C. difficile* that do not release these toxins, so called non-toxigenic strains, do not cause CDI. By way of example, animals can be immunised, their sera collected and the antibodies purified for administration to patients—this is defined as passive immunisation. In another approach patients with CDI or subjects at risk of developing such infections can be immunised with antigens which result in an increase in circulating and mucosal antibodies directed against Toxin A and/or Toxin B—this is defined as active immunisation.

A critical requirement for both active and passive immunisation is the availability of suitable antigens with which to immunise the patient or animal respectively. These can comprise the natural toxins which can be purified from the media in which suitable toxigenic strains of *C. difficile* have been cultured. There are several disadvantages to this approach. Both Toxin A and Toxin B are present in culture medium in only small amounts and are difficult to purify without incurring significant losses. Thus, it is both costly and difficult to obtain the amounts necessary to meet world-wide needs. In addition, the natural toxins are unstable and toxic.

The above mentioned problems have resulted in there being few available *C. difficile* vaccine candidates. To date, the only CDI vaccine in late-stage development is based on a mixture of native (i.e. naturally occurring) Toxins A and B, which have been extensively inactivated by chemical modification (Salnikova et al. 2008, J. Pharm. Sci. 97:3735-3752).

One alternative to the use of natural toxins (and their toxoids) involves the design, development and use of recombinant fragments derived from Toxins A and B. Examples of existing antigens intended for use in treating/preventing a *C. difficile* infection include peptides based on the C-terminal repeating units (RUs) of Toxin A or Toxin B—see, for example, WO 00/61762. A problem with such antigens, however, is that they are either poorly immunogenic (i.e. the antigens produce poor antibody titres), or, where higher antibody titres are produced, the antibodies demonstrate poor neutralising efficacy against *C. difficile* cytotoxic activity (i.e. insufficient neutralising antibodies are produced).

There is therefore a need in the art for new vaccines/therapies/therapeutics capable of specifically addressing *C. difficile* infection (CDI). This need is addressed by the present invention, which solves one or more of the above-mentioned problems.

SUMMARY OF THE INVENTION

In summary, the present invention provides antigens that are able to induce a potent toxin-neutralising response against *C. difficile* Toxin A and/or Toxin B. The invention also provides methods for preparing recombinant antigens, and the use thereof as immunogens to enable the large-scale preparation of therapeutic antibodies. Said antibodies are able to induce a potent toxin-neutralising response against *C. difficile* Toxin A and/or Toxin B and therefore have prophylactic and/or therapeutic applications.

As mentioned above (see, for example, WO 00/61762), previous studies describe vaccine preparations based on the C-terminal, repeating units (RUs) of Toxin A and/or Toxin B. Said RU fragments have a poor toxin-neutralising effect, and/or are difficult to manufacture in large quantities.

In contrast, the present invention provides a *C. difficile* polypeptide antigen based on a Toxin A and/or a Toxin B that does not contain or include one or more (e.g. all) of the repeating units (RUs) of Toxin A and/or Toxin B. The polypeptide antigens of the invention consist of, or comprise one or more domains from the central region of the toxins. Said antigens of the invention demonstrate good toxin-neutralising immune responses and/or are readily manufactured in large quantities.

The present inventors have surprisingly identified that *C. difficile* antigen polypeptides which consist of or comprise one or more domains from the central region between the effector domain and the region of RUs (see FIG. 1) provide a protective (toxin-neutralising) immune response that was greatly enhanced as compared to corresponding *C. difficile* toxin fragments comprising one or more of the RUs (see Tables 1 and 2).

Comparison of the data in Tables 1 and 2 confirms that the polypeptide antigens of the present invention elicit a considerably more potent toxin-neutralising immune response than that of a corresponding polypeptide based that includes one or more of the C-terminal repeating units of *C. difficile* toxin (exemplified by the polypeptide designated TxB2). In more detail, after a 18-week immunisation period, the toxin-neutralising immune response provided by polypeptides of the present invention was more than 60-fold higher than that provided by a corresponding RU-containing polypeptide. Thus, polypeptides of the present invention induce a potent toxin-neutralising immune response.

These findings are surprising for a number of reasons. Most importantly, a previous study in which animals were separately immunised with central domain fragments of *C. difficile* toxin (a fragment consisting of residues 510-1530, and a fragment consisting of residues 1530-1750) reported that these fragments failed to elicit the production of toxin-neutralising antibodies (Kink and Williams (1993) Infect. Immun. 66:2018-2025). This study therefore suggests that domains within residues 510-1530 contribute no significant antibody-binding structural determinants. In addition, a further study has showed that antibodies raised against a whole *C. difficile*, while recognising a fragment consisting of the entire RU region alone, failed to recognise a fragment consisting of a central toxin region based on residues 901-1750 of the *C. difficile* same toxin (Genth et al., (2000) Infect. Immun., 68:1094-1101). This study therefore suggests that domains within residues 901-1750 contribute no significant antibody-binding structural determinants. Furthermore, while antibodies to the effector domain (residues 1-543) of *C. difficile* toxin have been shown to elicit a potent immune response (measured by simple enzyme immunoassay), said antibodies have no toxin-neutralising activity showing that antibody binding to the toxin does not correspond to toxin neutralisation (Roberts et al. (2012) Infect. Immun., 80:875-882). Collectively, it is therefore extremely surprising that recombinant immunogens based on the central domains of the *C. difficile* toxins located between the effector domain and repeat regions are capable of inducing such a potent toxin-neutralising immune response.

One aspect of the present invention provides a polypeptide containing, consisting of, or comprising an amino acid sequence that has at least 80% sequence identity with an amino acid sequence consisting of residues 1500-1800 (e.g. 1450-1750, or 1400-1800) of a *C. difficile* Toxin A sequence with the proviso that the polypeptide is not a polypeptide comprising one or more of (e.g. all of) the RU units between amino acid residues 1851-2710 of *C. difficile* Toxin A and/or residues 1853-2366 of a *C. difficile* Toxin B. In one embodiment, said polypeptide lacks the sequence of amino acid residues 1851-2710 of *C. difficile* Toxin A and/or residues 1853-2366 of a *C. difficile* Toxin B.

Another aspect of the present invention provides a polypeptide containing, consisting of or comprising an amino acid sequence that has at least 80% sequence identity with an amino acid sequence consisting of residues 542-1850 of a *C. difficile* Toxin A sequence with the proviso that the polypeptide does not comprise any of the RU units between residues 1851-2710 of *C. difficile* Toxin A or residues 1853-2366 of a *C. difficile* Toxin B. In one embodiment, said polypeptide lacks the sequence of amino acid residues 1851-2710 of *C. difficile* Toxin A and/or residues 1853-2366 of a *C. difficile* Toxin B.

Reference to a *C. difficile* Toxin A sequence means the amino acid sequence of a naturally-occurring *C. difficile* Toxin A (also referred to as a *C. difficile* Toxin A reference sequence). Examples of such sequences are readily understood by a skilled person, and simply for illustrative purposes, some of the more common naturally-occurring Toxin A sequences are identified in the present specification (see, for example, SEQ ID NOs: 1 and 3) as well as throughout the literature.

Reference to 'at least 80% sequence identity' throughout this specification is considered synonymous with the phrase 'based on' and may embrace one or more of at least 85%, at least 90%, at least 93%, at least 95%, at least 97%, at least 99%, and 100% sequence identity. When assessing sequence identity, a reference sequence having a defined number of contiguous amino acid residues is aligned with an amino acid sequence (having the same number of contiguous amino acid residues) from the corresponding portion of a polypeptide of the present invention.

In one embodiment, the polypeptide amino acid sequence is based on (i.e. has at least 80% sequence identity with) amino acid residues 1500-1700 or amino acid residues 1450-1750, or amino acid residues 1400-1800 of a *C. difficile* Toxin A. In another embodiment, the polypeptide amino acid sequence is based on amino acid residues 544-1850 of a *C. difficile* Toxin A, such as amino acid residues 564-1850, amino acid residues 584-1850, amino acid residues 594-1850, amino acid residues 614-1850, amino acid residues 634-1850, amino acid residues 654-1850, amino acid residues 674-1850, amino acid residues 694-1850, amino acid residues 714-1850, amino acid residues 734-1850, amino acid residues 754-1850, amino acid residues 767-1850, amino acid residues 770-1850, amino acid residues 774-1850, amino acid residues 794-1850, amino acid residues 814-1850, amino acid residues 834-1850, amino acid residues 854-1850, amino acid residues 874-1850, amino acid residues 894-1850, amino acid residues 914-1850, amino acid residues 934-1850, amino acid residues 954-1850, amino acid residues 974-1850, amino acid residues 994-1850, amino acid residues 1014-1850, amino acid residues 1034-1850, amino acid residues 1054-1850, amino acid residues 1074-1850, amino acid residues 1094-1850, amino acid residues 1104-1850, amino acid residues 1124-1850, amino acid residues, amino acid residues 1131-1850, amino acid residues 1144-1850, amino acid residues 1164-1850, amino acid residues 1184-1850, amino acid residues 1204-1850, amino acid residues 1224-1850, amino acid residues 1244-1850, amino acid residues 1264-1850, amino acid residues 1284-1850, amino acid residues 1304-1850, amino acid residues 1324-1850, amino acid residues 1344-1850, amino acid residues 1450-1750 or amino acid residues 1550-1850; though with the proviso that the polypeptide does not include one or more of (e.g. all of) the RU units between residues 1851-2710 of *C. difficile* Toxin A or residues 1853-2366 of a *C. difficile* Toxin B. In one embodiment, said polypeptide lacks the sequence of amino acid residues 1851-2710 of *C. difficile* Toxin A and/or residues 1853-2366 of a *C. difficile* Toxin B. By way of example only, the above amino acid position numbering may refer to the *C. difficile* Toxin A sequences identified as SEQ ID NOs: 1 and/or 3.

In one embodiment a polypeptide is provided, which comprises or consists of a sequence based on amino acid residues 542-1850 of a Toxin A sequence (or a portion thereof). Examples are identified as a polypeptide comprising or consisting of the amino acid sequence SEQ ID NOs: 5 and 6.

In another embodiment a polypeptide is provided, which comprises or consists of a sequence based on amino acid residues 542-1850 of a Toxin A sequence (or a portion thereof) that substantially lacks cysteine protease activity. An example is identified as a polypeptide comprising or consisting of the amino acid sequence SEQ ID NO: 7.

In another embodiment a polypeptide is provided, which comprises or consists of a sequence based on amino acid residues 770-1850 of a Toxin A sequence (or a portion thereof). An example is identified as a polypeptide comprising or consisting of the amino acid sequence SEQ ID NO: 8.

In another embodiment a polypeptide is provided, which comprises or consists of a sequence based on amino acid residues 1130-1850 of a Toxin A sequence (or a portion thereof). An example is identified as a polypeptide comprising or consisting of the amino acid sequence SEQ ID NO: 9.

A related aspect of the present invention provides a polypeptide containing, consisting of, or comprising an amino acid sequence that has at least 80% sequence identity with an amino acid sequence consisting of residues 1500-1700 (e.g. 1450-1750, or 1400-1800) of a *C. difficile* Toxin B sequence with the proviso that the polypeptide does comprise one or more of (e.g. any of) the RU units between residues 1851-2710 of *C. difficile* Toxin A or residues 1853-2366 of a *C. difficile* Toxin B. In one embodiment, said polypeptide lacks the sequence of amino acid residues 1851-2710 of *C. difficile* Toxin A and/or residues 1853-2366 of a *C. difficile* Toxin B.

In another aspect of the present invention provides a polypeptide containing, consisting of, or comprising an amino acid sequence that has at least 80% sequence identity with an amino acid sequence consisting of residues 543-1852 of a *C. difficile* Toxin B sequence with the proviso that the polypeptide does not comprise one or more of (e.g. any of) the RU units between residues 1851-2710 of *C. difficile* Toxin A or residues 1853-2366 of a *C. difficile* Toxin B. In one embodiment, said polypeptide lacks the sequence of amino acid residues 1851-2710 of *C. difficile* Toxin A and/or residues 1853-2366 of a *C. difficile* Toxin B.

Reference to a *C. difficile* Toxin B sequence means the amino acid sequence of a naturally-occurring *C. difficile* Toxin B (also referred to as a *C. difficile* Toxin B reference sequence). Examples of such sequences are readily understood by a skilled person, and simply for illustrative purposes some of the more common naturally-occurring Toxin B sequences are identified in the present specification (see, for example, SEQ ID NOs: 2 and 4) as well as throughout the literature.

In one embodiment, the polypeptide amino acid sequence is based on (i.e. has at least 80% sequence identity with) amino acid residues 1500-1700 or amino acid residues 1450-1750, or amino acid residues 1400-1800 of a *C. difficile* Toxin B. In another embodiment, the polypeptide amino acid sequence is based on amino acid residues 544-1852 of a *C. difficile* Toxin B, such as amino acid residues 564-1852, amino acid residues 584-1852, amino acid residues 594-1852, amino acid residues 614-1852, amino acid residues 634-1852, amino acid residues 654-1852, amino acid residues 674-1852, amino acid residues 694-1852, amino acid residues 714-1852, amino acid residues 734-1852, amino acid residues 754-1852, amino acid residues 767-1852, amino acid residues 770-1852, amino acid residues 774-1852, amino acid residues 794-1852, amino acid residues 814-1852, amino acid residues 834-1852, amino acid residues 854-1852, amino acid residues 874-1852, amino acid residues 894-1852, amino acid residues 914-1852, amino acid residues 934-1852, amino acid residues 954-1852, amino acid residues 974-1852, amino acid residues 994-1852, amino acid residues 1014-1852, amino acid residues 1034-1852, amino acid residues 1054-1852, amino acid residues 1074-1852, amino acid residues 1094-1852, amino acid residues 1104-1852, amino acid residues 1124-1852, amino acid residues 1131-1852, amino acid residues 1144-1852, amino acid residues 1164-1852, amino acid residues 1184-1852, amino acid residues 1204-1852, amino acid residues 1224-1852, amino acid residues 1244-1852, amino acid residues 1264-1852, amino acid residues 1284-1852, amino acid residues 1304-1852, amino acid residues 1324-1852, amino acid residues 1344-1852, amino acid residues 1450-1750 or amino acid residues 1550-1800, amino acid residues 1450-1750 or amino acid residues 1550-1850; though with the proviso that the polypeptide does not include one or more of (e.g. all of) the RU units between residues 1851-2710 of *C. difficile* Toxin A or residues 1853-2366 of a *C. difficile* Toxin B. In one embodiment, said polypeptide lacks the sequence of amino acid residues 1851-2710 of *C. difficile* Toxin A and/or residues 1853-2366 of a *C. difficile* Toxin B. By way of example only, the above amino acid position numbering may refer to the *C. difficile* Toxin B sequences identified as SEQ ID NOs: 2 and/or 4.

In one embodiment a polypeptide is provided, which comprises or consists of a sequence based on amino acid residues 543-1852 of a Toxin B sequence (or a portion thereof). Examples are identified as a polypeptide comprising or consisting of the amino acid sequence SEQ ID NOs: 10 or 11.

In another embodiment a polypeptide is provided, which comprises or consists of a sequence based on amino acid residues 543-1852 of a Toxin B sequence (or a portion thereof) that substantially lacks cysteine protease activity. An example is identified as a polypeptide comprising or consisting of the amino acid sequence SEQ ID NO: 12.

In another embodiment a polypeptide is provided, which comprises or consists of a sequence based on amino acid residues 767-1852 of a Toxin B sequence (or a portion thereof). An example is identified as a polypeptide comprising or consisting of the amino acid sequence SEQ ID NO: 13.

In another embodiment a polypeptide is provided, which comprises or consists of a sequence based on amino acid residues 1145-1852 of a Toxin B sequence (or a portion thereof). An example is identified as a polypeptide comprising or consisting of the amino acid sequence SEQ ID NO: 14.

In another embodiment a polypeptide is provided, which comprises or consists of a sequence based on amino acid residues 1350-1852 of a Toxin B sequence (or a portion thereof). An example is identified as a polypeptide comprising or consisting of the amino acid sequence SEQ ID NO: 15.

The antigen polypeptides of the invention may substantially lack cysteine protease activity. In another (or the same) embodiment, antigens substantially lack glucosyl transferase activity. For example, amino acid sequence(s) providing said activity (activities) may be absent (e.g. deleted) from the antigens of the present invention. Alternatively, key amino acid residues essential for providing such activities may be either modified or deleted. Examples of amino acid modifications to substantially reduce the cysteine protease activity of Toxin A are cysteine 700 to alanine, histidine 655 to alanine, aspartic acid 589 to asparagine or a combination of more than one of these mutations. Examples of amino acid modifications to substantially reduce the cysteine protease activity of Toxin B are cysteine 698 to alanine, histidine 653 to alanine, aspartic acid 587 to asparagine or a combination of more than one of these mutations. Examples of amino acid modifications to substantially reduce the glucosyl transferase activity of Toxin A are aspartic acid 285 to alanine, aspartic acid 287 to alanine or a combination of both mutations. Examples of amino acid modifications to substantially reduce the glucosyl transferase activity of Toxin B are aspartic acid 286 to alanine, aspartic acid 288 to alanine or a combination of both mutations. These enzymatic activities are present in native Toxin A and/or Toxin B, and are associated with N-terminal domains of said Toxins (see FIG. 1, and/or SEQ ID NOs: 1, 2, 3 and 4).

The antigen polypeptides of the invention may substantially lack the glucosyl transferase domain (amino acid residues 1-542 Toxin A; amino acid residues 1-543 Toxin B) of a native C. difficile Toxin. In another (or the same) embodiment, the antigen substantially lacks the cysteine protease domain (amino acid residues 543-770 Toxin A; 544-767 Toxin B) of a native C. difficile Toxin. Said amino acid residue numbering refers to any Toxin A or Toxin B toxinotype, for example any one or more of the reference Toxin A and/or Toxin B toxinotype SEQ ID NOs recited in the present specification. Accordingly, said amino acid residue numbering may refer to any specific Toxin A and/or Toxin B reference SEQ ID NO recited in the present specification including an amino acid sequence variant having at least 80%, at least 85%, at least 90%, at least 93%, at least 95%, at least 97%, or at least 99% thereto.

Antigen polypeptides of the invention include chimeras in which one portion of the antigen is derived from the central domain(s) of Toxin A and/or Toxin B and a second portion of the antigen is based on a domain of a bacterial surface layer protein component (SLP) of C. difficile (or a fragment thereof). Inclusion of said domain has been identified by the present inventors to confer several advantages. Such SLP domains facilitate the soluble expression of antigen polypeptides of the invention. In addition, since these SLP domains are of C. difficile origin, it is unnecessary to cleave and remove them from constructs prior to immunisation. Indeed, the present inventors believe that antibodies to such domains recognise the intact C. difficile bacterium and afford additional therapeutic benefits by preventing or slowing the process of bacterial colonisation. An example of such a C. difficile SLP domain is based on a polypeptide comprising or consisting of the polypeptide product from C. difficile gene CD2767 (or a fragment thereof). By way of specific example, reference is made to a polypeptide fragment based on amino acid residues 27-401 of the polypeptide product of C. difficile gene CD2767 (or a portion thereof)—see, for example, a polypeptide consisting of or comprising the amino acid sequence SEQ ID NO: 16. Such a domain may be, for example, positioned at the N-terminus and/or C-terminus of a polypeptide of the invention.

For example, in one embodiment of the invention, a polypeptide antigen is provided which consists of or comprises a CD2767 polypeptide (e.g. based on residues 27-401 thereof) and a C. difficile toxin polypeptide (e.g. a central domain) as hereinbefore defined.

In another embodiment a polypeptide antigen is provided which consists of or comprises a CD2767 polypeptide (e.g. based on residues 27-401 thereof) and a C. difficile toxin polypeptide based on an amino acid sequence consisting of or comprising amino acid residues 770-1850 of a Toxin A sequence (or a portion thereof).

In another embodiment a polypeptide antigen is provided which consists of or comprises a CD2767 polypeptide (e.g. based on residues 27-401 thereof) and a C. difficile toxin polypeptide based on an amino acid sequence consisting of or comprising amino acid residues 542-1850 of a Toxin A sequence (or a portion thereof). An example is identified as a polypeptide comprising or consisting of the amino acid sequence SEQ ID NO: 17.

In a related embodiment of the invention and antigen is provided which consists of a chimera of CD2767 polypeptide residues 27-401 (or a portion thereof) with amino acid residues 767-1852 of a Toxin B sequence (or a portion thereof). See SEQ ID NO: 18.

In another embodiment of the invention a polypeptide antigen is provided which consists of or comprises a CD2767 polypeptide (e.g. based on residues 27-401 thereof) and a C. difficile toxin polypeptide based on an amino acid sequence consisting of or comprising amino acid residues 543-1852 of a Toxin B sequence (or a portion thereof).

Antigen polypeptides of the invention may additionally (or alternatively) to an SPL comprise other fusion protein partners to facilitate soluble expression. Fusion protein partners may be attached at the N- or C-terminus of the antigen construct but are usually placed at the N-terminal end. Examples of fusion partners are: NusA, thioredoxin, maltose-binding protein, small ubiquitin-like molecules (Sumo-tag). To facilitate removal of the fusion protein partner during purification, a unique protease site may be inserted between the fusion protein partner and the fusion protein per se. Such protease sites may include those for thrombin, factor Xa, enterokinase, PreScission™, Sumo™. Alternatively, removal of the fusion protein partner may be achieved via inclusion of an intein sequence between the fusion protein partner and the fusion protein per se. Inteins are self cleaving proteins and in response to a stimulus (e.g. lowered pH) are capable of self splicing at the junction between the intein and the antigen construct thus eliminating the need for the addition of specific proteases. Examples of inteins include domains derived from *Mycobacterium tuberculosis* (RecA), and *Pyrococcus horikoshii* (RadA) (Fong et al. (2010) Trends Biotechnol. 28:272-279).

To facilitate purification, antigens of the invention may include one or more purification tags to enable specific chromatography steps (e.g. metal ion chelating, affinity chromatography) to be included in the purification processes. Such purification tags may, for example, include: repeat histidine residues (e.g. 6-10 histidine residues), maltose binding protein, glutathione S-transferase; and streptavidin. These tags may be attached at the N- and/or C-terminus of the polypeptide antigens of the invention. To facilitate removal of such tags during purification, protease sites and/or inteins (examples above) may be inserted between the polypeptide and the purification tag(s). Examples of expression constructs for Toxin A and Toxin B derived antigens of the invention are shown in SEQ ID NOs: 17, 18, 19 and 20.

Thus, a typical antigen construct of the invention (starting from the N-terminus) may comprise:
 a first purification tag
 an optional fusion protein partner (to facilitate expression) and/or an optional SLP
 a first (preferably specific) protease sequence or intein sequence
 the Toxin A and/or Toxin B antigen sequence
 an optional second (preferably specific) protease sequence or intein sequence
 an optional second purification tag The first and second purification tags may be the same or different. Similarly, the first and second protease/intein sequence may be the same or different. The first and second options are preferably different to enable selective and controllable cleavage/purification.

In one embodiment, the antigen of the invention is a chimera and consists of a portion or domain of a *C. difficile* surface protein in conjunction with a toxin antigen sequence based on the central domain(s) Toxins A and/or Toxin B.

Accordingly, in one embodiment, a polypeptide of the invention may comprise (starting from the N-terminus):
 a first purification tag
 a first (preferably specific) protease sequence or intein sequence
 an antigen sequence which is a chimera of Toxin A or Toxin B and an SLP
 an optional second (preferably specific) protease sequence or intein sequence
 an optional second purification tag Spacers may be introduced to distance the purification tag from the polypeptide—this may help to increase binding efficiency to affinity purification column media. The spacer may be placed (immediately) after the purification tag or between the fusion protein partner component and the remainder of the polypeptide per se. Similarly, spacers may be employed to distance the fusion protein partner and/or SLP from the *C. difficile* toxin component. Typical spacer sequences may consist of between 10-40 amino acid residues to give either a linear or alpha-helical structure.

Accordingly, in one embodiment, a polypeptide of the invention may comprise (starting from the N-terminus):
 a first purification tag
 an optional first spacer sequence
 a fusion protein partner (to facilitate expression) and/or an SLP
 an optional second spacer sequence
 a (preferably specific) protease sequence or intein sequence
 the Toxin A and/or Toxin B derived antigen sequence
 an optional second (preferably specific) protease sequence or intein sequence
 an optional third spacer sequence
 an optional second purification tag Genes encoding the constructs of the invention may be generated by PCR from *C. difficile* genomic DNA and sequenced by standard methods to ensure integrity. Alternatively and preferably genes may be synthesised providing the optimal codon bias for the expression host (e.g. *E. coli, Bacillus megaterium*). Thus, the present invention provides corresponding nucleic acid sequences that encode the aforementioned polypeptides of the present invention.

Accordingly, a second aspect of the present invention provides a method for expressing one or more of the aforementioned polypeptide antigens of the invention, said method comprising:
 1) providing a nucleic acid sequence that encodes one or more of said polypeptide antigens in a host cell, wherein said nucleic acid sequence is operably linked to a promoter; and
 2) expressing said nucleic acid sequence in the host cell.

Antigen polypeptides of the invention may be formulated as vaccines for human or animal use in a number of ways. For example, formulation may include treatment with an agent to introduce intra-molecular cross-links. One example of such an agent is formaldehyde, which may be incubated, for example, with antigen polypeptides of the invention for between 1-24 hours. Alternatively, longer incubation times of, for example, up to 2, 4, 6, 8 or 10 days may be employed. Following treatment with such an agent, antigens of the invention may be combined with a suitable adjuvant, which may differ depending on whether the antigen is intended for human or animal use.

A human or animal vaccine formulation may contain polypeptides of the present invention. Thus, in one embodiment, a vaccine formulation procedure of the present invention comprises the following steps:
 providing a recombinant polypeptide of the invention in suitable buffer system
 optionally (preferably) treating said mixture with a toxoiding component such as formaldehyde
 optionally transferring the polypeptide to a new buffer system
 combining the polypeptide with one or more suitable adjuvants and optionally other excipients.

Accordingly, a third aspect of the present invention provides one or more of the aforementioned polypeptides of the invention, for use in the generation of antibodies that bind to *C. difficile* Toxin A and/or Toxin B. In one embodiment, said antibodies bind to and neutralise *C. difficile* Toxin A and/or Toxin B.

For immunisation of animals, the *C. difficile* recombinant antigen polypeptides of the invention may be used as immunogens separately or in combination, either concurrently or sequentially, in order to produce antibodies specific for individual *C. difficile* toxins or combinations. For example, two or more recombinant antigens may be mixed together and used as a single immunogen. Alternatively a *C. difficile* toxin antigen (e.g. Toxin A-derived) may be used separately as a first immunogen on a first animal group, and another *C. difficile* toxin antigen (e.g. Toxin B-derived) may be used separately on a second animal group. The antibodies produced by separate immunisation may be combined to yield an antibody composition directed against *C. difficile* toxins. Non-limiting examples of suitable adjuvants for animal/veterinary use include Freund's (complete and incomplete forms), alum (aluminium phosphate or aluminium hydroxide), saponin and its purified component Quil A.

A fourth (vaccine) aspect of the present invention provides one or more of the aforementioned polypeptide antigens of the invention, for use in the prevention, treatment or suppression of CDI (e.g. in a mammal such as man). Put another way, the present invention provides a method for the prevention, treatment or suppression of CDI (e.g. in a mammal such as man), said method comprising administration of a therapeutically effective amount of one or more of the aforementioned polypeptides of the invention to a subject (e.g. a mammal such as man).

By way of example, a Toxin A-based antigen (any A toxinotype) may be employed alone or in combination with a Toxin B-based antigen (any B toxinotype). Similarly, a Toxin B-based antigen (any B toxinotype) may be employed alone or in combination with a Toxin A-based antigen (any A toxinotype). Said antigens may be administered in a sequential or simultaneous manner. Vaccine applications of the present invention may further include the combined use (e.g. prior, sequential or subsequent administration) of one or more antigens such as a *C. difficile* antigen (e.g. a non-Toxin antigen; or a *C. difficile* bacterium such as one that has been inactivated or attenuated), and optionally one or more nosocomial infection antigens (e.g. an antigen, notably a surface antigen, from a bacterium that causes nosocomial infection; and/or a bacterium that causes a nosocomial infection such as one that has been inactivated or attenuated). Examples of bacteria that cause nosocomial infection include one or more of: *E. coli, Klebsiella pneumonae, Staphylococcus aureus* such as MRSA, *Legionella, Pseudomonas aeruginosa, Serratia marcescens, Enterobacter* spp, *Citrobacter* spp, *Stenotrophomonas maltophilia, Acinetobacter* spp such as *Acinetobacter baumannii, Burkholderia cepacia*, and *Enterococcus* such as vancomycin-resistant *Enterococcus* (VRE).

In one embodiment, said vaccine application may be employed prophylactically, for example to treat a patient before said patient enters a hospital (or similar treatment facility) to help prevent hospital-acquired infection. Alternatively, said vaccine application may be administered to vulnerable patients as a matter of routine.

A related vaccine aspect of the invention provides one or more antibodies (comprising or consisting whole IgG and/or Fab and/or F(ab')$_2$ fragments) that binds to the one or more aforementioned polypeptides of the invention, for use in the prevention, treatment or suppression of CDI (eg. in a mammal such as man). Put another way, the present invention provides a method for the prevention, treatment or suppression of CDI (e.g. in a mammal such as man), said method comprising administration of a therapeutically effective amount of said antibody (or antibodies) to a subject (e.g. a mammal such as man).

By way of example, an anti-Toxin A-based antigen (any A toxinotype) antibody may be employed alone or in combination with an anti-Toxin B-based antigen (any B toxinotype) antibody. Similarly, an anti-Toxin B-based antigen (any B toxinotype) antibody may be employed alone or in combination with an anti-Toxin A-based antigen (any A toxinotype) antibody. Said antibodies may be administered in a sequential or simultaneous manner. Vaccine applications of the present invention may further include the combined use (e.g. prior, sequential or subsequent administration) of one or more antibodies that bind to antigens such as a *C. difficile* antigen (e.g. a non-Toxin antigen; or a *C. difficile* bacterium), and optionally one or more antibodies that bind to one or more nosocomial infection antigens (e.g. an antigen, notably a surface antigen, from a bacterium that causes nosocomial infection; and/or a bacterium that causes a nosocomial infection).

Examples of bacteria that cause nosocomial infection include one or more of: *E. coli, Klebsiella pneumonae, Staphylococcus aureus* such as MRSA, *Legionella, Pseudomonas aeruginosa, Serratia marcescens, Enterobacter* spp, *Citrobacter* spp, *Stenotrophomonas maltophilia, Acinetobacter* spp such as *Acinetobacter baumannii, Burkholderia cepacia*, and *Enterococcus* such as vancomycin-resistant *Enterococcus* (VRE).

In one embodiment, said vaccine application may be employed prophylactically, for example once a patient has entered hospital (or similar treatment facility). Alternatively, said vaccine application may be administered to patients in combination with one or more antibiotics.

In one embodiment, said antibodies have been generated by immunisation of an animal (e.g. a mammal such as man, or a non-human animal such as goat or sheep) with one or more of the aforementioned antigens of the present invention.

In one embodiment, the antibodies of the present invention do not (substantially) bind to the repeat regions of *C. difficile* Toxin A and/or Toxin B.

For the preparation of vaccines for human (or non-human animal) use, the active immunogenic ingredients (whether these be antigenics of the present invention and/or corresponding antibodies of the invention that bind thereto) may be mixed with carriers or excipients, which are pharmaceutically acceptable and compatible with the active ingredient. Suitable carriers and excipients include, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine.

The vaccine may further comprise one or more adjuvants. One non-limiting example of an adjuvant with the scope of the invention is aluminium hydroxide. Other non-limiting examples of adjuvants include but are not limited to: N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Typically, the vaccines are prepared as injectables, either as liquid solutions or suspensions. Of course, solid forms suitable for solution in, or suspension in, liquid prior to injection may also be prepared. The preparation may also be emulsified, or the peptide encapsulated in liposomes or microcapsules.

Vaccine administration is generally by conventional routes e.g. intravenous, subcutaneous, intraperitoneal, or mucosal routes. The administration may be by parenteral injection, for example, a subcutaneous or intramuscular injection.

The vaccines are administered in a manner compatible with the dosage formulation, and in such amount as will be prophylactically and/or therapeutically effective. The quantity to be administered, which is generally in the range of 5 micrograms to 250 micrograms of antigen per dose, depends on the subject to be treated, capacity of the subject's immune system to synthesize antibodies, and the degree of protection desired. Precise amounts of active ingredient required to be administered may depend on the judgment of the practitioner and may be particular to each subject.

The vaccine may be given in a single dose schedule, or optionally in a multiple dose schedule. A multiple dose schedule is one in which a primary course of vaccination may be with 1-6 separate doses, followed by other doses given at subsequent time intervals required to maintain and/or reinforce the immune response, for example, at 1-4 months for a second dose, and if needed, a subsequent dose(s) after several months. The dosage regimen will also, at least in part, be determined by the need of the individual and be dependent upon the judgment of the practitioner.

In one embodiment, a volume X (e.g. 1-6 ml) of buffer solution containing 10-500 µg of a polypeptide of the invention is mixed with an equivalent volume X (i.e. 1-6 ml) of adjuvant (e.g. Freund's complete adjuvant) to form an emulsion. Mixing with the adjuvant is carried out for several minutes to ensure a stable emulsion. A primary immunisation is then performed (e.g. i.m. injection) with said emulsion (e.g. 1-10 ml). In parallel, a volume X (e.g. 1-6 ml) of buffer solution containing 10-500 µg of a polypeptide of the invention is mixed with an equivalent volume X (i.e. 1-6 ml) of adjuvant (e.g. Freund's incomplete adjuvant) to form an emulsion. Mixing with the adjuvant is carried out for several minutes to ensure a stable emulsion. Subsequent immunisations (e.g. 2, 3, 4, 5 or 6) are then performed (e.g. i.m. injection) with said emulsion (e.g. 1-10 ml) on a monthly basis. Antibody titre is typically tested by sampling at a time period of approximately 2 weeks after each of said monthly immunisations, and antibody harvesting is performed when optimal antibody titre has been achieved.

In addition, the vaccine containing the immunogenic antigen(s) may be administered in conjunction with other immunoregulatory agents, for example, immunoglobulins, antibiotics, interleukins (e.g., IL-2, IL-12), and/or cytokines (e.g., IFN gamma)

Additional formulations suitable for use with the present invention include microcapsules, suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of about 0.5% to 10%, including for instance, about 1%-2%.

Antigens of the invention may also have uses as ligands for use in affinity chromatography procedures. In such procedures, antigens of the invention may be covalently immobilised onto a matrix, such as Sepharose, e.g. using cyanogen bromide-activated Sepharose. Such affinity columns may then be used to purify antibody from antisera or partially purified solutions of immunoglobulins by passing them through the column and then eluting the bound IgG fraction (e.g. by low pH). Almost all of the antibody in the eluted fraction will be directed against the antigen of the invention, with non-specific antibodies and other proteins having been removed. These affinity purified IgG fractions have applications both as immunotherapeutics and as reagents in diagnostics. For immunotherapeutics, affinity purified antibodies enable a lower dose to be administered making adverse side effects less likely. For diagnostics, affinity purified agents often give improved specificity and fewer false positive results.

DEFINITIONS

*Clostridium difficile* is a species of Gram-positive bacterium of the genus *Clostridium*.

*Clostridium difficile* infection (CDI) means a bacterial infection which affects humans and animals and which results in a range of symptoms from mild self-limiting diarrhoea to life-threatening conditions such as pseudomembranous colitis and cytotoxic megacolon. In this disease, *C. difficile* replaces some of the normal gut flora and starts to produce cytotoxins which attack and damage the gut epithelium. Primary risk factors for human CDI include: receiving broad-spectrum antibiotics, being over 65 years old and being hospitalised.

*Clostridium difficile* Toxin A is a family of protein cytotoxins/enterotoxins of approximately 300 kDa in size. Toxin A has an enzyme activity within the N-terminal region which acts to disrupt the cytoskeleton of the mammalian cell causing cell death. There are a number of naturally occurring variants of Toxin A within the strains of *Clostridium difficile* which are called 'toxinotypes'. The various toxinotypes of Toxin A have variations within their primary sequence of usually <10% overall. Examples of suitable Toxin A sequences include SEQ ID NOs: 1 and 3.

*Clostridium difficile* Toxin B is a family of protein cytotoxins of approximately 270 kDa in size which are similar to Toxin A but significantly more cytotoxic. Like Toxin A, Toxin B has an enzyme activity within the N-terminal region which acts to disrupt the cytoskeleton of the mammalian cell causing cell death. There are a number of naturally occurring variants of Toxin B within the strains of *C. difficile* which are called 'toxinotypes'. The various toxinotypes of Toxin B have variations within their primary sequence of up to 15% overall. Examples of suitable Toxin B sequences include SEQ ID NOs: 2 and 4.

*C. difficile* repeat units are regions within the C-terminus of Toxin A and Toxin B that contain repeating motifs which were first identified by von Eichel-Streiber and Sauerborn (1990; Gene 30:107-113). In the case of Toxin A there are 31 short repeats and 7 long repeats with each repeat consisting of a β-hairpin followed by a loop. Toxin B consists of a similar structure but with fewer repeats. The repeat units of Toxin A are contained within residues 1850-2710 and those for Toxin B within residues 1852-2366. The repeat regions play a role in receptor binding. The receptor binding regions (i.e. that define the toxin's structural binding pockets) appear to be clustered around the long repeat regions to form 'binding modules.'

Central domains of Toxin A and B are believed to play a role in translocation of the toxins into mammalian cells. The central domains of Toxin A are based on residues 542-1849 and those for Toxin B are based on residues 543-1851. Of the central domain regions of Toxin A and Toxin B, the first domain is a cysteine protease, which plays a role in the internalisation of the toxin's effector domain (which contains the glucosyl transferase activity).

Toxinotypes are often used to classify strains of *C. difficile*. Toxinotyping is based on a method which characterises the restriction patterns obtained with the toxin genes. Toxinotypes of Toxin A and Toxin B represent variants, by primary amino acid sequence, of these protein toxins. In one embodiment, the *C. difficile* toxin is selected from one of toxinotypes 0 to XV. Preferred Toxinotypes (plus example Ribotypes and Strains) are listed in the Table immediately below. The listed Toxinotypes are purely illustrative and are not intended to be limiting to the present invention.

| Toxinotype | Example Ribotypes | Example Strains | Reference |
|---|---|---|---|
| 0 | 001, 106 | VPI10463 | Rupnik et al. |
| 1 | 003, 012, 102 | EX623 | (1998) |
| 2 | 103 | AC008 | J. Clinical |
| 3 | 027, 034, 075, 080 | R20291, QCD-32g58 | Microbiol. 36: 2240-2247 |
| 4 | 023, 034, 075, 080 | 55767 | |
| 5 | 066, 078 | SE881 | |
| 6 | 045, 063, 066 | 51377 | |
| 7 | 063 | 57267 | |

-continued

| Toxinotype | Example Ribotypes | Example Strains | Reference |
|---|---|---|---|
| 8 | 017, 047 | 1470 | |
| 9 | 019 | 51680 | |
| 10 | 036 | 8864 | |
| 11 | 033 | IS58, R11402 | Rupnik et al. |
| 12 | 056 | IS25 | (2001) |
| 13 | 070 | R9367 | Microbiology |
| 14 | 111 | R10870 | 147: 439-447 |
| 15 | 122 | R9385 | |

An "antibody" is used in the broadest sense and specifically covers polyclonal antibodies and antibody fragments so long as they exhibit the desired biological activity. For example, an antibody is a protein including at least one or two, heavy (H) chain variable regions (abbreviated herein as VHC), and at least one or two light (L) chain variable regions (abbreviated herein as VLC). The VHC and VLC regions can be further subdivided into regions of hypervariability, termed "complementarity determining regions" ("CDR"), interspersed with regions that are more conserved, termed "framework regions" (FR). The extent of the framework region and CDRs has been precisely defined (see, Kabat, E. A., et al. Sequences of Proteins of Immunological Interest, Fifth Edition, U.S. Department of Health and Human Services, NIH Publication No. 91-3242, 1991, and Chothia, C. et al, J. Mol. Biol. 196:901-917, 1987, which are incorporated herein by reference). Preferably, each VHC and VLC is composed of three CDRs and four FRs, arranged from amino-terminus to carboxy-terminus in the following order: FR1, CDR1, FR2, CDR2, FR3, CDR3, FR4.

The VHC or VLC chain of the antibody can further include all or part of a heavy or light chain constant region. In one embodiment, the antibody is a tetramer of two heavy immunoglobulin chains and two light immunoglobulin chains, wherein the heavy and light immunoglobulin chains are interconnected by, e.g., disulfide bonds. The heavy chain constant region includes three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (CIq) of the classical complement system. The term "antibody" includes intact immunoglobulins of types IgA, IgG, IgE, IgD, IgM (as well as subtypes thereof), wherein the light chains of the immunoglobulin may be of types kappa or lambda.

The term antibody, as used herein, also refers to a portion of an antibody that binds to a toxin of C. difficile (e.g. Toxin A or Toxin B), e.g., a molecule in which one or more immunoglobulin chains is not full length, but which binds to a toxin. Examples of binding portions encompassed within the term antibody include (i) a Fab fragment, a monovalent fragment consisting of the VLC, VHC, CL and CH1 domains; (ii) a F(ab')$_2$ fragment, a bivalent fragment comprising two Fab fragments linked by a disulfide bridge at the hinge region; (iii) a Fc fragment consisting of the VHC and CH1 domains; (iv) a Fv fragment consisting of the VLC and VHC domains of a single arm of an antibody; (v) a dAb fragment (Ward et al., Nature 341:544-546, 1989), which consists of a VHC domain; and (vi) an isolated complementarity determining region (CDR) having sufficient framework to bind, e.g. an antigen binding portion of a variable region. An antigen binding portion of a light chain variable region and an antigen binding portion of a heavy chain variable region, e.g., the two domains of the Fv fragment, VLC and VHC, can be joined, using recombinant methods, by a synthetic linker that enables them to be made as a single protein chain in which the VLC and VHC regions pair to form monovalent molecules (known as single chain Fv (scFv); see e.g., Bird et al. (1988) Science 1Al-ATi-Alβ; and Huston et al. (1988) Proc. Natl. Acad. Sci. USA 85:5879-5883). Such single-chain antibodies (as well as camelids) are also encompassed within the term antibody. These are obtained using conventional techniques known to those with skill in the art, and the portions are screened for utility in the same manner as are intact antibodies.

The term "fragment" means a peptide typically having at least 70, 90, 110, 130, 150, 170, 190, 210, 230, 250, 270, 290, 310, 330, 350 contiguous amino acid residues of (based on) the corresponding reference sequence.

The term "variant" means a peptide or peptide fragment having at least eighty, preferably at least eighty five, more preferably at least ninety percent amino acid sequence homology with a reference polypeptide sequence (e.g., a C. difficile toxin polypeptide amino acid sequence, and/or a fusion protein partner amino acid sequence, and/or an SLP amino acid reference sequence. For sequence comparison, typically one sequence acts as a reference sequence, to which test sequences may be compared. When using a sequence comparison algorithm, test and reference sequences are input into a computer, subsequent coordinates are designated, if necessary, and sequence algorithm program parameters are designated. The sequence comparison algorithm then calculates the percentage sequence identity for the test sequence(s) relative to the reference sequence, based on the designated program parameters.

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position—Specific Gap Penalties and Weight Matrix Choice, 22(22) Nucleic Acids Research 4673-4680 (1994); and iterative refinement, see, e.g., Osamu Gotoh, Significant Improvement in Accuracy of Multiple Protein Sequence Alignments by Iterative Refinement as Assessed by Reference to Structural Alignments, 264(4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262(5131) Science 208-214 (1993); Align-M, see, e.g., Ivo Van Walle et al., Align-M—A New Algorithm for Multiple Alignment of Highly Divergent Sequences, 20(9) Bioinformatics:1428-1435 (2004).

Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown below (amino acids are indicated by the standard one-letter codes).

Alignment Scores for Determining Sequence Identity

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

The percent identity is then calculated as:

$$\frac{\text{Total number of idential matches}}{[\text{length of the longer sequence plus the number of gaps introduced into the longer sequence in order to align the two sequences}]} \times 100$$

Substantially homologous polypeptides are characterized as having one or more amino acid substitutions, deletions or additions. These changes are preferably of a minor nature, that is conservative amino acid substitutions (see below) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag.

| Conservative amino acid substitutions | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

In addition to the 20 standard amino acids, non-standard amino acids (such as 4-hydroxyproline, 6-N-methyl lysine, 2-aminoisobutyric acid, isovaline and α-methyl serine) may be substituted for amino acid residues of the polypeptides of the present invention. A limited number of non-conservative amino acids, amino acids that are not encoded by the genetic code, and unnatural amino acids may be substituted for clostridial polypeptide amino acid residues. The polypeptides of the present invention can also comprise non-naturally occurring amino acid residues.

Non-naturally occurring amino acids include, without limitation, trans-3-methylproline, 2,4-methano-proline, cis-4-hydroxyproline, trans-4-hydroxy-proline, N-methylglycine, allo-threonine, methyl-threonine, hydroxy-ethylcysteine, hydroxyethylhomo-cysteine, nitro-glutamine, homoglutamine, pipecolic acid, tert-leucine, norvaline, 2-azaphenylalanine, 3-azaphenyl-alanine, 4-azaphenyl-alanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell free system comprising an E. coli S30 extract and commercially available enzymes and other reagents. Proteins are purified by chromatography. See, for example, Robertson et al., J. Am. Chem. Soc. 113:2722, 1991; Ellman et al., Methods Enzymol. 202:301, 1991; Chung et al., Science 259:806-9, 1993; and Chung et al., Proc. Natl. Acad. Sci. USA 90:10145-9, 1993). In a second method, translation is carried out in Xenopus oocytes by microinjection of mutated mRNA and chemically aminoacylated suppressor tRNAs (Turcatti et al., J. Biol. Chem. 271:19991-8, 1996). Within a third method, E. coli cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochemistry 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395-403, 1993).

A limited number of non-conservative amino acids, amino acids that are not encoded by the genetic code, non-naturally occurring amino acids, and unnatural amino acids may be substituted for amino acid residues of polypeptides of the present invention.

Essential amino acids in the polypeptides of the present invention can be identified according to procedures known in the art, such as site-directed mutagenesis or alanine-scanning mutagenesis (Cunningham and Wells, Science 244:1081-5, 1989). Sites of biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306-12, 1992; Smith et al., J. Mol. Biol. 224:899-904, 1992; Wlodaver et al., FEBS Lett. 309:59-64, 1992. The identities of essential amino acids can also be inferred from analysis of homologies with related components (e.g. the translocation or protease components) of the polypeptides of the present invention.

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenised polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Toxin-neutralising means the capacity of a substance to prevent the cytotoxic action of either Toxin A or Toxin B on a mammalian cell. In assays for toxin-neutralising activity, a fixed amount of toxin is mixed with various concentrations of a neutralising substance (e.g. an antibody) and the mixture applied to and incubated with a mammalian cell line (e.g. Vero cells) for a fixed time. The neutralising titre may be measured by several methods:

(a) The dilution of the substance (serum, antibody, purified IgG) that completely protects the cells from the cytotoxic effects of either Toxin A or Toxin B. These cytotoxic effects are evident by cell rounding and endpoint may be quantified by microscopy methods.

(b) The dilution of the substance (serum, antibody, purified IgG) that protects 50% of the cells ($ED_{50}$ titre) from the cytotoxic effects of either Toxin A or Toxin B. The $ED_{50}$ titre may be assessed by the use of dyes (e.g. crystal violet) which give a measure of cell integrity. Fitting titration data to either 4- or 5-parameter logistic curves provides an accurate estimation of the $ED_{50}$ titre. $ED_{50}$ estimations, which are generally more accurate than microscopy based methods, provide a quantitative estimation of the toxin-neutralising capacity of serum and purified antibodies.

Toxin-neutralising titres are measured in the presence of a fixed concentration of Toxin A or Toxin B which is set at a multiple of that required to induce cell death over a 24 hour incubation period. Typically, final concentrations of Toxin A may be set at 50 ng/ml and Toxin B between 0.5-2 ng/ml. The difference in the concentrations between Toxin A and Toxin B reflect the significantly higher specific cytotoxic activity of Toxin B. Thus, an $ED_{50}$ titre for an antibody of serum solution of 1000 units/ml indicates that at a 1000-fold dilution, the antibody solution is capable of neutralising 50% of the Toxin A or Toxin B cytotoxic activity. With respect to titres in serum, a toxin-neutralising titre ≥1000 unit/ml may be regarded as potent neutralising activity.

For highly purified IgG solutions, neutralising activity may also be expressed as the concentration of IgG (µg/ml) required to neutralise 50% of the Toxin A or Toxin B cytotoxic activity. In this case, a titre value ≤10 µg/ml IgG may be regarded as potent neutralising activity.

*C. difficile* surface proteins (SLPs) means those proteins that are associated with the bacterial cell wall. Examples of 29 *C. difficile* surface (cell wall proteins) are given in Table 1 of Fagan et al. (2011) J. Medical Microbiol. 60:1225-1228, which is hereby incorporated in its entirety by reference thereto.

DESCRIPTION OF THE DRAWINGS

FIG. 1 illustrates the structures of *C. difficile* Toxin A and Toxin B showing amino acid residues at the various domain boundaries.

FIG. 2 illustrates the purification of Toxin B recombinant fragment residues 767-1852 as a fusion protein with thioredoxin. The left-hand Figure shows a 4-12% SDS-PAGE analysis of TxB3. Columns C2-C8 show lanes with partially purified fragment.

FIG. 3 illustrates the purification of Toxin A recombinant fragment residues 542-1850 as a fusion protein with thioredoxin.

FIG. 4 depicts the expression and purification of CD2767 (residues 27-401). Purification of CD2767 (residues 27-401) by immobilised metal ion affinity chromatography. Key: column load, L; flow through fraction, FT; eluted purified CD2767 polypeptide, El. The intense band of the CD2767 polypeptide is illustrative of its high solubility.

FIG. 5 depicts the expression and purification of a fusion protein consisting of CD2767 (residues 27-401) with Toxin A (residues 543-1851). The fusion protein was expressed as a soluble polypeptide (top band in lanes C1 and C2) at approximately 2% of the total protein. C1 and C2 represent duplicates of the soluble fraction of the total expressed protein.

FIG. 6 demonstrates the antibody-mediated neutralisation of Toxin A and Toxin B as measured by the Vero cell $ED_{50}$ assay. The capacity of various dilutions of antiserum to Toxin A (residues 543-1851) (●) to prevent the cytotoxic effects of purified Toxin A (50 ng/ml) was assessed using crystal violet staining to measure cell viability. Reduced absorbance indicates a lack of cell integrity. Neutralisation by Toxin B (residues 767-1852) antiserum (▼) was assessed using Toxin B at 2 ng/ml. Each antiserum was a pool obtained from the immunisation of 3 sheep.

DETAILED DESCRIPTION

Examples

Example 1

Expression and Purification of Toxin B Fragment Recombinant Fragment Residues 767-1852 as a Fusion Protein with Thioredoxin ($His_6$TrxTxBcentral)

Expression

L-broth (100 ml) supplemented with 200 µg/ml ampicillin and 0.4% glucose was inoculated with a scrape from a glycerol freeze (BL21 (DE3) *E. coli* harbouring plasmid pET59His$_6$TrxTxBcentral) and maintained overnight at 30°

C. and 180 rpm. The overnight culture was used as a 2.5% inoculum for Terrific Broth (4×1 L in 2.5 L unbaffled flasks) supplemented with 200 μg/ml ampicillin and 0.2% glucose. Cultures were maintained at 37° C. with orbital shaking (180 rpm) to an absorbance at 600 nm of 0.6. The temperature of the cultures was reduced to 16° C. and protein expression induced with the addition of 1 mM IPTG. The culture was maintained overnight at 16° C. with orbital shaking as before. Cell paste (60 g) was harvested by centrifugation (Sorvall RC3BP centrifuge, H6000A rotor, 4000 g for 20 minutes).

Immobilised Nickel Affinity Purification of $His_6TrxTxBcentral$

Cells (60 g) were resuspended in buffer (pH 8, 20 mM Tris, 50 mM NaCl) and subjected to lysis using sonication. The lysate was cleared by centrifugation (Sorvall RC5C centrifuge, SS-34 rotor, 20,000 g, 20 minutes) and made up to 1 M ammonium sulphate with a saturated solution. The solution was stored on ice for 1 hour and the resultant precipitate collected by centrifugation (Heraeus Multifuge X3R centrifuge, 4000 g, 4° C.). The precipitate was resuspended in 250 ml of low imidazole buffer (pH 7.5, 50 mM Hepes, 0.5 M NaCl, 20 mM imidazole) and applied to a 30 ml nickel column (Ø26 mm) at a flow rate of 3 ml/min. The column was washed with low imidazole buffer and bound protein eluted using a gradient from 0-100% high imidazole buffer (pH 7.5, 50 mM Hepes, 0.5 M NaCl, 0.5 M imidazole). Fractions were analysed on 4-12% NuPAGE Bis-Tris polyacrylamide gels with coomassie staining. SDS PAGE of partially purified fractions are shown in FIG. 2.

Example 2

Expression and Purification of Toxin A Fragment Recombinant Fragment Residues 542-1850 (TxACPD)

L-broth (100 ml) supplemented with 100 μg/ml ampicillin and 0.2% glucose was inoculated with a glycerol freeze (BL21 (DE3) E. coli harbouring plasmid pET59TxACPDcentral). The culture was maintained (37° C., 180 rpm) to an absorbance at 600 nm of 0.6. The 100 ml culture was used as a 2% inoculum for Terrific Broth (4×0.75 L) supplemented with 200 μg/ml ampicillin and 0.2% glucose. Cultures were maintained at 37° C. with orbital shaking (180 rpm) to an absorbance at 600 nm of 0.6. The temperature of the cultures was reduced to 16° C. and protein expression induced 1 hour later with the addition of 1 mM IPTG. The culture was maintained overnight at 16° C. with orbital shaking as before. Cell paste (37 g) was harvested by centrifugation (Sorvall RC3BP centrifuge, H6000A rotor, 4000 g, 20 minutes) and stored at −80° C.

Cells (37 g) were resuspended with 260 ml buffer (20 mM Tris, 50 mM NaCl, pH 8) and subjected to lysis using sonication. The lysate was cleared by centrifugation (30,000 g, 20 minutes) and the clarified lysate stirred gently over ice whilst 130 ml of saturated ammonium sulphate solution (pH 8) was added to bring the mixture to 33% saturation. The mixture was left on ice for 15-20 minutes to allow a cloudy white precipitate to form. The precipitate was harvested by centrifugation (30,000 g, 15 minutes) and resuspended in 70 ml 'low imidazole' buffer (pH7.5, 50 mM Hepes, 0.5 M NaCl, 20 mM imidazole, 5% glycerol). The solution was applied to a 30 ml nickel column (Ø26 mm) at a flow rate of 2 ml/min. The column was washed at 2 ml/min until the UV absorbance of the flow through returned to near baseline levels. Bound material was eluted from the column with a 160 ml gradient (2 ml/min) to 100% 'high imidazole' buffer (pH7.5, 50 mM Hepes, 0.5 M NaCl, 0.5 M imidazole, 15% glycerol). Fractions were analysed on 4-12% NuPAGE Bis-Tris polyacrylamide gels and those containing the highest amount of the expression construct pooled.

For cleavage of the $His_6$Thioredoxin tag, protein solution containing the constructs (18 ml, 1.5 mg/ml) from the first immobilised nickel column was thawed at room temperature and restriction grade thrombin (30 U) was added and the mixture was incubated at room temperature ~20° C. for 16-18 hours.

The protein mix was loaded at 1 ml/min onto the column consisting of 30 ml (Ø26 mm) nickel charged chelating Sepharose column equilibrated with buffer A (50 mM HEPES, 0.5 M NaCl, 20% glycerol, pH 7.5). The column was washed with 30 ml buffer A. Bound protein was then eluted using 4% (50 ml), 8% (50 ml) and finally a gradient (120 ml) to 100% buffer B (50 mM HEPES, 0.5 M NaCl, 0.5 M imidazole, 20% glycerol, pH 7.5). The fraction containing the purified fractions were analysed by SDS PAGE and the fractions containing the purest construct pooled and dialysed into storage buffer (pH 7.5, 50 mM Hepes, 0.5 M NaCl, 20% glycerol).

SDS PAGE Analysis and Western Blot Analysis of Purified TxACPD Constructs

Purified protein solution was mixed 1:1 with 4×SDS-PAGE loading buffer supplemented with 5 mM DTT. The sample was heated at 95° C. for five minutes and loaded in duplicate (5 and 10 μl) onto a 4-12% NuPAGE Bis-Tris polyacrylamide gel. The gel was run in MES running buffer at 200 V for 45 minutes. One part of the gel was subjected to coomassie staining and the other blotted onto a nitrocellulose membrane at 40 V for 1 hour in transfer buffer. The membrane was blocked with 5% skimmed milk in tris buffered saline supplemented with 0.1% Tween 20 (TBST) for 40 minutes. The membrane was incubated for 40 minutes with sheep anti-Toxin A antibody diluted 1:25,000 in 1% skimmed milk TBST. The stock antibody concentration was 50 mg/ml. The membrane was washed for 4×15 minutes in TBST. A donkey anti-sheep antibody alkaline phosphatase conjugate was applied to the membrane at a dilution of 1:10,000 in 1% skimmed milk TBST. The solution was left on the membrane for 40 minutes with gentle agitation as before. The membrane was washed as before with TBST and the blot developed using NBT/BCIP one step reagent. SDS PAGE and Western blot are shown in FIG. 3.

Example 3

Expression and Purification of Residues 27-401 of C. difficile Protein CD2767

A synthetic gene which encodes residues 27-401 of C. difficile protein CD2767 was synthesised commercially with its codon bias optimised for expression in a host such as E. coli. The gene was inserted into a pET28a expression vector and transformed into a BL21 E. coli expression strain using standard molecular biology procedures. The E. coli expression strain was grown and protein expression induced with IPTG essentially as described in Example 1 except kanamycin was used in place of ampicillin. Cell pellets were either used directly or frozen at −20° C.

For protein extraction, cells were thawed and resuspended in 50 mM Tris HCl pH 8.0 buffer containing 0.5 M NaCl and 20 mM imidazole, sonicated (6×30 sec with 30 sec cooling after each) and then centrifuged at 47000×g for 20 min. The His6-tagged residue 27-401 CD2767 polypeptide was then purified from the supernatant fluid by using immobilised metal ion (Ni) affinity chromatography. Application of the sample to the column and washing was in the above Tris/NaCl/imidazole buffer. The purified construct was then eluted with a gradient to 0.5 M imidazole in the same buffer.

The CD2767 (residues 27-401) polypeptide was obtained as >90% pure protein by the single purification step and appeared as an intense band of approx. 47 kDa on SDS PAGE (FIG. 4). The protein fragment could be concentrated to >120 mg/ml as measured by absorbance at 280 nm or to >167 mg/ml as measured by the Bradford protein assay (bovine serum albumin as a standard). Both these assays illustrate the extremely high solubility of the CD2767 (residues 27-401) polypeptide and its potential usefulness as a solubility enhancing component within recombinant fusion proteins.

Example 4

Expression and Purification of Either Toxin a or Toxin B Recombinant Fragments as a Fusion Protein with Residues 27-401 of *C. difficile* Protein CD2767

A synthetic gene which encodes a fusion protein in which the N-terminus consists of residues 27-401 of *C. difficile* protein CD2767 and the C-terminus consists of Toxin B fragment recombinant fragment residues 767-1852 may be synthesised commercially with its codon bias optimised for expression in a host such as *E. coli*. A synthetic gene which encodes a fusion protein in which the N-terminus consists of residues 27-401 of *C. difficile* protein CD2767 and the C-terminus consists of Toxin A fragment recombinant fragment residues 770-1850 may be similarly obtained. These and other fusion proteins may be incorporated with expression vectors with various purification tags (6 histidine) incorporated to facilitate purification. An example of such an expression construct is shown in SEQ ID NO: 19 which consists of CD2767 (residues 27-401) and Toxin A (residues 542-1850).

Expression and purification of the above constructs may be undertaken by similar methods as those outlined in Examples 1 and 2 and expression of a construct consisting of CD2767 (residues 27-401) as an N-terminal fusion to Toxin A (residues 543-1851) is shown in FIG. 5. Here, addition of the CD2767 domain to the Toxin A fragments renders it soluble and expressible as 2% of the total soluble protein. After expression in *E. coli*, purification of the construct is effected by immobilised metal ion affinity chromatography and other chromatography methods such as ion exchange chromatography.

Example 5

Formulation of Antigens of the Invention for Immunisation of Animals

Purified *C. difficile* antigens at a concentration of between 0.5-2 mg/ml (nominally 1 mg/ml) were dialysed against a suitable buffer (e.g. 10 mM Hepes buffer pH 7.4 containing 150 mM NaCl) and then formaldehyde added to a final concentration of 0.2% and incubated for up to 7 days at 35° C. After incubation, the formaldehyde may optionally be removed by dialysis against a suitable buffer, e.g. phosphate buffered saline.

For sheep, 2 ml of buffer solution containing between 10 and 500 μg of the above *C. difficile* antigen is mixed with 2.6 ml of Freund's adjuvant to form an emulsion. Mixing with the adjuvant is carried out for several minutes to ensure a stable emulsion. The complete form of the adjuvant is used for the primary immunisation and incomplete Freund's adjuvant for all subsequent boosts.

Example 6

Generation of Antibodies to Antigens of the Invention

A number of conventional factors are taken into consideration during the preparation of antiserum in order to achieve the optimal humoral antibody response. These include: breed of animal; choice of adjuvant; number and location of immunisation sites; quantity of immunogen; and number of and interval between doses. Conventional optimisation of these parameters is routine to obtain specific antibody levels in excess of 6 g/liter of serum.

For sheep, an emulsion of the antigen with Freund's adjuvant was prepared as described in Example 5. The complete form of the adjuvant is used for the primary immunisation and incomplete Freund's adjuvant for all subsequent boosts. About 4.2 ml of the antigen/adjuvant mixture was used to immunise each sheep by i.m. injection and spread across 6 sites including the neck and all the upper limbs. This was repeated every 28 days. Blood samples were taken 14 days after each immunisation.

For comparison of the toxin-neutralising immune response to the different antigens, 3 sheep were used per antigen. They were immunised as above using an identical protocol and the same protein dose per immunisation.

Example 7

Assessment of the Neutralising Efficacy of Antisera to Toxins Using the In Vitro Cell Assay The toxin neutralizing activity of the antisera against *C. difficile* Toxins was measured by cytotoxicity assays using Vero cells. A fixed amount of either purified *C. difficile* Toxin A or Toxin B was mixed with various dilutions of the antibodies, incubated for 30 min at 37° C. and then applied to Vero cells growing on 96-well tissue culture plates. Both Toxin A and Toxin B possess cytotoxic activity which results in a characteristic rounding of the Vero cells over a period of 24-72 h. In the presence of neutralising antibodies this activity is inhibited and the neutralising strength of an antibody preparation may be assessed by the dilution required to neutralise the effect of a designated quantity of either Toxin A or Toxin B.

Data demonstrating the neutralising activity of ovine antibody to various recombinant *C. difficile* Toxin B antigens are shown in Table 1 and Table 2. In these experiments, various dilutions of ovine antibody were mixed with Toxin B at a final concentration of 0.5 ng/ml and incubated for 30 min at 37° C. and then applied to Vero cells as above and incubated at 37° C. and monitored over a period of 24-72 h. The antibody dilutions which completely protect the cells against the cytotoxic effects of the Toxin B were calculated.

Table 1 shows the neutralising titres of an antigen of the invention and Table 2 shows the titres obtained using an antigen which consists of just the repeat regions. Collectively, the data in Tables 1 and 2 show the superior capacity of antigens of the invention to elicit a toxin-neutralising immune response compared to fragments containing just the repeat domains.

Antibody toxin neutralisation titres were also estimated by colorimetric assays based on cell staining with crystal violet (Rothman (1986) J. Clin. Pathol. 39:672-676). Vero cells were grown to confluence in 96-well cell culture plates. These assays were performed as described above using final concentrations of Toxin A and Toxin B in antibody mixtures of 50 ng/ml and 2 ng/ml, respectively. After overnight incubation, cells were washed gently with 200 μl of Dulbecco's-PBS (Sigma) which was carefully removed before the cells were fixed with 70 μl ice cold ethanol for 2 min. The ethanol was then removed and 70 μl crystal violet (1% w/v in ethanol; Pro-Lab) was added to the fixed cells and incubated for 30 minutes at 22° C. Plates were then washed carefully by immersion in deionized water to remove excess dye, dried at 37° C. and then 200 μl of 50% (v/v) ethanol added. Plates were then incubated at 37° C. in a shaker incubator (300 rpm) for 2 h before being read at 492 nm. $ED_{50}$ values were derived from the resulting toxin neutralisation curves using 4- or 5-pI nonlinear regression models (FIG. 4). Thus, the $ED_{50}$ titre is the dilution of the serum or antibody required to achieve the 50% toxin-neutralising endpoint in the assay. If antibody solutions of known IgG concentrations are used, the titres may also be expressed as the concentration of IgG required to achieve the 50% toxin-neutralising endpoint.

Table 3 shows the toxin-neutralising $ED_{50}$ titres obtained using the crystal violet method for the serum generated using the central domains of both Toxin A and Toxin B. For both fragments, toxin-neutralising $ED_{50}$ titres in excess of 1000 unit/ml were obtained for their respective sera (see also FIG. 6).

Toxin-neutralizing $ED_{50}$ titre values obtained for a sheep anti Toxin B (residues 767-1852) IgG solution are shown in Table 4. The neutralising titres against various toxinotypes of Toxin B were obtained for this fragment antiserum in order to assess its cross neutralising efficacy. Each purified toxinotype of Toxin B was normalised for toxicity in the assay and held at a fixed concentration of 16× the minimum toxin concentration which causes cell death in a 24 hr incubation period. Neutralising potencies are expressed in μg/ml IgG required for 50% neutralisation of the above Toxin B concentration. Less than a 4-fold difference in neutralising titres was observed which is indicative of good cross-neutralising efficacy.

Example 8

Assessment of the In Vivo Efficacy of Antiserum Generated Using Recombinant Antigens of the Invention for Treating CDI To demonstrate the efficacy of the antisera generated, using recombinant antigens, to treat CDI in vivo, Syrian hamsters are passively immunised with antibodies which have neutralising activity against one or more of the toxins of C. difficile. For assessing the efficacy of a treatment formulation, hamsters will be given antibody either intravenously or by the intraperitoneal route at various times from 6 hours post-challenge to 240 hours post challenge with C. difficile.

Prior to passive immunisation hamsters are administered a broad spectrum antibiotic (e.g. clindamycin) and 12-72 h later challenged with C. difficile spores by mouth. Animals are then monitored for up to 15 days for symptoms of C. difficile-associated disease. Control, non-immunised animals develop signs of the disease (e.g. diarrhoea, swollen abdomen, lethargy, ruffled fur) while those treated with ovine antibody appear normal or show statistically significant reduced incidence of disease.

Example 9

Vaccination by Peptide/Peptide Fragments of the Invention

A vaccine, represented by a peptide/peptide fragment of the invention is prepared by current Good Manufacturing Practice. Using such practices, peptides/peptide fragments of the invention may be bound to an adjuvant of aluminium hydroxide which is commercially available (e.g. Alhydrogel). The vaccine would normally contain a combination of antigens of the invention derived from Toxin A and Toxin B but could also contain either Toxin A or Toxin B antigens. The vaccine may also contain Toxin A and Toxin B antigens in combination with other antigens of bacterial or viral origin.

Purified C. difficile Toxin A and/or Toxin B antigen of the invention may be treated with formaldehyde at a final concentration of 0.2% and incubated for up to 24 hours at 35° C. (as described in Example 5).

In addition to the antigens of the invention, a typical vaccine composition comprises:

A) A buffer (e.g., Hepes buffer between 5 and 20 mM and pH between 7.0 and 7.5;

B) A salt component to make the vaccine physiologically isotonic (e.g., between 100 and 150 mM NaCl);

C) An adjuvant (e.g., aluminium hydroxide at a final aluminium concentration of between 100 and 700 μg per vaccine dose); and D) A preservative (e.g., Thiomersal at 0.01% or formaldehyde at 0.01%).

Such vaccine compositions are administered to humans by a variety of different immunisation regimens, such as:

1. A single dose (e.g., 20 μg adsorbed fragment of the invention) in 0.5 ml administered sub-cutaneously.

2. Two doses (e.g., of 10 μg adsorbed fragment of the invention) in 0.5 mls administered at 0 and 4 weeks.

3. Three doses (e.g., of 10 μg adsorbed fragment of the invention) in 0.5 mls administered at 0, 2 and 12 weeks.

These vaccination regimens confer levels of protection against exposure to the homologous serotypes of C. difficile toxins Example 10

Clinical Use of Antibodies Produced Using Antigens of the Invention

Three examples serve to illustrate the therapeutic value of the systemic ovine antibody products, produced using antigens of the invention, in patients with differing degrees of seventy in their CDI.

Mild CDI

A 67 year old male is admitted to a coronary care unit following a severe myocardial infarction. Whilst making an uneventful recovery he develops a mild diarrhoea without any other signs or symptoms. Because there have been recent episodes of CDI in the hospital, a faecal sample is sent immediately for testing and found to contain both Toxin A and Toxin B. After isolation to a single room with its own toilet he receives 250 mg of the ovine F(ab')$_2$ intravenously followed by a second injection two days later. His diarrhoea stops quickly and he makes a full recovery without the need of either metranidazole or vancomycin.

Severe CDI with Risk of Relapse

A female aged 81 falls in her home and sustained a fractured left hip. She is immediately admitted to hospital and the hip is pinned successfully. Her frail condition prevented early discharge and, a few days later, she develops a productive cough for which she was given a wide spectrum antibiotic. After a further eight days she develops profuse diarrhoea with abdominal pain and tenderness and CDI is diagnosed by the appropriate faecal tests. At the time there is also evidence of systemic manifestations of the infection including a markedly raised white blood cell count, and of significant fluid loss with dehydration. The patient is started immediately on oral vancomycin and, at the same time, receives the first of five daily injections of 250 mg of the ovine F(ab')$_2$-based product intravenously. There is a rapid resolution of the signs and symptoms and of the laboratory manifestations of CDI. However, in order to avoid the risk of relapse of her CDI following stopping vancomycin, she continues to be treated for a further two weeks on an oral form of the antibody therapy. She experiences no relapse.

Severe CDI with Complications

An 87 year old female develops bronchopneumonia while resident in long-stay care facilities. The local general practitioner starts her on a course of antibiotic therapy with immediate benefit. However, eight days after stopping the antibiotic she experiences severe diarrhoea. Her condition starts to deteriorate necessitating admission to hospital where Toxin A is detected in her faeces by an ELISA test. By this time she is extremely ill with evidence of circulatory failure and her diarrhoea has stopped. The latter is found to be due a combination of paralytic ileus and toxic megacolon and an emergency total colectomy is considered essential. Since such surgery is associated with a mortality in excess of 60% she receives intravenous replacement therapy together with the contents of two ampoules (500 mg) of antibody product. By the time she is taken to the operating theatre four hours later, her general condition had improved significantly and she survives surgery.

TABLE 1

Neutralisation titres obtained by immunisation of sheep with a recombinant Toxin B-derived antigen (TxBcentral; residues 767-1852) of the invention

| Antigen | No of Doses | Immunisation period (weeks) | Neutralisation titre against Toxin B (0.5 ng/ml) |
|---|---|---|---|
| Recombinant Toxin B (residues 767-1852) at 100 µg/dose | 2 | 6 | 480 |
| | 3 | 10 | 5,120 |
| | 4 | 14 | 5,120 |
| | 5 | 18 | 5,120 |

TABLE 2

Neutralisation titres obtained by immunisation of sheep with a recombinant Toxin B-derived antigen (TxB2, residues 1756-2366) representing the repeat regions

| Antigen | No of Doses | Immunisation period (weeks) | Neutralisation titre against Toxin B (0.5 ng/ml) |
|---|---|---|---|
| Recombinant Toxin B (residues 1756-2366) at 100 µg/dose | 2 | 6 | <10 |
| | 3 | 10 | 10 |
| | 4 | 14 | 10 |
| | 5 | 18 | 80 |

TABLE 3

Neutralisation $ED_{50}$ titres obtained by immunisation of sheep with a recombinant antigensToxin B (residues 767-1852) and Toxin A (residues 543-1851)

| | | Neutralising titre $ED_{50}$ | | |
|---|---|---|---|---|
| Antigen | ELISA Titre | 1 | 2 | Mean |
| Toxin B (767-1852) | $1 \times 10^5$ | 7946 ± 1027 | 8225 ± 418 | 8086 |
| Toxin A (542-1850) | $2 \times 10^5$ | 2472 ± 199 | 2096 ± 222 | 2284 |

For each antigen, 5 doses of 100 µg were given monthly to each of 3 sheep and the serum analysed at 18 weeks. ELISA titres, derived from 14 week samples, represent serum dilutions (pool from 3 animals) which gave a signal of 0.5 $A_{450}$ above background and are the mean of duplicate determinations. For the crystal violet $ED_{50}$ assay, Toxin B was used at a fixed concentration of 2 ng/ml and Toxin A at 50 ng/ml.

TABLE 4

Neutralisation $ED_{50}$ titres against various Toxin B toxinotypes using serum antiserum generated to recombinant Toxin B (residues 767-1852)

| Immunising Antigen | Assay Toxinotype | Neutralising Potency $ED_{50}$ (µg/ml IgG) | | |
|---|---|---|---|---|
| | | 1 | 2 | Mean |
| Toxin B (residues 767-1852) | Toxin B (0) | 2.5 ± 0.22 | 2.1 ± 0.20 | 2.3 |
| | Toxin B (3) | 7.9 ± 0.64 | 7.5 ± 1.20 | 7.7 |
| | Toxin B (5) | 7.7 ± 0.73 | 8.1 ± 0.71 | 7.9 |
| | Toxin B (10) | 7.2 ± 0.67 | 9.0 ± 0.75 | 8.1 |

Antibodies to Toxin B (residues 767-1852) (toxinotype 0 sequence) were assessed for their capacity to neutralise other Toxin B toxinotypes. Purified Toxin B toxinotypes (0, 3, 5 and 10) were each titrated in the cell assay and used at a fixed concentration of 16× the minimum toxin concentration which causes cell death in a 24 hr incubation period. Neutralising potencies are expressed in µg/ml IgG required for 50% neutralisation of the above Toxin B concentration.

SED ID NOs

Clostridium difficile Toxin A (Toxinotype 0)

SEQ ID NO: 1

```
MSLISKEELIKLAYSIRPRENEYKTILTNLDEYNKLTTNNNENKYLQLKKLNESIDVFMNKYKTSSRNRALSNL
KKDILKEVILIKNSNTSPVEKNLHFVVVIGGEVSDIALEYIKQWADINAEYNIKLWYDSEAFLVNTLKKAIVES
STTEALQLLEEEIQNPQFDNMKFYKKRMEFIYDRQKRFINYYKSQINKPTVPTIDDIIKSHLVSEYNRDETVLE
SYRTNSLRKINSNHGIDIRANSLFTEQELLNIYSQELLNRGNLAAASDIVRLLALKNFGGVYLDVDMLPGIHSD
LFKTISRPSSIGLDRWEMIKLEAIMKYKKYINNYTSENFDKLDQQLKDNFKLIIESKSEKSEIFSKLENLNVSD
LEIKIAFALGSVINQALISKQGSYLTNLVIEQVKNRYQFLNQHLNPAIESDNNFTDTTKIFHDSLFNSATAENS
MFLTKIAPYLQVGFMPEARSTISLSGPGAYASAYYDFINLQENTIEKTLKASDLIEFKFPENNLSQLTEQEINS
LWSFDQASAKYQFEKYVRDYTGGSLSEDNGVDFNKNTALDKNYLLNNKIPSNNVEEAGSKNYVHYIIQLQGDDI
SYEATCNLFSKNPKNSIIIQRNMNESAKSYFLSDDGESILELNKYRIPERLKNKEKVKVTFIGHGKDEFNTSEF
ARLSVDSLSNEISSFLDTIKLDISPKNVEVNLLGCNMFSYDFNVEETYPGKLLLSIMDKITSTLPDVNKNSITI
```

| SEQ ID NOs |
|---|
| GANQYEVRINSEGRKELLAHSGKWINKEEAIMSDLSSKEYIFFDSIDNKLKAKSKNIPGLASISEDIKTLLLDA<br>SVSPDTKFILNNLKLNIESSIGDYIYYEKLEPVKNIIHNSIDDLIDEFNLLENVSDELYELKKLNNLDEKYLIS<br>FEDISKNNSTYSVRFINKSNGESVYVETEKEIFSKYSEHITKEISTIKNSIITDVNGNLLDNIQLDHTSQVNTL<br>NAAFFIQSLIDYSSNKDVLNDLSTSVKVQLYAQLFSTGLNTIYDSIQLVNLISNAVNDTINVLPTITEGIPIVS<br>TILDGINLGAAIKELLDEHDPLLKKELEAKVGVLAINMSLSIAATVASIVGIGAEVTIFLLPIAGISAGIPSLV<br>NNELILHDKATSVVNYFNHLSESKKYGPLKTEDDKILVPIDDLVISEIDFNNNSIKLGTCNILAMEGGSGHTVT<br>GNIDHFFSSPSISSHIPSLSIYSAIGIETENLDFSKKIMMLPNAPSRVFVWVETGAVPGLRSLENDGTRLLDSI<br>RDLYPGKFYWRFYAFFDYAITTLKPVYEDTNIKIKLDKDTRNFIMPTITTNEIRNKLSYSFDGAGGTYSLLLSS<br>YPISTNINLSKDDLWIFNIDNEVREISIENGTIKKGKLIKDVLSKIDINKNKLIIGNQTIDFSGDIDNKDRYIF<br>LTCELDDKISLIIEINLVAKSYSLLLSGDKNYLISNLSNTIEKINTLGLDSKNIAYNYTDESNNKYFGAISKTS<br>QKSIIHYKKDSKNILEFYNDSTLEFNSKDFIAEDINVFMKDDINTITGKYYVDNNTDKSIDFSISLVSKNQVKV<br>NGLYLNESVYSSYLDFVKNSDGHHNTSNFMNLFLDNISFWKLFGFENINFVIDKYFTLVGKTNLGYVEFICDNN<br>KNIDIYFGEWKTSSSKSTIFSGNGRNVVVEPIYNPDTGEDISTSLDFSYEPLYGIDRYINKVLIAPDLYTSLIN<br>INTNYYSNEYYPEIIVLNPNTFHKKVNINLDSSSFEYKWSTEGSDFILVRYLEESNKKILQKIRIKGILSNTQS<br>FNKMSIDFKDIKKLSLGYIMSNFKSFNSENELDRDHLGFKIIDNKTYYYDEDSKLVKGLININNSLFYFDPIEF<br>NLVTGWQTINGKKYYFDINTGAALTSYKIINGKHFYFNNDGVMQLGVFKGPDGFEYFAPANTQNNNIEGQAIVY<br>QSKFLTLNGKKYYFDNNSKAVTGWRIINNEKYYFNPNNAIAAVGLQVIDNNKYYFNPDTAIISKGWQTVNGSRY<br>YFDTDTAIAFNGYKTIDGKHFYFDSDCVVKIGVFSTSNGFEYFAPANTYNNNIEGQAIVYQSKFLTLNGKKYYF<br>DNNSKAVTGLQTIDSKKYYFNTNTAEAATGWQTIDGKKYYFNTNTAEAATGWQTIDGKKYYFNTNTAIASTGYT<br>IINGKHFYFNTDGIMQIGVFKGPNGFEYFAPANTDANNIEGQAILYQNEFLTLNGKKYYFGSDSKAVTGWRIIN<br>NKKYYFNPNNAIAAIHLCTINNDKYYFSYDGILQNGYITIERNNFYFDANNESKMVTGVFKGPNGFEYFAPANT<br>HNNNIEGQAIVYQNKFLTLNGKKYYFDNDSKAVTGWQTIDGKKYYFNLNTAEAATGWQTIDGKKYYFNLNTAEA<br>ATGWQTIDGKKYYFNTNTFIASTGYTSINGKHFYFNTDGIMQIGVFKGPNGFEYFAPANTDANNIEGQAILYQN<br>KPFLTLNGKKYYFGSDSKAVTGLRTIDGKKYYFNTNTAVAVTGWQTIDGKKYYFNTNTSIASTGYTIISGKHFY<br>NTDGIMQIGVFKGPDGFEYFAPANTDANNIEGQAIRYQNRFLYLHDNIYYFGNNSKAATGWVTIDGNRYYFEPN<br>TAMGANGYKTIDNKNFYFRNGLPQIGVFKGSNGFEYFAPANTDANNIEGQAIRYQNRFLHLLGKIYYFGNNSKA<br>VTGWQTINGKVYYFMPDTAMAAAGGLFEIDGVIYFFGVDGVKAPGIYG |

*C. difficile* Toxin B (Toxinotype 0)

SEQ ID NO: 2

MSLVNRKQLEKMANVRFRTQEDEYVAILDALEEYHNMSENTVVEKYLKLKDINSLTDIYIDTYKKSGRNKALKK
FKEYLVTEVLELKNNNLTPVEKNLHFVWIGGQINDTAINYINQWKDVNSDYNVNVFYDSNAFLINTLKKTVVES
AINDTLESFRENLNDPRFDYNKFFRKRMEIIYDKQKNFINYYKAQREENPELIIDDIVKTYLSNEYSKEIDELN
TYIEESLNKITQNSGNDVRNFEEFKNGESFNLYEQELVERWNLAAASDILRISALKEIGGMYLDVDMLPGIQPD
LFESIEKPSSVTVDFWEMTKLEAIMKYKEYIPEYTSEHFDMLDEEVQSSFESVLASKSDKSEIFSSLGDMEASP
LEVKIAFNSKGIINQGLISVKDSYCSNLIVKQIENRYKILNNSLNPAIEDDFNTTTNTFIDSIMAEANADNG
RFMMELGKYLRVGFFPDVKTTINLSGPEAYAAAYQDLLMFKEGSMNIHLIEADLRNFEISKTNISQSTEQEMAS
LWSFDDARAKAQFEEYKRNYFEGSLGEDDNLDFSQNIVVDKEYLLEKISSLARSSERGYIHYIVQLQGDKISYE
AACNLFAKTPYDSVLFQKNIEDSEIAYYYNPGDGEIQEIDKYKIPSIISDRPKIKLTFIGHGKDEFNTDIFAGF
DVDSLSTEIEAAIDLAKEDISPKSIEINLLGCNMFSYSINVEETYPGKLLLKVKDKISELMPSISQDSIIVSAN
QYEVRINSEGRRELLDHSGEWINKEESIIKDISSKEYISFNPKENKITVKSKNLPELSTLLQEIRNNSNSSDIE
LEEKVMLTECEINVISNIDTQIVEERIEEAKNLTSDSINYIKDEFKLIESISDALCDLKQQNELEDSHFISFED
ISETDEGFSIRFINKETGESIFVETEKTIFSEYANHITEEISKIKGTIFDTVNGKLVKKVNLDTTHEVNTLNAA
FFIQSLIEYNSSKESLSNLSVAMKVQVYAQLFSTGLNTITDAAKVVELVSTALDETIDLLPTLSEGLPIIATII
DGVSLGAAIKELSETSDPLLRQEIEAKIGIMAVNLTTATTAIITSSLGISAGFSILLVPLAGISAGIPSLVNNE
LVLRDKATKVVDYFKHVSLVETEGVFTLLDDDKIMMPQDDLVISEIDFNNNSIVLGKCEIWRMEGGSGHTVTDDI
DHFFSAPSITYREPHLSIYDVLEVQKEELDLSKDLMVLPNAPNRVFAWETGWTPGLRSLENDGTKLLDRIRDNY
EGEFYWRYFAFIADALITTLKPRYEDTNIRINLDSNTRSFIVPIITTEYIREKLSYSFYGSGGTYALSLSQYNM
GINIELSESDVWIIDVDNVVRDVTIESDKIKKGDLIEGILSTLSIEENKIILNSHEINFSGEVNGSNGFVSLTF
SILEGINAIIEVDLLSKSYKLLISGELKILMLNSNHIQQKIDYIGFNSELQKNIPYSFVDSEGKENGFINGSTK
EGLFVSELPDVVLISKVYMDDSKPSFGYYSNNLKDVKVITKDNVNILTGYYLKDDIKISLSLTLQDEKTIKLNS
VHLDESGVAEILKFMNRKGNTNTSDSLMSFLESMNIKSIFVNFLQSNIKFILDANFIISGTTSIGQFEFICDEN
DNIQPYFIKFNTLETNYTLYVGNRQNMIVEPNYDLDDSGDISYTVINFSQYKLYLGIDSCVNKVVISPNIYTDEI
NITPVYETNNTYPEVIVLDANYINEKINVNINDLSIRYVWSNDGNDFILMSTSEENKVSQVKIRFVNVFKDKTL
ANKLSPNFSDKQDVPVSEIILSFTPSYYEDGLIGYDLGLVSLYNEKFYINNFGMMVSGLIYINDSLYYFKPPVN
NLITGFVTVGDDKYYFNPINGGAASIGETIIDDKNYYFNQSGVLQTGVFSTEDGFKYFAPANTLDENLEGEAID
FTGKLIIDENIYYFDDNYRGAVEWKELDGEMHYFSPETGKAFKGLNGPQGKYYFNSDGVMQKGFVSINDNKHY
FDDSGVMKVGYTEIDGKHFYFAENGEMQIGVFNTEDGFKYFAHHNEDLGNEEGEEISYSGILNFNNKIYYFDDS
FTAVVGWKDLEDGSKYYFDEDTAEAYIGLSLINDGQYYFNDDGIMQVGFVTINDKVYFSDSGIIESGVQNIDD
NYFYIDDNGIVQIGVFDTSDGYKYFAPANTVNDNIYGQAVEYSGLVRVGEDVYYFGETYTIETGWIYDMENESD
KYYFNPETKKACKGINLIDDIKYYFDEKGIMRTGLISFENNNYYFNENGEMQFGYINIEDKMFYFGEDGVMQIG
VFNTPDGFKYFAHQNTLDENFEGESINYTGWLDLDEKRYYFTDEYIAATGSVIIDGEEYYFDPDTAQLVISE

*C. difficile* Toxin A (Toxinotype 3)

SEQ ID NO: 3

MSLISKEELIKLAYSIRPRENEYKTILTLNLDEYNKLTTNNNENKYLQLKKLNESIDVFMNKYKNSSRNRALSNL
KKDILKEVILIKNSNTSPVEKNLHFVWIGGEVSDIALEYIKQWADINAEYNIKLWYDSEAFLVNTLKKAIVESS
TTEALQLLEEEIQNPQFDNMKFYKKRMEFIYDRQKRFINYYKSQINKPTVPTIDDIIKSHLVSEYNRDETLLES
YRTNSLRKINSNHGIDIRANSLFTEQELLNIYSQELLNRGNLAAASDIVRLLALKNFGGVYLDVDMLPGIHSDL
FKTIPRPSSIGLDRWEMIKLEAIMKYKKYINNYTSENFDKLDQQLKDNFKLIIESKSEKSEIFSKLENLNVSDL
EIKIAFALGSVINQALISKQGSYLTNLVIEQVKNRYQFLNQHLNPAIESDNNFTDTTKIFHDSLFNSATAENSM
FLTKIAPYLQVGFMPEARSTISLSGPGAYASAYYDFINLQENTIEKTLKASDLIEFKFPENNLSQLTEQEINSL
WSFDQASAKYQFEKYVRDTGGSLSEDNGVDFNKNTALDKNYLLNNKIPSNNVEEAGSKNYVHYIIQLQGDDIS
YEATCNLFSKNPKNSIIQRNMNESAKSYFLSDDGESILELNKYRIPERLKNKEKVKVTFIGHGKDEFNTSEFA
RLSVDSLSNEISSFLDTIKLDISPKNVEVNLLGCNMFSYDFNVEETYPGKLLLSIMDKITSTLPDVNKDSITIG
ANQYEVRINSEGRKELLAHSGKWINKEEAIMSDLSSKEYIFFDSIDNKLKAKSKNIPGLASISEDIKTLLLDAS
VSPDTKFILNNLKLNIESSIGDYIYYEKLEPVKNIIHNSIDDLIDEFNLLENVSDELYELKKLNNLDEKYLISF

| SED ID NOs |
| --- |
| EDISKNNSTYSVRFINKSNGESVYVETEKEIFSKYSEHITKEISTIKNSIITDVNGNLLDNIQLDHTSQVNTLN<br>AAFFIQSLIDYSSNKDVLNDLSTSVKVQLYAQLFSTGLNTIYDSIQLVNLISNAVNDTINVLPTITEGIPIVST<br>ILDGINLGAAIKELLDEHDPLLKKELEAKVGVLAINMSLSIAATVASIVGIGAEVTIFLLPIAGISAGIPSLVN<br>NELILHDKATSVVNYFNHLSESKEYGPLKTEDDKILVPIDDLVISEIDFNNNSIKLGTCNILAMEGGSGHTVTG<br>NIDHFFSSPYISSHIPSLSVYSAIGIKTENLDFSKKIMMLPNAPSRVFVWVETGAVPGLRSLENNGTKLLDSIR<br>DLYPGKFYWRFYAFFDYAITTLKPVYEDTNTKIKLDKDTRNFIMPTITTDEIRNKLSYSFDGAGGTYSLLLSSY<br>PISMNINLSKDDLWIFNIDNEVREISIENGTIKKGNLIEDVLSKIDINKNKLIIGNQTIDFSGDIDNKDRYIFL<br>TCELDDKISLIIEINLVAKSYSLLLSGDKNYLISNLSNTIEKINTLGLDSKNIAYNYTDESNNKYFGAISKTSQ<br>KSIIHYKKDSKNILEFYNGSTLEFNSKDFIAEDINVFMKDDINTITGKYYVDNNTDKSIDFSISLVSKNQVKVN<br>GLYLNESVYSSYLDFVKNSDGHHNTSNFMNLFLNNISFWKLFGFENINFVIDKYFTLVGKTNLGYVEFICDNNK<br>NIDIYFGEWKTSSSKSTIFSGNGRNVVVEPIYNPDTGEDISTSLDFSYEPLYGIDRYINKVLIAPDLYTSLINI<br>NTNYYSNEYYPEIIVLNPNTFHKKVNINLDSSSFEYKWSTEGSDFILVRYLEESNKKILQKIRIKGILSNTQSF<br>NKMSIDFKDIKKLSLGYIMSNFKSFNSENELDRDHLGFKIIDNKTYYDEDSKLVKGLININNSLFYDPIESN<br>LVTGWQTINGKKYYFDINTGAASTSYKIINGKHFYFNNNGVMQLGVFKGPDGFEYFAPANTQNNNIEGQAIVYQ<br>SKFLTLNGKKYYFDNDSKAVTGWRIINNEKYYFNPNNAIAAVGLQVIDNNKYYFNPDTAIISKGWQTVNGSRYY<br>FDTDTAIAFNGYKTIDGKHFYFDSDCVVKIGVFSGSNGFEYFAPANTYNNNIEGQAIVYQSKFLTLNGKKYYFD<br>NNSKAVTGWQTIDSKKYYFNTNTAEAATGWQTIDGKKYYFNTNTAEAATGWQTIDGKKYYFNTNTSIASTGYTI<br>INGKYFYFNTDGIMQIGVFKVPNGFEYFAPANTHNNNIEGQAILYQNKFLTLNGKKYYFGSDSKAITGWQTIDG<br>KKYYFNPNNAIAATHLCTINNDKYYFSYDGILQNGYITIERNNFYFDANNESKMVTGVFKGPNGFEYFAPANTH<br>NNNIEGQAIVYQNKFLTLNGKKYYFDNDSKAVTGWQTIDSKKYYFNLNTAVAVTGWQTIDGEKYYFNLNTAEAA<br>TGWQTIDGKRYYFNTNTYIASTGYTIINGKHFYFNTDGIMQIGVFKGPDGFEYFAPANTHNNNIEGQAILYQNK<br>FLTLNGKKYYFGSDSKAVTGLRTIDGKKYYFNTNTAVAVTGWQTINGKKYYFNTNTYIASTGYTIISGKHFYFN<br>TDGIMQIGVFKGPDGFEYFAPANTDANNIEGQAIRYQNRFLYLHDNIYYFGNDSKAATGWATIDGNRYYFEPNT<br>AMGANGYKTIDNKNFYFRNGLPQIGVFKGPNGFEYFAPANTDANNIDGQAIRYQNRFLHLLGKIYYFGNNSKAV<br>TGWQTINSKVYYFMPDTAMAAAGGLFEIDGVIYFFGVDGVKAPGIYG |

*C. difficile* Toxin B (Toxinotype 3)

SEQ ID NO: 4

| |
| --- |
| MSLVNRKQLEKMANVRFRVQEDEYVAILDALEEYHNMSENTVVEKYLKLKDINSLTDIYIDTYKKSGRNKALKK<br>FKEYLVTEVLELKNNNLTPVEKNLHFVWIGGQINDTAINYINQWKDVNSDYNVNVFYDSNAFLINTLKKTIVES<br>ATNDTLESFRENLNDPRFDYNKFYRKRMEIIYDKQKNFINYYKTQREENPDLIIDDIVKIYLSNEYSKDIDELN<br>SYIEESLNKVTENSGNDVRNFEEFKGGESFKLYEQELVERWNLAAASDILRISALKEVGYVLDVDMLPGIQPD<br>LFESIEKPSSVTVDFWEMVKLEAIMKYKEYIPGYTSEHFDMLDEEVQSSFESVLASKSDKSEIFSSLGDMEASP<br>LEVKIAFNSKGIINQGLISVKDSYCSNLIVKQIENRYKILNNSLNPAISEDNDFNTTTNAFIDSIMAEANADNG<br>RFMMELGKYLRVGFFPDVKTTINLSGPEAYAAAYQDLLMFKEGSMNIHLIEADLRNFEISKTNISQSTEQEMAS<br>LWSFDDARAKAQFEEYKKNYFEGSLGEDDNLDFSQNTVVDKEYLLEKISSLARSSERGYIHYIVQLQGDKISYE<br>AACNLFAKTPYDSVLFQKNIEDSEIAYYYNPGDGEIQEIDKYKIPSIISDRPKIKLTFIGHGKDEFNTDIFAGL<br>DVDSLSTEIETAIDLAKEDISPKSIEINLLGCNMFSYSVNVEETYPGKLLLRVKDKVSELMPSISQDSIIVSAN<br>QYEVRINSEGRRELLDHSGEWINKEESIIKDISSKEYISFNPKENKIIVKSKNLPELSTLLQEIRNNSNSSDIE<br>LEEKVMLAECEINVISNIDTQVVEGRIEEAKSLTSDSINYIKNEFKLIESISDALYDLKQQNELEESHFISFED<br>ILETDEGFSIRFIDKETGESIFVETEKAIFSEYANHITEEISKIKGTIFDTVRGLKVKKVNLDATHEVNTLNAA<br>FFIQSLIEYNSSKESLSNLSVAMKVQVYAQLFSTGLNTITDAAKVVELVSTALDETIDLLPTLSEGLPVIATII<br>DGVSLGAAIKELSETSDPLLRQEIEAKIGIMAVNLTAATTAIITSSLGIASGFSILLVPLAGISAGIPSLVNNE<br>LILRDKATKVVDYFSHISLAESEGAFTSLDDKIMMPQDDLVISEIDFNNNSITLGKCEIWRMEGGSGHTVTDDI<br>DHFFSAPSITYREPHLSIYDVLEVQKEELDLSKDLMVLPNAPNRVFAWETGWTPGLRSLENDGTKLLDRIRDNY<br>EGEFYWRYFAFIADALITTLKPRYEDTNIRINLDSNTRSFIVPVITTEYIREKLSYSFYGSGGTYALSLSQYNM<br>NINIELNENDTWVIDVDNVVRDVTIESDKIKKGDLIENILSKLSIEDNKIILDNHEINFSGTLNGGNGFVSLTF<br>SILEGINAVIEVDLLSKSYKVLISGELKTLMANSNSVQQKIDYIGLNSELQKNIPYSFMDDKGKENGFINCSTK<br>EGLFVSELSDVVLISKVYMDNSKPLFGYCSNDLKDVKVITKDDVIILTGYYLKDDIKISLSFTIQDENTIKLNG<br>VYLDENGVAEILKFMNKKGSTNTSDSLMSFLESMNIKSIFINSLQSNTKLILDTNFIISGTTSIGQFEFICDKD<br>NNIQPYFIKFNTLETKYTLYVGNRQNMIVEPNYDLDDSGDISSTVINFSQKYLYGIDSCVNKVIISPNIYTDEI<br>NITPIYEANNTYPEVIVLDTNYISEKINININDLSIRYVWSNDGSDFILMSTDEENKVSQVKIRFTNVFKGNTI<br>SDKISFNFSDKQDVSINKVISTFTPSYYVEGLLNYDLGLISLYNEKFYINNFGMMVSGLVYTINNEVFYSDSLYYFKPPIK<br>NLITGFTTIGDDKYYFNPDNGGAASVGETIIDGKNYYFSQNGVLQTGVFSTEDGFKYFAPADTLDENLEGEAID<br>FTGKLTIDENVYYFGDNYRAAIEWQTLDDEVYYFSTDTGRAFKGLNQIGDDKFYFNSDGIMQKGFVNINDKTFY<br>FDDSGVMKSGYTEIDGKYFYFAENGEMQIGVFNTADGFKYFAHHDEDLGNEEGEALSYSGILNFNNKIYYFDDS<br>FTAVVGWKDLEDGSKYYFDEDTAEAYIGISIINDGKYYFNDSGIMQIGFVTINNEVFYFSDSGIVESGMQNIDD<br>NYFYIDENGLVQIGVFDTSDGYKYFAPANTVNDNIYGQAVEYSGLVRVGEDVYYFGETYTIETGWIYDMENESD<br>KYYFDPETKKAYKGINVIDDIKYYFDENGIMRTGLITFEDNHYYFNEDGIMQYGYLNIEDKTFYFSEDGIMQIG<br>VFNTPDGFKYFAHQNTLDENFEGESINYTGWLDLDEKRYYFTDEYIAATGSVIIDGEEYYFDPDTAQLVISE |

*C. difficile* Toxin A 542-1850 (toxinotype 0)

SEQ ID NO: 5

| |
| --- |
| LSEDNGVDFNKNTALDKNYLLNNKIPSNNVEEAGSKNYVHYIIQLQGDDISYEATCNLFSKNPKNSIIIQRNMN<br>ESAKSYFLSDDGESILELNKYRIPERLKNKEKVKVTFIGHGKDEFNTSEFARLSVDSLSNEISSFLDTIKLDIS<br>PKNVEVNLLGCNMFSYDFNVEETYPGKLLLSIMDKITSTLPDVKNKSITIGANQYEVRINSEGRKELLAHSGKW<br>INKEEAIMSDLSSKEYIFFDSIDNKLKAKSKNIPGLASISEDIKTLLLDASVSPDTKFILNNLKLNIESSIGDY<br>IYYEKLEPVKNIIHNSIDDLIDEFNLLENVSDELYELKKLNNLDEKYLISFEDISKNNSTYSVRFINKSNGESV<br>YVETEKEIFSKYSEHITKEISTIKNSIITDVNGNLLDNIQLDHTSQVNTLNAAFFIQSLIDYSSNKDVLNDLST<br>SVKVQLYAQLFSTGLNTIYDSIQLVNLISNAVNDTINVLPTITEGIPIVSTILDGINLGAAIKELLDEHDPLLK<br>KELEAKVGVLAINMSLSIAATVASIVGIGAEVTIFLLPIAGISAGIPSLVNNELILHDKATSVVNYFNHLSESK<br>KYGPLKTEDDKILVPIDDLVISEIDFNNNSIKLGTCNILAMEGGSGHTVTGNIDHFFSSPSISSHIPSLSIYSA<br>IGIETENLDFSKKIMMLPNAPSRVFVWVETGAVPGLRSLENDGTRLLDSIRDLYPGKFYWRFYAFFDYAITTLK<br>PVYEDTNIKIKLDKDTRNFIMPTITTNEIRNKLSYSFDGAGGTYSLLLSSYPISTNINLSKDDLWIFNIDNEVR<br>EISIENGTIKKGKLIKDVLSKIDINKNKLIIGNQTIDFSGDIDNKDRYIFLTCELDDKISLIIEINLVAKSYSL<br>LLSGDKNYLISNLSNTIEKINTLGLDSKNIAYNYTDESNNKYFGAISKTSQKSIIHYKKDSKNILEFYNDSTLE<br>FNSKDFIAEDINVFMKDDINTITGKYYVDNNTDKSIDFSISLVSKNQVKVNGLYLNESVYSSYLDFVKNSDGHH |

| SED ID NOs |
|---|
| NTSNFMNLFLDNISFWKLFGFENINFVIDKYFTLVGKTNLGYVEFICDNNKNIDIYFGEWKTSSSKSTIFSGNG<br>RNVVVEPIYNPDTGEDISTSLDFSYEPLYGIDRYINKVLIAPDLYTSLININTNYYSNEYYPEIIVLNPNTFHK<br>KVNINLDSSSFEYKWSTEGSDFILVRYLEESNKKILQKIRIKGILSNTQSFNKMSIDFKDIKKLSLGYIMSNFK<br>SFNSENELDRDHLGFKIIDNKTYYYDEDSKLVKGLININNSLFYFDPIEFNL |

*C. difficile* Toxin A 542-1850 (toxinotype 3)

SEQ ID NO: 6

LSEDNGVDFNKNTALDKNYLLNNKIPSNNVEEAGSKNYVHYIIQLQGDDISYEATCNLFSKNPKNSIIIQRNMN
ESAKSYFLSDDGESILELNKYRIPERLKNKEKVKVTFIGHGKDEFNTSEFARLSVDSLSNEISSFLDTIKLDIS
PKNVEVNLLGCNMFSYDFNVEETYPGKLLLSIMDKITSTLPDVNKDSITIGANQYEVRINSEGRKELLAHSGKW
INKEEAIMSDLSSKEYIFFDSIDNKLKAKSKNIPGLASISEDIKTLLLDASVSPDTKFILNNLKLNIESSIGDY
IYYEKLEPVKNIIHNSIDDLIDEFNLLENVSDELYELKKLNNLDEKYLISFEDISKNNSTYSVRFINKSNGESV
YVETEKEIFSKYSEHITKEISTIKNSIITDVNGNLLDNIQLDHTSQVNTLNAAFFIQSLIDYSSNKDVLNDLST
SVKVQLYAQLFSTGLNTIYDSIQLVNLISNAVNDTINVLPTITEGIPIVSTILDGINLGAAIKELLDEHDPLLK
KELEAKVGVLAINMSLSIAATVASIVGIGAEVTIFLLPIAGISAGIPSLVNNELILHDKATSVVNYFNHLSESK
EYGPLKTEDDKILVPIDDLVISEIDFNNNSIKLGTCNILAMEGGSGHTVTGNIDHFFSSPYISSHIPSLSVYSA
IGIKTENLDFSKKIMMLPNAPSRVFVWVETGAVPGLRSLENNGTKLLDSIRDLYPGKFYWRFYAFFDYAITTLK
PVYEDTNTKIKLDKDTRNFIMPTITTDEIRNKLSYSFDGAGGTYSLLLSSYPISMNINLSKDDLWIFNIDNEVR
EISIENGTIKKGNLIEDVLSKIDINKNKLIIGNQTIDFSGDIDNKDRYIFLTCELDDKISLIIEINLVAKSYSL
LLSGDKNYLISNLSNTIEKINTLGLDSKNIAYNYTDESNNKYFGAISKTSQKSIIHYKKDSKNILEFYNGSTLE
FNSKDFIAEDINVFMKDDINTITGKYYVDNNTDKSIDFSISLVSKNQVKVNGLYLNESVYSSYLDFVKNSDGHH
NTSNFMNLFLNNISFWKLFGFENINFVIDKYFTLVGKTNLGYVEFICDNNKNIDIYFGEWKTSSSKSTIFSGNG
RNVVVEPIYNPDTGEDISTSLDFSYEPLYGIDRYINKVLIAPDLYTSLININTNYYSNEYYPEIIVLNPNTFHK
KVNINLDSSSFEYKWSTEGSDFILVRYLEESNKKILQKIRIKGILSNTQSFNKMSIDFKDIKKLSLGYIMSNFK
SFNSENELDRDHLGFKIIDNKTYYYDEDSKLVKGLININNSLFYFDPIESNL

*C. difficile* Toxin A 542-1850 (toxinotype 0) Cysteine protease negative

SEQ ID NO: 7

LSEDNGVDFNKNTALDKNYLLNNKIPSNNVEEAGSKNYVHYIIQLQGDDISYEATCNLFSKNPKNSIIIQRNMN
ESAKSYFLSDDGESILELNKYRIPERLKNKEKVKVTFIGHGKDEFNTSEFARLSVDSLSNEISSFLDTIKLDIS
PKNVEVNLLGANMFSYDFNVEETYPGKLLLSIMDKITSTLPDVNKNSITIGANQYEVRINSEGRKELLAHSGKW
INKEEAIMSDLSSKEYIFFDSIDNKLKAKSKNIPGLASISEDIKTLLLDASVSPDTKFILNNLKLNIESSIGDY
IYYEKLEPVKNIIHNSIDDLIDEFNLLENVSDELYELKKLNNLDEKYLISFEDISKNNSTYSVRFINKSNGESV
YVETEKEIFSKYSEHITKEISTIKNSIITDVNGNLLDNIQLDHTSQVNTLNAAFFIQSLIDYSSNKDVLNDLST
SVKVQLYAQLFSTGLNTIYDSIQLVNLISNAVNDTINVLPTITEGIPIVSTILDGINLGAAIKELLDEHDPLLK
KELEAKVGVLAINMSLSIAATVASIVGIGAEVTIFLLPIAGISAGIPSLVNNELILHDKATSVVNYFNHLSESK
KYGPLKTEDDKILVPIDDLVISEIDFNNNSIKLGTCNILAMEGGSGHTVTGNIDHFFSSPSISSHIPSLSIYSA
IGIETENLDFSKKIMMLPNAPSRVFVWVETGAVPGLRSLENDGTRLLDSIRDLYPGKFYWRFYAFFDYAITTLK
PVYEDTNIKIKLDKDTRNFIMPTITTNEIRNKLSYSFDGAGGTYSLLLSSYPISTNINLSKDDLWIFNIDNEVR
EISIENGTIKKGKLIKDVLSKIDINKNKLIIGNQTIDFSGDIDNKDRYIFLTCELDDKISLIIEINLVAKSYSL
LLSGDKNYLISNLSNTIEKINTLGLDSKNIAYNYTDESNNKYFGAISKTSQKSIIHYKKDSKNILEFYNDSTLE
FNSKDFIAEDINVFMKDDINTITGKYYVDNNTDKSIDFSISLVSKNQVKVNGLYLNESVYSSYLDFVKNSDGHH
NTSNFMNLFLDNISFWKLFGFENINFVIDKYFTLVGKTNLGYVEFICDNNKNIDIYFGEWKTSSSKSTIFSGNG
RNVVVEPIYNPDTGEDISTSLDFSYEPLYGIDRYINKVLIAPDLYTSLININTNYYSNEYYPEIIVLNPNTFHK
KVNINLDSSSFEYKWSTEGSDFILVRYLEESNKKILQKIRIKGILSNTQSFNKMSIDFKDIKKLSLGYIMSNFK
SFNSENELDRDHLGFKIIDNKTYYYDEDSKLVKGLININNSLFYFDPIEFNL

*C. difficile* Toxin A 770-1850

SEQ ID NO: 8

MSDLSSKEYIFFDSIDNKLKAKSKNIPGLASISEDIKTLLLDASVSPDTKFILNNLKLNIESSIGDYIYYEKLE
PVKNIIHNSIDDLIDEFNLLENVSDELYELKKLNNLDEKYLISFEDISKNNSTYSVRFINKSNGESVYVETEKE
IFSKYSEHITKEISTIKNSIITDVNGNLLDNIQLDHTSQVNTLNAAFFIQSLIDYSSNKDVLNDLSTSVKVQLY
AQLFSTGLNTIYDSIQLVNLISNAVNDTINVLPTITEGIPIVSTILDGINLGAAIKELLDEHDPLLKKELEAKV
GVLAINMSLSIAATVASIVGIGAEVTIFLLPIAGISAGIPSLVNNELILHDKATSVVNYFNHLSESKKYGPLKT
EDDKILVPIDDLVISEIDFNNNSIKLGTCNILAMEGGSGHTVTGNIDHFFSSPSISSHIPSLSIYSAIGIETEN
LDFSKKIMMLPNAPSRVFVWVETGAVPGLRSLENDGTRLLDSIRDLYPGKFYWRFYAFFDYAITTLKPVYEDTN
IKIKLDKDTRNFIMPTITTNEIRNKLSYSFDGAGGTYSLLLSSYPISTNINLSKDDLWIFNIDNEVREISIENG
TIKKGKLIKDVLSKIDINKNKLIIGNQTIDFSGDIDNKDRYIFLTCELDDKISLIIEINLVAKSYSLLLSGDKN
YLISNLSNTIEKINTLGLDSKNIAYNYTDESNNKYFGAISKTSQKSIIHYKKDSKNILEFYNDSTLEFNSKDFI
AEDINVFMKDDINTITGKYYVDNNTDKSIDFSISLVSKNQVKVNGLYLNESVYSSYLDFVKNSDGHHNTSNFMN
LFLDNISFWKLFGFENINFVIDKYFTLVGKTNLGYVEFICDNNKNIDIYFGEWKTSSSKSTIFSGNGRNVVVEP
IYNPDTGEDISTSLDFSYEPLYGIDRYINKVLIAPDLYTSLININTNYYSNEYYPEIIVLNPNTFHKKVNINLD
SSSFEYKWSTEGSDFILVRYLEESNKKILQKIRIKGILSNTQSFNKMSIDFKDIKKLSLGYIMSNFKSFNSENE
LDRDHLGFKIIDNKTYYYDEDSKLVKGLININNSLFYFDPIEFNL

*C. difficile* Toxin A 1130-1850

SEQ ID NO: 9

SESKKYGPLKTEDDKILVPIDDLVISEIDFNNNSIKLGTCNILAMEGGSGHTVTGNIDHFFSSPSISSHIPSLS
IYSAIGIETENLDFSKKIMMLPNAPSRVFVWVETGAVPGLRSLENDGTRLLDSIRDLYPGKFYWRFYAFFDYAI
TTLKPVYEDTNIKIKLDKDTRNFIMPTITTNEIRNKLSYSFDGAGGTYSLLLSSYPISTNINLSKDDLWIFNID
NEVREISIENGTIKKGKLIKDVLSKIDINKNKLIIGNQTIDFSGDIDNKDRYIFLTCELDDKISLIIEINLVAK
SYSLLLSGDKNYLISNLSNTIEKINTLGLDSKNIAYNYTDESNNKYFGAISKTSQKSIIHYKKDSKNILEFYND
STLEFNSKDFIAEDINVFMKDDINTITGKYYVDNNTDKSIDFSISLVSKNQVKVNGLYLNESVYSSYLDFVKNS
DGHHNTSNFMNLFLDNISFWKLFGFENINFVIDKYFTLVGKTNLGYVEFICDNNKNIDIYFGEWKTSSSKSTIF
SGNGRNVVVEPIYNPDTGEDISTSLDFSYEPLYGIDRYINKVLIAPDLYTSLININTNYYSNEYYPEIIVLNPN
TFHKKVNINLDSSSFEYKWSTEGSDFILVRYLEESNKKILQKIRIKGILSNTQSFNKMSIDFKDIKKLSLGYIM
SNFKSFNSENELDRDHLGFKIIDNKTYYYDEDSKLVKGLININNSLFYFDPIEFNL

-continued

SEQ ID NOs

*C. difficile* Toxin B (toxinotype 0) 543-1852

SEQ ID NO: 10

```
LGEDDNLDFSQNIVVDKEYLLEKISSLARSSERGYIHYIVQLQGDKISYEAACNLFAKTPYDSVLFQKNIEDSE
IAYYYNPGDGEIQEIDKYKIPSIISDRPKIKLTFIGHGKDEFNTDIFAGFDVDSLSTEIEAAIDLAKEDISPKS
IEINLLGCNMFSYSINVEETYPGKLLLKVKDKISELMPSISQDSIIVSANQYEVRINSEGRRELLDHSGEWINK
EESIIKDISSKEYISFNPKENKITVKSKNLPELSTLLQEIRNNSNSSDIELEEKVMLTECEINVISNIDTQIVE
ERIEEAKNLTSDSINYIKDEFKLIESISDALCDLKQQNELEDSHFISFEDISETDEGFSIRFINKETGESIFVE
TEKTIFSEYANHITEEISKIKGTIFDTVNGKLVKKVNLDTTHEVNTLNAAFFIQSLIEYNSSKESLSNLSVAMK
VQVYAQLFSTGLNTITDAAKVVELVSTALDETIDLLPTLSEGLPIIATIIDGVSLGAAIKELSETSDPLLRQEI
EAKIGIMAVNLTTATTAIITSSLGIASGFSILLVPLAGISAGIPSLVNNELVLRDKATKVVDYFKHVSLVETEG
VFTLLDDKIMMPQDDLVISEIDFNNNSIVLGKCEIWRMEGGSGHTVTDDIDHFFSAPSITYREPHLSIYDVLEV
QKEELDLSKDLMVLPNAPNRVFAWETGWTPGLRSLENDGTKLLDRIRDNYEGEFYWRYFAFIADALITTLKPRY
EDTNIRINLDSNTRSFIVPIITTEYIREKLSYSFYGSGGTYALSLSQYNMGINIELSESDVWIIDVDNVVRDVT
IESDKIKKGDLIEGILSTLSIEENKIILNSHEINFSGEVNGSNGFVSLTFSILEGINAIIEVDLLSKSYKLLIS
GELKILMLNSNHIQQKIDYIGFNSELQKNIPYSFVDSEGKENGFINGSTKEGLFVSELPDVVLISKVYMDDSKP
SFGYYSNNLKDVKVITKDNVNILTGYYLKDDIKISLSLTLQDEKTIKLNSVHLDESGVAEILKFMNRKGNTNTS
DSLMSFLESMNIKSIFVNFLQSNIKFILDANFIISGTTSIGQFEFICDENDNIQPYFIKFNTLETNYTLYVGNR
QNMIVEPNYDLDDSGDISSTVINFSQKYLYGIDSCVNKVVISPNIYTDEINITPVYETNNTYPEVIVLDANYIN
EKINVNINDLSIRYVWSNDGNDFILMSTEEENKVSQVKIRFVNVFKDKTLANKLSFNFSDKQDVPVSEIILSFT
PSYYEDGLIGYDLGLVSLYNEKFYINNFGMMVSGLIYINDSLYYFKPPVNNL
```

*C. difficile* Toxin B (toxinotype 3) 543-1852

SEQ ID NO: 11

```
LGEDDNLDFSQNTVVDKEYLLEKISSLARSSERGYIHYIVQLQGDKISYEAACNLFAKTPYDSVLFQKNIEDSE
IAYYYNPGDGEIQEIDKYKIPSIISDRPKIKLTFIGHGKDEFNTDIFAGLDVDSLSTEIETAIDLAKEDISPKS
IEINLLGCNMFSYSVNVEETYPGKLLLRVKDKVSELMPSISQDSIIVSANQYEVRINSEGRRELLDHSGEWINK
EESIIKDISSKEYISFNPKENKIIVKSKNLPELSTLLQEIRNNSNSSDIELEEKVMLAECEINVISNIDTQVVE
GRIEEAKSLTSDSINYIKNEFKLIESISDALYDLKQQNELEESHFISFEDILETDEGFSIRFIDKETGESIFVE
TEKAIFSEYANHITEEISKIKGTIFDTVNGKLVKKVNLDATHEVNTLNAAFFIQSLIEYNSSKESLSNLSVAMK
VQVYAQLFSTGLNTITDAAKVVELVSTALDETIDLLPTLSEGLPVIATIIDGVSLGAAIKELSETSDPLLRQEI
EAKIGIMAVNLTAATTAIITSSLGIASGFSILLVPLAGISAGIPSLVNNELVLRDKATKVVDYFSHISLAESEG
AFTSLDDKIMMPQDDLVISEIDFNNNSITLGKCEIWRMEGGSGHTVTDDIDHFFSAPSITYREPHLSIYDVLEV
QKEELDLSKDLMVLPNAPNRVFAWETGWTPGLRSLENDGTKLLDRIRDNYEGEFYWRYFAFIADALITTLKPRY
EDTNIRINLDSNTRSFIVPVITTEYIREKLSYSFYGSGGTYALSLSQYNMNINIELNENDTWVIDVDNVVRDVT
IESDKIKKGDLIENILSKLSIEDNKIILDNHEINFSGTLNGGNGFVSLTFSILEGINAIIEVDLLSKSYKLLIS
GELKTLMANSNSVQQKIDYIGLNSELQKNIPYSFMDDKGKENGFINCSTKEGLFVSELSDVVLISKVYMDNSKP
LFGYCSNDLKDVKVITKDDVIILTGYYLKDDIKISLSFTIQDENTIKLNGVYLDENGVAEILKFMNKKGSTNTS
DSLMSFLESMNIKSIFINSLQSNTKLILDTNFIISGTTSIGQFEFICDKDNNIQPYFIKFNTLETKYTLYVGNR
QNMIVEPNYDLDDSGDISSTVINFSQKYLYGIDSCVNKVIISPNIYTDEINITPIYEANNTYPEVIVLDTNYIS
EKINININDLSIRYVWSNDGSDFILMSTDEENKVSQVKIRFTNVFKGNTISDKISFNFSDKQDVSINKVISTFT
PSYVEGLLNYDLGLISLYNEKFYINNFGMMVSGLVYINDSLYYFKPPIKNL
```

*C. difficile* Toxin B 543-1852 Cysteine protease negative

SEQ ID NO: 12

```
LGEDDNLDFSQNIVVDKEYLLEKISSLARSSERGYIHYIVQLQGDKISYEAACNLFAKTPYDSVLFQKNIEDSE
IAYYYNPGDGEIQEIDKYKIPSIISDRPKIKLTFIGHGKDEFNTDIFAGFDVDSLSTEIEAAIDLAKEDISPKS
IEINLLGANMFSYSINVEETYPGKLLLKVKDKISELMPSISQDSIIVSANQYEVRINSEGRRELLDHSGEWINK
EESIIKDISSKEYISFNPKENKITVKSKNLPELSTLLQEIRNNSNSSDIELEEKVMLTECEINVISNIDTQIVE
ERIEEAKNLTSDSINYIKDEFKLIESISDALCDLKQQNELEDSHFISFEDISETDEGFSIRFINKETGESIFVE
TEKTIFSEYANHITEEISKIKGTIFDTVNGKLVKKVNLDTTHEVNTLNAAFFIQSLIEYNSSKESLSNLSVAMK
VQVYAQLFSTGLNTITDAAKVVELVSTALDETIDLLPTLSEGLPIIATIIDGVSLGAAIKELSETSDPLLRQEI
EAKIGIMAVNLTTATTAIITSSLGIASGFSILLVPLAGISAGIPSLVNNELVLRDKATKVVDYFKHVSLVETEG
VFTLLDDKIMMPQDDLVISEIDFNNNSIVLGKCEIWRMEGGSGHTVTDDIDHFFSAPSITYREPHLSIYDVLEV
QKEELDLSKDLMVLPNAPNRVFAWETGWTPGLRSLENDGTKLLDRIRDNYEGEFYWRYFAFIADALITTLKPRY
EDTNIRINLDSNTRSFIVPIITTEYIREKLSYSFYGSGGTYALSLSQYNMGINIELSESDVWIIDVDNVVRDVT
IESDKIKKGDLIEGILSTLSIEENKIILNSHEINFSGEVNGSNGFVSLTFSILEGINAIIEVDLLSKSYKLLIS
GELKILMLNSNHIQQKIDYIGFNSELQKNIPYSFVDSEGKENGFINGSTKEGLFVSELPDVVLISKVYMDDSKP
SFGYYSNNLKDVKVITKDNVNILTGYYLKDDIKISLSLTLQDEKTIKLNSVHLDESGVAEILKFMNRKGNTNTS
DSLMSFLESMNIKSIFVNFLQSNIKFILDANFIISGTTSIGQFEFICDENDNIQPYFIKFNTLETNYTLYVGNR
QNMIVEPNYDLDDSGDISSTVINFSQKYLYGIDSCVNKVVISPNIYTDEINITPVYETNNTYPEVIVLDANYIN
EKINVNINDLSIRYVWSNDGNDFILMSTEEENKVSQVKIRFVNVFKDKTLANKLSFNFSDKQDVPVSEIILSFT
PSYYEDGLIGYDLGLVSLYNEKFYINNFGMMVSGLIYINDSLYYFKPPVNNL
```

*C. difficile* Toxin B 767-1852

SEQ ID NO: 13

```
SIIKDISSKEYISFNPKENKITVKSKNLPELSTLLQEIRNNSNSSDIELEEKVMLTECEINVISNIDTQIVEER
IEEAKNLTSDSINYIKDEFKLIESISDALCDLKQQNELEDSHFISFEDISETDEGFSIRFINKETGESIFVETE
KTIFSEYANHITEEISKIKGTIFDTVNGKLVKKVNLDTTHEVNTLNAAFFIQSLIEYNSSKESLSNLSVAMKVQ
VYAQLFSTGLNTITDAAKVVELVSTALDETIDLLPTLSEGLPIIATIIDGVSLGAAIKELSETSDPLLRQEIEA
KIGIMAVNLTTATTAIITSSLGIASGFSILLVPLAGISAGIPSLVNNELVLRDKATKVVDYFKHVSLVETEGVF
TLLDDKIMMPQDDLVISEIDFNNNSIVLGKCEIWRMEGGSGHTVTDDIDHFFSAPSITYREPHLSIYDVLEVQK
EELDLSKDLMVLPNAPNRVFAWETGWTPGLRSLENDGTKLLDRIRDNYEGEFYWRYFAFIADALITTLKPRYED
TNIRINLDSNTRSFIVPIITTEYIREKLSYSFYGSGGTYALSLSQYNMGINIELSESDVWIIDVDNVVRDVTIE
SDKIKKGDLIEGILSTLSIEENKIILNSHEINFSGEVNGSNGFVSLTFSILEGINAIIEVDLLSKSYKLLISGE
LKILMLNSNHIQQKIDYIGFNSELQKNIPYSFVDSEGKENGFINGSTKEGLFVSELPDVVLISKVYMDDSKPSF
GYYSNNLKDVKVITKDNVNILTGYYLKDDIKISLSLTLQDEKTIKLNSVHLDESGVAEILKFMNRKGNTNTSDS
```

| SED ID NOs |
| --- |

LMSFLESMNIKSIFVNFLQSNIKFILDANFIISGTTSIGQFEFICDENDNIQPYFIKFNTLETNYTLYVGNRQN
MIVEPNYDLDDSGDISSTVINFSQKYLYGIDSCVNKVVISPNIYTDEINITPVYETNNTYPEVIVLDANYINEK
INVNINDLSIRYVWSNDGNDFILMSTSEENKVSQVKIRFVNVFKDKTLANKLSFNFSDKQDVPVSEIILSFTPS
YYEDGLIGYDLGLVSLYNEKFYINNFGMMVSGLIYINDSLYYFKPPVNNL

*C. difficile* Toxin B 1145-1852
SEQ ID NO: 14
MPQDDLVISEIDFNNNSIVLGKCEIWRMEGGSGHTVTDDIDHFFSAPSITYREPHLSIYDVLEVQKEELDLSKD
LMVLPNAPNRVFAWETGWTPGLRSLENDGTKLLDRIRDNYEGEFYWRYFAFIADALITTLKPRYEDTNIRINLD
SNTRSFIVPIITTEYIREKLSYSFYGSGGTYALSLSQYNMGINIELSESDVWIIDVDNVVRDVTIESDKIKKGD
LIEGILSTLSIEENKIILNSHEINFSGEVNGSNGFVSLTFSILEGINAIIEVDLLSKSYKLLISGELKILMLNS
NHIQQKIDYIGFNSELQKNIPYSFVDSEGKENGFINGSTKEGLFVSELPDVVLISKVYMDDSKPSFGYYSNNLK
DVKVITKDNVNILTGYYLKDDIKISLSLTLQDEKTIKLNSVHLDESGVAEILKFMNRKGNTNTSDSLMSFLESM
NIKSIFVNFLQSNIKFILDANFIISGTTSIGQFEFICDENDNIQPYFIKFNTLETNYTLYVGNRQNMIVEPNYD
LDDSGDISSTVINFSQKYLYGIDSCVNKVVISPNIYTDEINITPVYETNNTYPEVIVLDANYINEKINVNINDL
SIRYVWSNDGNDFILMSTSEENKVSQVKIRFVNVFKDKTLANKLSFNFSDKQDVPVSEIILSFTPSYYEDGLIG
YDLGLVSLYNEKFYINNFGMMVSGLIYINDSLYYFKPPVNNL

*C. difficile* Toxin B 1350-1852
SEQ ID NO: 15
NVVRDVTIESDKIKKGDLIEGILSTLSIEENKIILNSHEINFSGEVNGSNGFVSLTFSILEGINAIIEVDLLSK
SYKLLISGELKILMLNSNHIQQKIDYIGFNSELQKNIPYSFVDSEGKENGFINGSTKEGLFVSELPDVVLISKV
YMDDSKPSFGYYSNNLKDVKVITKDNVNILTGYYLKDDIKISLSLTLQDEKTIKLNSVHLDESGVAEILKFMNR
KGNTNTSDSLMSFLESMNIKSIFVNFLQSNIKFILDANFIISGTTSIGQFEFICDENDNIQPYFIKFNTLETNY
TLYVGNRQNMIVEPNYDLDDSGDISSTVINFSQKYLYGIDSCVNKVVISPNIYTDEINITPVYETNNTYPEVIV
LDANYINEKINVNINDLSIRYVWSNDGNDFILMSTSEENKVSQVKIRFVNVFKDKTLANKLSFNFSDKQDVPVS
EIILSFTPSYYEDGLIGYDLGLVSLYNEKFYINNFGMMVSGLIYINDSLYYFKPPVNNL Protein domain from amino acid residues 27-401 of *C. difficile* CD2767
SEQ ID NO: 16
SNDKEMRAAWISTVYNLDWPKTKNNEAKQKKEYTDLLDKLKSVGINTAVVQVRPKSDALYKSNINPWSEYLTGT
QGKDPGYDPLPFLIEEAHKRGMEFHAWFNPYRITMADESIDKLPANHPAKKNP SWVVKHGNKYYYDPGLPEVRK
YIVDSIAEVVQNYDIDGVHFDDYFYPGVSFNDTATYQKYGKGQNKDDWRRENVNTLLRDVKASIKSIKPNVVFG
VSPAGIWRNKSSDPTGSDTSGNESYVGTYADTRAWIKQGLIDYVVPQLYVPIGLKAADYSKLVAVWVANEVKG
TNVDLYIGQGIYKQGQSSYGGQNIAKEIVQQVTLNRKYSEIKGSMYFSAKDIANSTSIQKDLKSLYSSSEEPVT
PPSNVKV CD2767 (27-401) Toxin A (542-1850)-fusion protein in a expression contruct
SEQ ID NO: 17
MGSSHHHHHHSSGLVPRGSHMSNDKEMRAAWISTVYNLDWPKTKNNEAKQKKEYTDLLDKLKSVGINTAVVQVR
PKSDALYKSNINPWSEYLTGTQGKDPGYDPLPFLIEEAHKRGMEFHAWFNPYRITMADESIDKLPANHPAKKNP
SWVVKHGNKYYYDPGLPEVRKYIVDSIAEVVQNYDIDGVHFDDYFYPGVSFNDTATYQKYGKGQNKDNWRRENV
NTLLRDVKASIKSIKPNVVFGVSPAGIWRNKSSDPTGSDTSGNESYVGTYADTRAWIKQGLIDYVVPQLYWPIG
LKAADYSKLVAVWVANEVKGTNVDLYIGQGIYKQGQSSYGGQNIAKEIVQQVTLNRKYSEIKGSMYFSAKDIAN
STSIQKDLKSLYSSSEEPVTPPSNVKVAAAPFTLSEDNGVDFNKNTALDKNYLLNNKIPSNNVEEAGSKNYVHY
IIQLQGDDISYEATCNLFSKNPKNSIIIQRNMNESAKSYFLSDDGESILELNKYRIPERLKNKEKVKVTFIGHG
KDEFNTSEFARLSVDSLSNEISSFLDTIKLDISPKNVEVNLLGSNMFSYDFNVEETYPGKLLLSIMDKITSTLP
DVNKNSITIGANQYEVRINSEGRKELLAHSGKWINKEEAIMSDLSSKEYIFFDSIDNKLKAKSKNIPGLASISE
DIKTLLLDASVSPDTKFILNNLKLNIESSIGDYIYYEKLEPVKNIIHNSIDDLIDEFNLLENVSDELYELKKLN
NLDEKYLISFEDISKNNSTYSVRFINKSNGESVYVETEKEIFSKYSEHITKEISTIKNSIITDVNGNLLDNIQL
DHTSQVNTLNAAFFIQSLIDYSSNKDVLNDLSTSVKVQLYAQLFSTGLNTIYDSIQLVNLISNAVNDTINVLPT
ITEGIPIVSTILDGINLGAAIKELLDEHDPLLKKELEAKVGVLAINMSLSIAATVASIVGIGAEVTIFLLPIAG
ISAGIPSLVNNELILHDKATSVVNYFNHLSESKKYGPLKTEDDKILVPIDDLVISEIDFNNNSIKLGTCNILAM
EGGSGHTVTGNIDHFFSSPSISSHIPSLSIYSAIGIETENLDFSKKIMMLPNAPSRVFVWVETGAVPGLRSLEN
DGTRLLDSIRDLYPGKFYWRFYAFFDYAITTLKPVYEDTNIKIKLDKDTRNFIMPTITTNEIRNKLSYSFDGAG
GTYSLLLSSYPISTNINLSKDDLWIFNIDNEVREISIENGTIKKGKLIKDVLSKIDINKNKLIIGNQTIDFSGD
IDNKDRYIFLTCELDDKISLIIEINLVAKSYSLLLSGDKNYLISNLSNIIEKINTLGLDSKNIAYNYTDESNNK
YFGAISKTSQKSIIHYKKDSKNILEFYNDSTLEFNSKDFIAEDINVFMKDDINTITGKYYVDNNTDKSIDFSIS
LVSKNQVKVNGLYLNESVYSSYLDFVKNSDGHHNTSNFMNLFLDNISFWKLFGFENINFVIDKYFTLVGKTNLG
YVEFICDNNKNIDIYFGEWKTSSSKSTIFSGNGRNVVVEPIYNPDTGEDISTSLDFSYEPLYGIDRYINKVLIA
PDLYTSLININTNYYSNEYYPEIIVLNPNTFHKKVNINLDSSSFEYKWSTEGSDFILVRYLEESNKKILQKIRI
KGILSNTQSFNKMSIDFKDIKKLSLGYIMSNFKSFNSENELDRDHLGFKIIDNKTYYYDEDSKLVKGLININNS
LFYFDPIEFNL CD2767 (27-401) Toxin 6 (767-1852)-fusion protein in a expression contruct
SEQ ID 18
SNDKEMRAAWISTVYNLDWPKTKNNEAKQKKEYTDLLDKLKSVGINTAVVQVRPKSDALYKSNINPWSEYLTGT
QGKDPGYDPLPFLIEEAHKRGMEFHAWFNPYRITMADESIDKLPANHPAKKNPSWVVKHGNKYYYDPGLPEVRK
YIVDSIAEVVQNYDIDGVHFDDYFYPGVSFNDTATYQKYGKGQNKDDWRRENVNTLLRDVKASIKSIKPNVVFG
VSPAGIWRNKSSDPTGSDTSGNESYVGTYADTRAWIKQGLIDYVVPQLYWPIGLKAADYSKLVAVWVANEVKGT
NVDLYIGQGIYKQGQSSYGGQNIAKEIVQQVTLNRKYSEIKGSMYFSAKDIANSTSIQKDLKSLYSSSEEPVTP
PSNVKVSIIKDISSKEYISFNPKENKITVKSKNLPELSTLLQEIRRNSNSSDIELEEKVMLTECEINVISNIDT
QIVEERIEEAKNLTSDSINYIKDEFKLIESISDALCDLKQQNELEDSHFISFEDISETDEGFSIRFINKETGES
IFVETEKTIFSEYANHITEEISKIKGTIFDTVNGKLVKKVNLDTTHEVNTLNAAFFIQSLIEYNSSKESLSNLS
VAMKVQVYAQLFSTGLNTITDAAKVVELVSTALDETIDLLPTLSEGLPIIATIIDGVSLGAAIKELSETSDPLL
RQEIEAKIGIMAVNLTTATTAIITSSLGIASGFSILLVPLAGISAGIPSLVNNELVLRDKATKVVDYFKHVSLV
ETEGVFTLLDDKIMMPQDDLVISEIDFNNNSIVLGKCEIWRMEGGSGHTVTDDIDHFFSAPSITYREPHLSIYD

| SED ID NOs |
|---|

VLEVQKEELDLSKDLMVLPNAPNRVFAWETGWTPGLRSLENDGTKLLDRIRDNYEGEFYWRYFAFIADALITTL
KPRYEDTNIRINLDSNTRSFIVPIITTEYIREKLSYSFYGSGGTYALSLSQYNMGINIELSESDVWIIDVDNVV
RDVTIESDKIKKGDLIEGILSTLSIEENKIILNSHEINFSGEVNGSNGFVSLTFSILEGINAIIEVDLLSKSYK
LLISGELKILMLNSNHIQQKIDYIGFNSELQKNIPYSFVDSEGKENGFINGSTKEGLFVSELPDVVLISKVYMD
DSKPSFGYYSNNLKDVKVITKDNVNILTGYYLKDDIKISLSLTLQDEKTIKLNSVHLDESGVAEILKFMNRKGN
TNTSDSLMSFLESMNIKSIFVNFLQSNIKFILDANFIISGTTSIGQFEFICDENDNIQPYFIKFNTLETNYTLY
VGNRQNMIVEPNYDLDDSGDISSTVINFSQKYLYGIDSCVNKVVISPNIYTDEINITPVYETNNTYPEVIVLDA
NYINEKINVNINDLSIRYVWSNDGNDFILMSTSEENKVSQVKIRFVNVFKDKTLANKLSFNFSDKQDVPVSEII
LSFTPSYYEDGLIGYDLGVSLYNEKFYINNFGMMVSGLIYINDSLYYFKPPVNNL

Toxin A (residues 542-1850; TxACPD) within the construct:
6His-Thioredoxin-TxACPD

SEQ ID 19

MGSSHHHHHHSHMASDKIIHLTDDSFDTDVLKADGAILVDFWAEWCGPCKMIAPILDEIADEYQGKLTVAKLNI
DQNPGTAPKYGIRGIPTLLLFKNGEVAATKVGALSKGQLKEFLDANLARALVPRGSVTSLYKKAGSAAAPFTLS
EDNGVDFNKNTALDKNYLLNNKIPSNNVEEAGSKNYVHYIIQLQGDDISYEATCNLFSKNPKNSIIIQRNMNES
AKSYFLSDDGESILELNKYRIPERLKNKEKVKVTFIGHGKDEFNTSEFARLSVDSLSNEISSFLDTIKLDISPK
NVEVNLLGSNMFSYDFNVEETYPGKLLLSIMDKITSTLPDVNKNSITIGANQYEVRINSEGRKELLAHSGKWIN
KEEAIMSDLSSKEYIFFDSIDNKLKAKSKNIPGLASISEDIKTLLLDASVSPDTKFILNNLKLNIESSIGDYIY
YEKLEPVKNIIHNSIDDLIDEFNLLENVSDELYELKKLNNLDEKYLISFEDISKNNSTYSVRFINKSNGESVYV
ETEKEIFSKYSEHITKEISTIKNSIITDVNGNLLDNIQLDHTSQVNTLNAAFFIQSLIDYSSNKDVLNDLSTSV
KVQLYAQLFSTGLNTIYDSIQLVNLISNAVNDTINVLPTITEGIPIVSTILDGINLGAAIKELLDEHDPLLKKE
LEAKVGVLAINMSLSIAATVASIVGIGAEVTIFLLPIAGISAGIPSLVNNELILHDKATSVVNYFNHLSESKKY
GPLKTEDDKILVPIDDLVISEIDFNNNSIKLGTCNILAMEGGSGHTVTDNIDHFFSSPSISSHIPSLSIYSAIG
IETENLDFSKKIMMLPNAPSRVFVWVETGAVPGLRSLENDGTRLLDSIRDLYPGKFYWRFYAFFDYAITTLKPV
YEDTNIKIKLDKDTRNFIMPTITTNEIRNKLSYSFDGAGGTYSLLLSSYPISTNINLSKDDLWIFNIDNEVREI
SIENGTIKKGKLIKDVLSKIDINKNKLIIGNQTIDFSGDIDNKDRYIFLTCELDDKISLIIEINLVAKSYSLLL
SGDKNYLISNLKSNIIEKINTLGLDSKNIAYNYTDESNNKYFGAISKTSQKSIIHYKKDSKNILEFYNDSTLEFN
SKDFIAEDINVFMKDDINTITGKYYVDNNTDKSIDFSISLVSKNQVKVNGLYLNESVYSSYLDFVKNSDGHHNT
SNFMNLFLDNISFWKLFGFENINFVIDKYFTLVGKTNLGYVEFICDNNKNIDIYFGEWKTSSSKSTIFSGNGRN
VVVEPIYNPDTGEDISTSLDFSYEPLYGIDRYINKVLIAPDLYTSLININTNYYSNEYYPEIIVLNPNTFHKKV
NINLDSSSFEYKWSTEGSDFILVRYLEESNKKILQKIRIKGILSNTQSFNKMSIDFKDIKKLSLGYIMSNFKSF
NSENELDRDHLGFKIIDNKTYYYDEDSKLVKGLININNSLFYFDPIEFNL

Toxin B (residues 767-1852; TxBc) within the construct:
6His-Thioredoxin-TxBc

SEQ ID 20

MGSSHHHHHHSHMASDKIIHLTDDSFDTDVLKADGAILVDFWAEWCGPCKMIAPILDEIADEYQGKLTVAKLNI
DQNPGTAPKYGIRGIPTLLLFKNGEVAATKVGALSKGQLKEFLDANLARALVPRGSVTSLYKKAGSAAAPFTSI
IKDISSKEYISFNPKENKITVKSKNLPELSTLLQEIRNNSNSSDIELEEKVMLTECEINVSNIDTQIVEERIE
EAKNLTSDSINYIKDEFKLIESISDALCDLKQQNELEDSHFISFEDISETDEGFSIRFINKETGESIFVETEKT
IFSEYANHITEEISKIKGTIFDTVNGKLVKKVNLDTTHEVNTLNAAFFIQSLIEYNSSKESLSNLSVAMKVQVY
AQLFSTGLNTITDAAKVVELVSTALDETIDLLPTLSEGLPIIATIIDGVSLGAAIKELSETSDPLLRQEIEAKI
GIMAVNLTTATTAIITSSLGIASGFSILLVPLAGISAGIPSLVNNELVLRDKATKVVDYFKHVSLVETEGVFTL
LDDKIMMPQDDLVISEIDFNNNSIVLGKCEIWRMEGGSGHTVTDDIDHFFSAPSITYREPHLSIYDVLEVQKEE
LDLSKDLMVLPNAPNRVFAWETGWTPGLRSLENDGTKLLDRIRDNYEGEFYWRYFAFIADALITTLKPRYEDTN
IRINLDSNTRSFIVPIITTEYIREKLSYSFYGSGGTYALSLSQYNMGINIELSESDVWIIDVDNVVRDVTIESD
KIKKGDLIEGILSTLSIEENKIILNSHEINFSGEVNGSNGFVSLTFSILEGINAIIEVDLLSKSYKLLISGELK
ILMLNSNHIQQKIDYIGFNSELQKNIPYSFVDSEGKENGFINGSTKEGLFVSELPDVVLISKVYMDDSKPSFGY
YSNNLKDVKVITKDNVNILTGYYLKDDIKISLSLTLQDEKTIKLNSVHLDESGVAEILKFMNRKGNTNTSDSLM
SFLESMNIKSIFVNFLQSNIKFILDANFIISGTTSIGQFEFICDENDNIQPYFIKFNTLETNYTLYVGNRQNMI
VEPNYDLDDSGDISSTVINFSQKYLYGIDSCVNKVVISPNIYTDEINITPVYETNNTYPEVIVLDANYINEKIN
VNINDLSIRYVWSNDGNDFILMSTSEENKVSQVKIRFVNVFKDKTLANKLSFNFSDKQDVPVSEIILSFTPSYY
EDGLIGYDLGVSLYNEKFYINNFGMMVSGLIYINDSLYYFKPPVNNLKGGRADPAFLYKVVSAWSHPQFEK

| SEQUENCE LISTING |
|---|

<160> NUMBER OF SEQ ID NOS: 20

<210> SEQ ID NO 1
<211> LENGTH: 2710
<212> TYPE: PRT
<213> ORGANISM: Artificial Sequence
<220> FEATURE:
<223> OTHER INFORMATION: Clostridium difficile Toxin A (Toxinotype 0)

<400> SEQUENCE: 1

Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
            20                  25                  30

```
Tyr Asn Lys Leu Thr Thr Asn Asn Glu Asn Lys Tyr Leu Gln Leu
             35                  40                  45

Lys Lys Leu Asn Glu Ser Ile Asp Val Phe Met Asn Lys Tyr Lys Thr
 50                  55                  60

Ser Ser Arg Asn Arg Ala Leu Ser Asn Leu Lys Lys Asp Ile Leu Lys
 65                  70                  75                  80

Glu Val Ile Leu Ile Lys Asn Ser Asn Thr Ser Pro Val Lys Asn
                     85                  90                  95

Leu His Phe Val Trp Ile Gly Gly Glu Val Ser Asp Ile Ala Leu Glu
                100                 105                 110

Tyr Ile Lys Gln Trp Ala Asp Ile Asn Ala Glu Tyr Asn Ile Lys Leu
            115                 120                 125

Trp Tyr Asp Ser Glu Ala Phe Leu Val Asn Thr Leu Lys Lys Ala Ile
            130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                165                 170                 175

Phe Ile Tyr Asp Arg Gln Lys Arg Phe Ile Asn Tyr Tyr Lys Ser Gln
            180                 185                 190

Ile Asn Lys Pro Thr Val Pro Thr Ile Asp Asp Ile Ile Lys Ser His
            195                 200                 205

Leu Val Ser Glu Tyr Asn Arg Asp Glu Thr Val Leu Glu Ser Tyr Arg
            210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
                245                 250                 255

Glu Leu Leu Asn Arg Gly Asn Leu Ala Ala Ala Ser Asp Ile Val Arg
            260                 265                 270

Leu Leu Ala Leu Lys Asn Phe Gly Gly Val Tyr Leu Asp Val Asp Met
            275                 280                 285

Leu Pro Gly Ile His Ser Asp Leu Phe Lys Thr Ile Ser Arg Pro Ser
            290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
                325                 330                 335

Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
            355                 360                 365

Asp Leu Glu Ile Lys Ile Ala Phe Ala Leu Gly Ser Val Ile Asn Gln
            370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
                405                 410                 415

Ile Glu Ser Asp Asn Asn Phe Thr Asp Thr Thr Lys Ile Phe His Asp
            420                 425                 430

Ser Leu Phe Asn Ser Ala Thr Ala Glu Asn Ser Met Phe Leu Thr Lys
            435                 440                 445
```

-continued

```
Ile Ala Pro Tyr Leu Gln Val Gly Phe Met Pro Glu Ala Arg Ser Thr
450                 455                 460
Ile Ser Leu Ser Gly Pro Gly Ala Tyr Ala Ser Ala Tyr Tyr Asp Phe
465                 470                 475                 480
Ile Asn Leu Gln Glu Asn Thr Ile Glu Lys Thr Leu Lys Ala Ser Asp
                485                 490                 495
Leu Ile Glu Phe Lys Phe Pro Glu Asn Asn Leu Ser Gln Leu Thr Glu
            500                 505                 510
Gln Glu Ile Asn Ser Leu Trp Ser Phe Asp Gln Ala Ser Ala Lys Tyr
        515                 520                 525
Gln Phe Glu Lys Tyr Val Arg Asp Tyr Thr Gly Gly Ser Leu Ser Glu
530                 535                 540
Asp Asn Gly Val Asp Phe Asn Lys Asn Thr Ala Leu Asp Lys Asn Tyr
545                 550                 555                 560
Leu Leu Asn Asn Lys Ile Pro Ser Asn Val Glu Glu Ala Gly Ser
                565                 570                 575
Lys Asn Tyr Val His Tyr Ile Ile Gln Leu Gln Gly Asp Asp Ile Ser
                580                 585                 590
Tyr Glu Ala Thr Cys Asn Leu Phe Ser Lys Asn Pro Lys Asn Ser Ile
            595                 600                 605
Ile Ile Gln Arg Asn Met Asn Glu Ser Ala Lys Ser Tyr Phe Leu Ser
        610                 615                 620
Asp Asp Gly Glu Ser Ile Leu Glu Leu Asn Lys Tyr Arg Ile Pro Glu
625                 630                 635                 640
Arg Leu Lys Asn Lys Glu Lys Val Lys Val Thr Phe Ile Gly His Gly
                645                 650                 655
Lys Asp Glu Phe Asn Thr Ser Glu Phe Ala Arg Leu Ser Val Asp Ser
                660                 665                 670
Leu Ser Asn Glu Ile Ser Ser Phe Leu Asp Thr Ile Lys Leu Asp Ile
            675                 680                 685
Ser Pro Lys Asn Val Glu Val Asn Leu Leu Gly Cys Asn Met Phe Ser
        690                 695                 700
Tyr Asp Phe Asn Val Glu Glu Thr Tyr Pro Gly Lys Leu Leu Leu Ser
705                 710                 715                 720
Ile Met Asp Lys Ile Thr Ser Thr Leu Pro Asp Val Asn Lys Asn Ser
                725                 730                 735
Ile Thr Ile Gly Ala Asn Gln Tyr Glu Val Arg Ile Asn Ser Glu Gly
                740                 745                 750
Arg Lys Glu Leu Leu Ala His Ser Gly Lys Trp Ile Asn Lys Glu Glu
            755                 760                 765
Ala Ile Met Ser Asp Leu Ser Ser Lys Glu Tyr Ile Phe Phe Asp Ser
        770                 775                 780
Ile Asp Asn Lys Leu Lys Ala Lys Ser Lys Asn Ile Pro Gly Leu Ala
785                 790                 795                 800
Ser Ile Ser Glu Asp Ile Lys Thr Leu Leu Leu Asp Ala Ser Val Ser
                805                 810                 815
Pro Asp Thr Lys Phe Ile Leu Asn Asn Leu Lys Leu Asn Ile Glu Ser
                820                 825                 830
Ser Ile Gly Asp Tyr Ile Tyr Tyr Glu Lys Leu Glu Pro Val Lys Asn
            835                 840                 845
Ile Ile His Asn Ser Ile Asp Asp Leu Ile Asp Glu Phe Asn Leu Leu
        850                 855                 860
Glu Asn Val Ser Asp Glu Leu Tyr Glu Leu Lys Lys Leu Asn Asn Leu
```

```
865                 870                 875                 880
Asp Glu Lys Tyr Leu Ile Ser Phe Glu Asp Ile Ser Lys Asn Asn Ser
                    885                 890                 895
Thr Tyr Ser Val Arg Phe Ile Asn Lys Ser Asn Gly Glu Ser Val Tyr
                    900                 905                 910
Val Glu Thr Glu Lys Glu Ile Phe Ser Lys Tyr Ser Glu His Ile Thr
                    915                 920                 925
Lys Glu Ile Ser Thr Ile Lys Asn Ser Ile Ile Thr Asp Val Asn Gly
                    930                 935                 940
Asn Leu Leu Asp Asn Ile Gln Leu Asp His Thr Ser Gln Val Asn Thr
945                 950                 955                 960
Leu Asn Ala Ala Phe Phe Ile Gln Ser Leu Ile Asp Tyr Ser Ser Asn
                    965                 970                 975
Lys Asp Val Leu Asn Asp Leu Ser Thr Ser Val Lys Val Gln Leu Tyr
                    980                 985                 990
Ala Gln Leu Phe Ser Thr Gly Leu Asn Thr Ile Tyr Asp Ser Ile Gln
                    995                 1000                1005
Leu Val Asn Leu Ile Ser Asn Ala Val Asn Asp Thr Ile Asn Val
                    1010                1015                1020
Leu Pro Thr Ile Thr Glu Gly Ile Pro Ile Val Ser Thr Ile Leu
                    1025                1030                1035
Asp Gly Ile Asn Leu Gly Ala Ala Ile Lys Glu Leu Leu Asp Glu
                    1040                1045                1050
His Asp Pro Leu Leu Lys Lys Glu Leu Glu Ala Lys Val Gly Val
                    1055                1060                1065
Leu Ala Ile Asn Met Ser Leu Ser Ile Ala Ala Thr Val Ala Ser
                    1070                1075                1080
Ile Val Gly Ile Gly Ala Glu Val Thr Ile Phe Leu Leu Pro Ile
                    1085                1090                1095
Ala Gly Ile Ser Ala Gly Ile Pro Ser Leu Val Asn Asn Glu Leu
                    1100                1105                1110
Ile Leu His Asp Lys Ala Thr Ser Val Val Asn Tyr Phe Asn His
                    1115                1120                1125
Leu Ser Glu Ser Lys Lys Tyr Gly Pro Leu Lys Thr Glu Asp Asp
                    1130                1135                1140
Lys Ile Leu Val Pro Ile Asp Asp Leu Val Ile Ser Glu Ile Asp
                    1145                1150                1155
Phe Asn Asn Asn Ser Ile Lys Leu Gly Thr Cys Asn Ile Leu Ala
                    1160                1165                1170
Met Glu Gly Gly Ser Gly His Thr Val Thr Gly Asn Ile Asp His
                    1175                1180                1185
Phe Phe Ser Ser Pro Ser Ile Ser Ser His Ile Pro Ser Leu Ser
                    1190                1195                1200
Ile Tyr Ser Ala Ile Gly Ile Glu Thr Glu Asn Leu Asp Phe Ser
                    1205                1210                1215
Lys Lys Ile Met Met Leu Pro Asn Ala Pro Ser Arg Val Phe Trp
                    1220                1225                1230
Trp Glu Thr Gly Ala Val Pro Gly Leu Arg Ser Leu Glu Asn Asp
                    1235                1240                1245
Gly Thr Arg Leu Leu Asp Ser Ile Arg Asp Leu Tyr Pro Gly Lys
                    1250                1255                1260
Phe Tyr Trp Arg Phe Tyr Ala Phe Phe Asp Tyr Ala Ile Thr Thr
                    1265                1270                1275
```

-continued

```
Leu Lys Pro Val Tyr Glu Asp Thr Asn Ile Lys Ile Lys Leu Asp
    1280            1285            1290

Lys Asp Thr Arg Asn Phe Ile Met Pro Thr Ile Thr Thr Asn Glu
    1295            1300            1305

Ile Arg Asn Lys Leu Ser Tyr Ser Phe Asp Gly Ala Gly Gly Thr
    1310            1315            1320

Tyr Ser Leu Leu Leu Ser Ser Tyr Pro Ile Ser Thr Asn Ile Asn
    1325            1330            1335

Leu Ser Lys Asp Asp Leu Trp Ile Phe Asn Ile Asp Asn Glu Val
    1340            1345            1350

Arg Glu Ile Ser Ile Glu Asn Gly Thr Ile Lys Lys Gly Lys Leu
    1355            1360            1365

Ile Lys Asp Val Leu Ser Lys Ile Asp Ile Asn Lys Asn Lys Leu
    1370            1375            1380

Ile Ile Gly Asn Gln Thr Ile Asp Phe Ser Gly Asp Ile Asp Asn
    1385            1390            1395

Lys Asp Arg Tyr Ile Phe Leu Thr Cys Glu Leu Asp Asp Lys Ile
    1400            1405            1410

Ser Leu Ile Ile Glu Ile Asn Leu Val Ala Lys Ser Tyr Ser Leu
    1415            1420            1425

Leu Leu Ser Gly Asp Lys Asn Tyr Leu Ile Ser Asn Leu Ser Asn
    1430            1435            1440

Thr Ile Glu Lys Ile Asn Thr Leu Gly Leu Asp Ser Lys Asn Ile
    1445            1450            1455

Ala Tyr Asn Tyr Thr Asp Glu Ser Asn Asn Lys Tyr Phe Gly Ala
    1460            1465            1470

Ile Ser Lys Thr Ser Gln Lys Ser Ile Ile His Tyr Lys Lys Asp
    1475            1480            1485

Ser Lys Asn Ile Leu Glu Phe Tyr Asn Asp Ser Thr Leu Glu Phe
    1490            1495            1500

Asn Ser Lys Asp Phe Ile Ala Glu Asp Ile Asn Val Phe Met Lys
    1505            1510            1515

Asp Asp Ile Asn Thr Ile Thr Gly Lys Tyr Tyr Val Asp Asn Asn
    1520            1525            1530

Thr Asp Lys Ser Ile Asp Phe Ser Ile Ser Leu Val Ser Lys Asn
    1535            1540            1545

Gln Val Lys Val Asn Gly Leu Tyr Leu Asn Glu Ser Val Tyr Ser
    1550            1555            1560

Ser Tyr Leu Asp Phe Val Lys Asn Ser Asp Gly His His Asn Thr
    1565            1570            1575

Ser Asn Phe Met Asn Leu Phe Leu Asp Asn Ile Ser Phe Trp Lys
    1580            1585            1590

Leu Phe Gly Phe Glu Asn Ile Asn Phe Val Ile Asp Lys Tyr Phe
    1595            1600            1605

Thr Leu Val Gly Lys Thr Asn Leu Gly Tyr Val Glu Phe Ile Cys
    1610            1615            1620

Asp Asn Asn Lys Asn Ile Asp Ile Tyr Phe Gly Glu Trp Lys Thr
    1625            1630            1635

Ser Ser Ser Lys Ser Thr Ile Phe Ser Gly Asn Gly Arg Asn Val
    1640            1645            1650

Val Val Glu Pro Ile Tyr Asn Pro Asp Thr Gly Glu Asp Ile Ser
    1655            1660            1665
```

```
Thr Ser Leu Asp Phe Ser Tyr Glu Pro Leu Tyr Gly Ile Asp Arg
    1670            1675            1680

Tyr Ile Asn Lys Val Leu Ile Ala Pro Asp Leu Tyr Thr Ser Leu
    1685            1690            1695

Ile Asn Ile Asn Thr Asn Tyr Tyr Ser Asn Glu Tyr Tyr Pro Glu
    1700            1705            1710

Ile Ile Val Leu Asn Pro Asn Thr Phe His Lys Lys Val Asn Ile
    1715            1720            1725

Asn Leu Asp Ser Ser Ser Phe Glu Tyr Lys Trp Ser Thr Glu Gly
    1730            1735            1740

Ser Asp Phe Ile Leu Val Arg Tyr Leu Glu Glu Ser Asn Lys Lys
    1745            1750            1755

Ile Leu Gln Lys Ile Arg Ile Lys Gly Ile Leu Ser Asn Thr Gln
    1760            1765            1770

Ser Phe Asn Lys Met Ser Ile Asp Phe Lys Asp Ile Lys Lys Leu
    1775            1780            1785

Ser Leu Gly Tyr Ile Met Ser Asn Phe Lys Ser Phe Asn Ser Glu
    1790            1795            1800

Asn Glu Leu Asp Arg Asp His Leu Gly Phe Lys Ile Ile Asp Asn
    1805            1810            1815

Lys Thr Tyr Tyr Tyr Asp Glu Asp Ser Lys Leu Val Lys Gly Leu
    1820            1825            1830

Ile Asn Ile Asn Asn Ser Leu Phe Tyr Phe Asp Pro Ile Glu Phe
    1835            1840            1845

Asn Leu Val Thr Gly Trp Gln Thr Ile Asn Gly Lys Lys Tyr Tyr
    1850            1855            1860

Phe Asp Ile Asn Thr Gly Ala Ala Leu Thr Ser Tyr Lys Ile Ile
    1865            1870            1875

Asn Gly Lys His Phe Tyr Phe Asn Asn Asp Gly Val Met Gln Leu
    1880            1885            1890

Gly Val Phe Lys Gly Pro Asp Gly Phe Glu Tyr Phe Ala Pro Ala
    1895            1900            1905

Asn Thr Gln Asn Asn Asn Ile Glu Gly Gln Ala Ile Val Tyr Gln
    1910            1915            1920

Ser Lys Phe Leu Thr Leu Asn Gly Lys Lys Tyr Tyr Phe Asp Asn
    1925            1930            1935

Asn Ser Lys Ala Val Thr Gly Trp Arg Ile Ile Asn Asn Glu Lys
    1940            1945            1950

Tyr Tyr Phe Asn Pro Asn Asn Ala Ile Ala Ala Val Gly Leu Gln
    1955            1960            1965

Val Ile Asp Asn Asn Lys Tyr Tyr Phe Asn Pro Asp Thr Ala Ile
    1970            1975            1980

Ile Ser Lys Gly Trp Gln Thr Val Asn Gly Ser Arg Tyr Tyr Phe
    1985            1990            1995

Asp Thr Asp Thr Ala Ile Ala Phe Asn Gly Tyr Lys Thr Ile Asp
    2000            2005            2010

Gly Lys His Phe Tyr Phe Asp Ser Asp Cys Val Val Lys Ile Gly
    2015            2020            2025

Val Phe Ser Thr Ser Asn Gly Phe Glu Tyr Phe Ala Pro Ala Asn
    2030            2035            2040

Thr Tyr Asn Asn Asn Ile Glu Gly Gln Ala Ile Val Tyr Gln Ser
    2045            2050            2055

Lys Phe Leu Thr Leu Asn Gly Lys Lys Tyr Tyr Phe Asp Asn Asn
```

-continued

```
                2060                2065                2070
Ser Lys Ala Val Thr Gly Leu Gln Thr Ile Asp Ser Lys Lys Tyr
    2075                2080                2085
Tyr Phe Asn Thr Asn Thr Ala Glu Ala Ala Thr Gly Trp Gln Thr
    2090                2095                2100
Ile Asp Gly Lys Lys Tyr Tyr Phe Asn Thr Asn Thr Ala Glu Ala
    2105                2110                2115
Ala Thr Gly Trp Gln Thr Ile Asp Gly Lys Lys Tyr Tyr Phe Asn
    2120                2125                2130
Thr Asn Thr Ala Ile Ala Ser Thr Gly Tyr Thr Ile Ile Asn Gly
    2135                2140                2145
Lys His Phe Tyr Phe Asn Thr Asp Gly Ile Met Gln Ile Gly Val
    2150                2155                2160
Phe Lys Gly Pro Asn Gly Phe Glu Tyr Phe Ala Pro Ala Asn Thr
    2165                2170                2175
Asp Ala Asn Asn Ile Glu Gly Gln Ala Ile Leu Tyr Gln Asn Glu
    2180                2185                2190
Phe Leu Thr Leu Asn Gly Lys Lys Tyr Tyr Phe Gly Ser Asp Ser
    2195                2200                2205
Lys Ala Val Thr Gly Trp Arg Ile Ile Asn Asn Lys Lys Tyr Tyr
    2210                2215                2220
Phe Asn Pro Asn Asn Ala Ile Ala Ala Ile His Leu Cys Thr Ile
    2225                2230                2235
Asn Asn Asp Lys Tyr Tyr Phe Ser Tyr Asp Gly Ile Leu Gln Asn
    2240                2245                2250
Gly Tyr Ile Thr Ile Glu Arg Asn Asn Phe Tyr Phe Asp Ala Asn
    2255                2260                2265
Asn Glu Ser Lys Met Val Thr Gly Val Phe Lys Gly Pro Asn Gly
    2270                2275                2280
Phe Glu Tyr Phe Ala Pro Ala Asn Thr His Asn Asn Asn Ile Glu
    2285                2290                2295
Gly Gln Ala Ile Val Tyr Gln Asn Lys Phe Leu Thr Leu Asn Gly
    2300                2305                2310
Lys Lys Tyr Tyr Phe Asp Asn Asp Ser Lys Ala Val Thr Gly Trp
    2315                2320                2325
Gln Thr Ile Asp Gly Lys Lys Tyr Tyr Phe Asn Leu Asn Thr Ala
    2330                2335                2340
Glu Ala Ala Thr Gly Trp Gln Thr Ile Asp Gly Lys Lys Tyr Tyr
    2345                2350                2355
Phe Asn Leu Asn Thr Ala Glu Ala Ala Thr Gly Trp Gln Thr Ile
    2360                2365                2370
Asp Gly Lys Lys Tyr Tyr Phe Asn Thr Asn Thr Phe Ile Ala Ser
    2375                2380                2385
Thr Gly Tyr Thr Ser Ile Asn Gly Lys His Phe Tyr Phe Asn Thr
    2390                2395                2400
Asp Gly Ile Met Gln Ile Gly Val Phe Lys Gly Pro Asn Gly Phe
    2405                2410                2415
Glu Tyr Phe Ala Pro Ala Asn Thr Asp Ala Asn Asn Ile Glu Gly
    2420                2425                2430
Gln Ala Ile Leu Tyr Gln Asn Lys Phe Leu Thr Leu Asn Gly Lys
    2435                2440                2445
Lys Tyr Tyr Phe Gly Ser Asp Ser Lys Ala Val Thr Gly Leu Arg
    2450                2455                2460
```

```
Thr Ile Asp Gly Lys Lys Tyr Tyr Phe Asn Thr Asn Thr Ala Val
    2465                2470                2475

Ala Val Thr Gly Trp Gln Thr Ile Asn Gly Lys Lys Tyr Tyr Phe
    2480                2485                2490

Asn Thr Asn Thr Ser Ile Ala Ser Thr Gly Tyr Thr Ile Ile Ser
    2495                2500                2505

Gly Lys His Phe Tyr Phe Asn Thr Asp Gly Ile Met Gln Ile Gly
    2510                2515                2520

Val Phe Lys Gly Pro Asp Gly Phe Glu Tyr Phe Ala Pro Ala Asn
    2525                2530                2535

Thr Asp Ala Asn Asn Ile Glu Gly Gln Ala Ile Arg Tyr Gln Asn
    2540                2545                2550

Arg Phe Leu Tyr Leu His Asp Asn Ile Tyr Tyr Phe Gly Asn Asn
    2555                2560                2565

Ser Lys Ala Ala Thr Gly Trp Val Thr Ile Asp Gly Asn Arg Tyr
    2570                2575                2580

Tyr Phe Glu Pro Asn Thr Ala Met Gly Ala Asn Gly Tyr Lys Thr
    2585                2590                2595

Ile Asp Asn Lys Asn Phe Tyr Phe Arg Asn Gly Leu Pro Gln Ile
    2600                2605                2610

Gly Val Phe Lys Gly Ser Asn Gly Phe Glu Tyr Phe Ala Pro Ala
    2615                2620                2625

Asn Thr Asp Ala Asn Asn Ile Glu Gly Gln Ala Ile Arg Tyr Gln
    2630                2635                2640

Asn Arg Phe Leu His Leu Leu Gly Lys Ile Tyr Tyr Phe Gly Asn
    2645                2650                2655

Asn Ser Lys Ala Val Thr Gly Trp Gln Thr Ile Asn Gly Lys Val
    2660                2665                2670

Tyr Tyr Phe Met Pro Asp Thr Ala Met Ala Ala Ala Gly Gly Leu
    2675                2680                2685

Phe Glu Ile Asp Gly Val Ile Tyr Phe Phe Gly Val Asp Gly Val
    2690                2695                2700

Lys Ala Pro Gly Ile Tyr Gly
    2705                2710

<210> SEQ ID NO 2
<211> LENGTH: 2366
<212> TYPE: PRT
<213> ORGANISM: Artificial Sequence
<220> FEATURE:
<223> OTHER INFORMATION: C. difficile Toxin B (Toxinotype 0)

<400> SEQUENCE: 2

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
                20                  25                  30

Glu Tyr His Asn Met Ser Glu Asn Thr Val Val Glu Lys Tyr Leu Lys
            35                  40                  45

Leu Lys Asp Ile Asn Ser Leu Thr Asp Ile Tyr Ile Asp Thr Tyr Lys
        50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95
```

```
Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
            115                 120                 125

Val Phe Tyr Asp Ser Asn Ala Phe Leu Ile Asn Thr Leu Lys Lys Thr
130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
            195                 200                 205

Tyr Leu Ser Asn Glu Tyr Ser Lys Glu Ile Asp Glu Leu Asn Thr Tyr
            210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asp
            275                 280                 285

Met Leu Pro Gly Ile Gln Pro Asp Leu Phe Glu Ser Ile Glu Lys Pro
            290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
                340                 345                 350

Lys Ser Asp Lys Ser Glu Ile Phe Ser Ser Leu Gly Asp Met Glu Ala
            355                 360                 365

Ser Pro Leu Glu Val Lys Ile Ala Phe Asn Ser Lys Gly Ile Ile Asn
370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
            420                 425                 430

Asp Ser Ile Met Ala Glu Ala Asn Ala Asp Asn Gly Arg Phe Met Met
            435                 440                 445

Glu Leu Gly Lys Tyr Leu Arg Val Gly Phe Phe Pro Asp Val Lys Thr
            450                 455                 460

Thr Ile Asn Leu Ser Gly Pro Glu Ala Tyr Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
            500                 505                 510
```

-continued

Glu Gln Glu Met Ala Ser Leu Trp Ser Phe Asp Asp Ala Arg Ala Lys
515                 520                 525

Ala Gln Phe Glu Glu Tyr Lys Arg Asn Tyr Phe Glu Gly Ser Leu Gly
530                 535                 540

Glu Asp Asp Asn Leu Asp Phe Ser Gln Asn Ile Val Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
                580                 585                 590

Ala Ala Cys Asn Leu Phe Ala Lys Thr Pro Tyr Asp Ser Val Leu Phe
                595                 600                 605

Gln Lys Asn Ile Glu Asp Ser Glu Ile Ala Tyr Tyr Tyr Asn Pro Gly
610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Phe Asp Val Asp Ser Leu Ser
                660                 665                 670

Thr Glu Ile Glu Ala Ala Ile Asp Leu Ala Lys Glu Asp Ile Ser Pro
                675                 680                 685

Lys Ser Ile Glu Ile Asn Leu Leu Gly Cys Asn Met Phe Ser Tyr Ser
                690                 695                 700

Ile Asn Val Glu Glu Thr Tyr Pro Gly Lys Leu Leu Leu Lys Val Lys
705                 710                 715                 720

Asp Lys Ile Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
                740                 745                 750

Glu Leu Leu Asp His Ser Gly Glu Trp Ile Asn Lys Glu Glu Ser Ile
                755                 760                 765

Ile Lys Asp Ile Ser Ser Lys Glu Tyr Ile Ser Phe Asn Pro Lys Glu
                770                 775                 780

Asn Lys Ile Thr Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
                805                 810                 815

Glu Lys Val Met Leu Thr Glu Cys Glu Ile Asn Val Ile Ser Asn Ile
                820                 825                 830

Asp Thr Gln Ile Val Glu Glu Arg Ile Glu Glu Ala Lys Asn Leu Thr
                835                 840                 845

Ser Asp Ser Ile Asn Tyr Ile Lys Asp Glu Phe Lys Leu Ile Glu Ser
850                 855                 860

Ile Ser Asp Ala Leu Cys Asp Leu Lys Gln Gln Asn Glu Leu Glu Asp
865                 870                 875                 880

Ser His Phe Ile Ser Phe Glu Asp Ile Ser Glu Thr Asp Glu Gly Phe
                885                 890                 895

Ser Ile Arg Phe Ile Asn Lys Glu Thr Gly Glu Ser Ile Phe Val Glu
                900                 905                 910

Thr Glu Lys Thr Ile Phe Ser Glu Tyr Ala Asn His Ile Thr Glu Glu
                915                 920                 925

Ile Ser Lys Ile Lys Gly Thr Ile Phe Asp Thr Val Asn Gly Lys Leu

```
            930             935             940
Val Lys Lys Val Asn Leu Asp Thr Thr His Glu Val Asn Thr Leu Asn
945                 950             955                 960

Ala Ala Phe Phe Ile Gln Ser Leu Ile Glu Tyr Asn Ser Ser Lys Glu
                965             970             975

Ser Leu Ser Asn Leu Ser Val Ala Met Lys Val Gln Val Tyr Ala Gln
            980             985             990

Leu Phe Ser Thr Gly Leu Asn Thr Ile Thr Asp Ala Ala Lys Val Val
        995             1000            1005

Glu Leu Val Ser Thr Ala Leu Asp Glu Thr Ile Asp Leu Leu Pro
    1010            1015            1020

Thr Leu Ser Glu Gly Leu Pro Ile Ile Ala Thr Ile Ile Asp Gly
    1025            1030            1035

Val Ser Leu Gly Ala Ala Ile Lys Glu Leu Ser Glu Thr Ser Asp
    1040            1045            1050

Pro Leu Leu Arg Gln Glu Ile Glu Ala Lys Ile Gly Ile Met Ala
    1055            1060            1065

Val Asn Leu Thr Thr Ala Thr Thr Ala Ile Ile Thr Ser Ser Leu
    1070            1075            1080

Gly Ile Ala Ser Gly Phe Ser Ile Leu Leu Val Pro Leu Ala Gly
    1085            1090            1095

Ile Ser Ala Gly Ile Pro Ser Leu Val Asn Asn Glu Leu Val Leu
    1100            1105            1110

Arg Asp Lys Ala Thr Lys Val Val Asp Tyr Phe Lys His Val Ser
    1115            1120            1125

Leu Val Glu Thr Glu Gly Val Phe Thr Leu Leu Asp Asp Lys Ile
    1130            1135            1140

Met Met Pro Gln Asp Asp Leu Val Ile Ser Glu Ile Asp Phe Asn
    1145            1150            1155

Asn Asn Ser Ile Val Leu Gly Lys Cys Glu Ile Trp Arg Met Glu
    1160            1165            1170

Gly Gly Ser Gly His Thr Val Thr Asp Asp Ile Asp His Phe Phe
    1175            1180            1185

Ser Ala Pro Ser Ile Thr Tyr Arg Glu Pro His Leu Ser Ile Tyr
    1190            1195            1200

Asp Val Leu Glu Val Gln Lys Glu Glu Leu Asp Leu Ser Lys Asp
    1205            1210            1215

Leu Met Val Leu Pro Asn Ala Pro Asn Arg Val Phe Ala Trp Glu
    1220            1225            1230

Thr Gly Trp Thr Pro Gly Leu Arg Ser Leu Glu Asn Asp Gly Thr
    1235            1240            1245

Lys Leu Leu Asp Arg Ile Arg Asp Asn Tyr Glu Gly Glu Phe Tyr
    1250            1255            1260

Trp Arg Tyr Phe Ala Phe Ile Ala Asp Ala Leu Ile Thr Thr Leu
    1265            1270            1275

Lys Pro Arg Tyr Glu Asp Thr Asn Ile Arg Ile Asn Leu Asp Ser
    1280            1285            1290

Asn Thr Arg Ser Phe Ile Val Pro Ile Ile Thr Thr Glu Tyr Ile
    1295            1300            1305

Arg Glu Lys Leu Ser Tyr Ser Phe Tyr Gly Ser Gly Gly Thr Tyr
    1310            1315            1320

Ala Leu Ser Leu Ser Gln Tyr Asn Met Gly Ile Asn Ile Glu Leu
    1325            1330            1335
```

-continued

```
Ser Glu Ser Asp Val Trp Ile Ile Asp Val Asp Asn Val Val Arg
1340                1345                1350
Asp Val Thr Ile Glu Ser Asp Lys Ile Lys Lys Gly Asp Leu Ile
        1355                1360                1365
Glu Gly Ile Leu Ser Thr Leu Ser Ile Glu Glu Asn Lys Ile Ile
1370                1375                1380
Leu Asn Ser His Glu Ile Asn Phe Ser Gly Glu Val Asn Gly Ser
        1385                1390                1395
Asn Gly Phe Val Ser Leu Thr Phe Ser Ile Leu Glu Gly Ile Asn
1400                1405                1410
Ala Ile Ile Glu Val Asp Leu Leu Ser Lys Ser Tyr Lys Leu Leu
        1415                1420                1425
Ile Ser Gly Glu Leu Lys Ile Leu Met Leu Asn Ser Asn His Ile
1430                1435                1440
Gln Gln Lys Ile Asp Tyr Ile Gly Phe Asn Ser Glu Leu Gln Lys
        1445                1450                1455
Asn Ile Pro Tyr Ser Phe Val Asp Ser Glu Gly Lys Glu Asn Gly
1460                1465                1470
Phe Ile Asn Gly Ser Thr Lys Glu Gly Leu Phe Val Ser Glu Leu
        1475                1480                1485
Pro Asp Val Val Leu Ile Ser Lys Val Tyr Met Asp Asp Ser Lys
1490                1495                1500
Pro Ser Phe Gly Tyr Tyr Ser Asn Asn Leu Lys Asp Val Lys Val
        1505                1510                1515
Ile Thr Lys Asp Asn Val Asn Ile Leu Thr Gly Tyr Tyr Leu Lys
1520                1525                1530
Asp Asp Ile Lys Ile Ser Leu Ser Leu Thr Leu Gln Asp Glu Lys
        1535                1540                1545
Thr Ile Lys Leu Asn Ser Val His Leu Asp Glu Ser Gly Val Ala
1550                1555                1560
Glu Ile Leu Lys Phe Met Asn Arg Lys Gly Asn Thr Asn Thr Ser
        1565                1570                1575
Asp Ser Leu Met Ser Phe Leu Glu Ser Met Asn Ile Lys Ser Ile
1580                1585                1590
Phe Val Asn Phe Leu Gln Ser Asn Ile Lys Phe Ile Leu Asp Ala
        1595                1600                1605
Asn Phe Ile Ile Ser Gly Thr Thr Ser Ile Gly Gln Phe Glu Phe
1610                1615                1620
Ile Cys Asp Glu Asn Asp Asn Ile Gln Pro Tyr Phe Ile Lys Phe
        1625                1630                1635
Asn Thr Leu Glu Thr Asn Tyr Thr Leu Tyr Val Gly Asn Arg Gln
1640                1645                1650
Asn Met Ile Val Glu Pro Asn Tyr Asp Leu Asp Asp Ser Gly Asp
        1655                1660                1665
Ile Ser Ser Thr Val Ile Asn Phe Ser Gln Lys Tyr Leu Tyr Gly
1670                1675                1680
Ile Asp Ser Cys Val Asn Lys Val Val Ile Ser Pro Asn Ile Tyr
        1685                1690                1695
Thr Asp Glu Ile Asn Ile Thr Pro Val Tyr Glu Thr Asn Asn Thr
1700                1705                1710
Tyr Pro Glu Val Ile Val Leu Asp Ala Asn Tyr Ile Asn Glu Lys
        1715                1720                1725
```

```
Ile Asn Val Asn Ile Asn Asp Leu Ser Ile Arg Tyr Val Trp Ser
    1730            1735                1740

Asn Asp Gly Asn Asp Phe Ile Leu Met Ser Thr Ser Glu Glu Asn
    1745            1750                1755

Lys Val Ser Gln Val Lys Ile Arg Phe Val Asn Val Phe Lys Asp
    1760            1765                1770

Lys Thr Leu Ala Asn Lys Leu Ser Phe Asn Phe Ser Asp Lys Gln
    1775            1780                1785

Asp Val Pro Val Ser Glu Ile Ile Leu Ser Phe Thr Pro Ser Tyr
    1790            1795                1800

Tyr Glu Asp Gly Leu Ile Gly Tyr Asp Leu Gly Leu Val Ser Leu
    1805            1810                1815

Tyr Asn Glu Lys Phe Tyr Ile Asn Asn Phe Gly Met Met Val Ser
    1820            1825                1830

Gly Leu Ile Tyr Ile Asn Asp Ser Leu Tyr Tyr Phe Lys Pro Pro
    1835            1840                1845

Val Asn Asn Leu Ile Thr Gly Phe Val Thr Val Gly Asp Asp Lys
    1850            1855                1860

Tyr Tyr Phe Asn Pro Ile Asn Gly Gly Ala Ala Ser Ile Gly Glu
    1865            1870                1875

Thr Ile Ile Asp Asp Lys Asn Tyr Tyr Phe Asn Gln Ser Gly Val
    1880            1885                1890

Leu Gln Thr Gly Val Phe Ser Thr Glu Asp Gly Phe Lys Tyr Phe
    1895            1900                1905

Ala Pro Ala Asn Thr Leu Asp Glu Asn Leu Glu Gly Glu Ala Ile
    1910            1915                1920

Asp Phe Thr Gly Lys Leu Ile Ile Asp Glu Asn Ile Tyr Tyr Phe
    1925            1930                1935

Asp Asp Asn Tyr Arg Gly Ala Val Glu Trp Lys Glu Leu Asp Gly
    1940            1945                1950

Glu Met His Tyr Phe Ser Pro Glu Thr Gly Lys Ala Phe Lys Gly
    1955            1960                1965

Leu Asn Gln Ile Gly Asp Tyr Lys Tyr Tyr Phe Asn Ser Asp Gly
    1970            1975                1980

Val Met Gln Lys Gly Phe Val Ser Ile Asn Asp Asn Lys His Tyr
    1985            1990                1995

Phe Asp Asp Ser Gly Val Met Lys Val Gly Tyr Thr Glu Ile Asp
    2000            2005                2010

Gly Lys His Phe Tyr Phe Ala Glu Asn Gly Glu Met Gln Ile Gly
    2015            2020                2025

Val Phe Asn Thr Glu Asp Gly Phe Lys Tyr Phe Ala His His Asn
    2030            2035                2040

Glu Asp Leu Gly Asn Glu Glu Gly Glu Glu Ile Ser Tyr Ser Gly
    2045            2050                2055

Ile Leu Asn Phe Asn Asn Lys Ile Tyr Tyr Phe Asp Asp Ser Phe
    2060            2065                2070

Thr Ala Val Val Gly Trp Lys Asp Leu Glu Asp Gly Ser Lys Tyr
    2075            2080                2085

Tyr Phe Asp Glu Asp Thr Ala Glu Ala Tyr Ile Gly Leu Ser Leu
    2090            2095                2100

Ile Asn Asp Gly Gln Tyr Tyr Phe Asn Asp Asp Gly Ile Met Gln
    2105            2110                2115

Val Gly Phe Val Thr Ile Asn Asp Lys Val Phe Tyr Phe Ser Asp
```

```
                2120                2125                2130

Ser Gly Ile Ile Glu Ser Gly Val Gln Asn Ile Asp Asp Asn Tyr
        2135                2140                2145

Phe Tyr Ile Asp Asp Asn Gly Ile Val Gln Ile Gly Val Phe Asp
        2150                2155                2160

Thr Ser Asp Gly Tyr Lys Tyr Phe Ala Pro Ala Asn Thr Val Asn
        2165                2170                2175

Asp Asn Ile Tyr Gly Gln Ala Val Glu Tyr Ser Gly Leu Val Arg
        2180                2185                2190

Val Gly Glu Asp Val Tyr Tyr Phe Gly Glu Thr Tyr Thr Ile Glu
        2195                2200                2205

Thr Gly Trp Ile Tyr Asp Met Glu Asn Glu Ser Asp Lys Tyr Tyr
        2210                2215                2220

Phe Asn Pro Glu Thr Lys Lys Ala Cys Lys Gly Ile Asn Leu Ile
        2225                2230                2235

Asp Asp Ile Lys Tyr Tyr Phe Asp Glu Lys Gly Ile Met Arg Thr
        2240                2245                2250

Gly Leu Ile Ser Phe Glu Asn Asn Asn Tyr Tyr Phe Asn Glu Asn
        2255                2260                2265

Gly Glu Met Gln Phe Gly Tyr Ile Asn Ile Glu Asp Lys Met Phe
        2270                2275                2280

Tyr Phe Gly Glu Asp Gly Val Met Gln Ile Gly Val Phe Asn Thr
        2285                2290                2295

Pro Asp Gly Phe Lys Tyr Phe Ala His Gln Asn Thr Leu Asp Glu
        2300                2305                2310

Asn Phe Glu Gly Glu Ser Ile Asn Tyr Thr Gly Trp Leu Asp Leu
        2315                2320                2325

Asp Glu Lys Arg Tyr Tyr Phe Thr Asp Glu Tyr Ile Ala Ala Thr
        2330                2335                2340

Gly Ser Val Ile Ile Asp Gly Glu Glu Tyr Tyr Phe Asp Pro Asp
        2345                2350                2355

Thr Ala Gln Leu Val Ile Ser Glu
        2360                2365

<210> SEQ ID NO 3
<211> LENGTH: 2710
<212> TYPE: PRT
<213> ORGANISM: Artificial Sequence
<220> FEATURE:
<223> OTHER INFORMATION: C. difficile Toxin A (Toxinotype 3)

<400> SEQUENCE: 3

Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
            20                  25                  30

Tyr Asn Lys Leu Thr Thr Asn Asn Asn Glu Asn Lys Tyr Leu Gln Leu
        35                  40                  45

Lys Lys Leu Asn Glu Ser Ile Asp Val Phe Met Asn Lys Tyr Lys Asn
    50                  55                  60

Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                85                  90                  95

Leu His Phe Val Trp Ile Gly Gly Glu Val Ser Asp Ile Ala Leu Glu
```

```
                100             105             110
Tyr Ile Lys Gln Trp Ala Asp Ile Asn Ala Glu Tyr Asn Ile Lys Leu
            115                 120                 125
Trp Tyr Asp Ser Glu Ala Phe Leu Val Asn Thr Leu Lys Lys Ala Ile
            130                 135                 140
Val Glu Ser Ser Thr Thr Glu Ala Leu Gln Leu Leu Glu Glu Glu Ile
145                 150                 155                 160
Gln Asn Pro Gln Phe Asp Asn Met Lys Phe Tyr Lys Lys Arg Met Glu
                165                 170                 175
Phe Ile Tyr Asp Arg Gln Lys Arg Phe Ile Asn Tyr Tyr Lys Ser Gln
                180                 185                 190
Ile Asn Lys Pro Thr Val Pro Thr Ile Asp Asp Ile Ile Lys Ser His
                195                 200                 205
Leu Val Ser Glu Tyr Asn Arg Asp Glu Thr Leu Leu Glu Ser Tyr Arg
            210                 215                 220
Thr Asn Ser Leu Arg Lys Ile Asn Ser Asn His Gly Ile Asp Ile Arg
225                 230                 235                 240
Ala Asn Ser Leu Phe Thr Glu Gln Glu Leu Leu Asn Ile Tyr Ser Gln
                245                 250                 255
Glu Leu Leu Asn Arg Gly Asn Leu Ala Ala Ser Asp Ile Val Arg
            260                 265                 270
Leu Leu Ala Leu Lys Asn Phe Gly Gly Val Tyr Leu Asp Val Asp Met
            275                 280                 285
Leu Pro Gly Ile His Ser Asp Leu Phe Lys Thr Ile Pro Arg Pro Ser
            290                 295                 300
Ser Ile Gly Leu Asp Arg Trp Glu Met Ile Lys Leu Glu Ala Ile Met
305                 310                 315                 320
Lys Tyr Lys Lys Tyr Ile Asn Asn Tyr Thr Ser Glu Asn Phe Asp Lys
                325                 330                 335
Leu Asp Gln Gln Leu Lys Asp Asn Phe Lys Leu Ile Ile Glu Ser Lys
            340                 345                 350
Ser Glu Lys Ser Glu Ile Phe Ser Lys Leu Glu Asn Leu Asn Val Ser
            355                 360                 365
Asp Leu Glu Ile Lys Ile Ala Phe Ala Leu Gly Ser Val Ile Asn Gln
            370                 375                 380
Ala Leu Ile Ser Lys Gln Gly Ser Tyr Leu Thr Asn Leu Val Ile Glu
385                 390                 395                 400
Gln Val Lys Asn Arg Tyr Gln Phe Leu Asn Gln His Leu Asn Pro Ala
                405                 410                 415
Ile Glu Ser Asp Asn Asn Phe Thr Asp Thr Thr Lys Ile Phe His Asp
                420                 425                 430
Ser Leu Phe Asn Ser Ala Thr Ala Glu Asn Ser Met Phe Leu Thr Lys
            435                 440                 445
Ile Ala Pro Tyr Leu Gln Val Gly Phe Met Pro Glu Ala Arg Ser Thr
            450                 455                 460
Ile Ser Leu Ser Gly Pro Gly Ala Tyr Ala Ser Ala Tyr Tyr Asp Phe
465                 470                 475                 480
Ile Asn Leu Gln Glu Asn Thr Ile Glu Lys Thr Leu Lys Ala Ser Asp
                485                 490                 495
Leu Ile Glu Phe Lys Phe Pro Glu Asn Asn Leu Ser Gln Leu Thr Glu
            500                 505                 510
Gln Glu Ile Asn Ser Leu Trp Ser Phe Asp Gln Ala Ser Ala Lys Tyr
            515                 520                 525
```

```
Gln Phe Glu Lys Tyr Val Arg Asp Tyr Thr Gly Gly Ser Leu Ser Glu
            530                 535                 540

Asp Asn Gly Val Asp Phe Asn Lys Asn Thr Ala Leu Asp Lys Asn Tyr
545                 550                 555                 560

Leu Leu Asn Asn Lys Ile Pro Ser Asn Asn Val Glu Glu Ala Gly Ser
                565                 570                 575

Lys Asn Tyr Val His Tyr Ile Ile Gln Leu Gln Gly Asp Asp Ile Ser
            580                 585                 590

Tyr Glu Ala Thr Cys Asn Leu Phe Ser Lys Asn Pro Lys Asn Ser Ile
            595                 600                 605

Ile Ile Gln Arg Asn Met Asn Glu Ser Ala Lys Ser Tyr Phe Leu Ser
610                 615                 620

Asp Asp Gly Glu Ser Ile Leu Glu Leu Asn Lys Tyr Arg Ile Pro Glu
625                 630                 635                 640

Arg Leu Lys Asn Lys Glu Lys Val Lys Val Thr Phe Ile Gly His Gly
                645                 650                 655

Lys Asp Glu Phe Asn Thr Ser Glu Phe Ala Arg Leu Ser Val Asp Ser
            660                 665                 670

Leu Ser Asn Glu Ile Ser Ser Phe Leu Asp Thr Ile Lys Leu Asp Ile
            675                 680                 685

Ser Pro Lys Asn Val Glu Val Asn Leu Leu Gly Cys Asn Met Phe Ser
690                 695                 700

Tyr Asp Phe Asn Val Glu Glu Thr Tyr Pro Gly Lys Leu Leu Leu Ser
705                 710                 715                 720

Ile Met Asp Lys Ile Thr Ser Thr Leu Pro Asp Val Asn Lys Asp Ser
                725                 730                 735

Ile Thr Ile Gly Ala Asn Gln Tyr Glu Val Arg Ile Asn Ser Glu Gly
            740                 745                 750

Arg Lys Glu Leu Leu Ala His Ser Gly Lys Trp Ile Asn Lys Glu Glu
            755                 760                 765

Ala Ile Met Ser Asp Leu Ser Ser Lys Glu Tyr Ile Phe Phe Asp Ser
770                 775                 780

Ile Asp Asn Lys Leu Lys Ala Lys Ser Lys Asn Ile Pro Gly Leu Ala
785                 790                 795                 800

Ser Ile Ser Glu Asp Ile Lys Thr Leu Leu Leu Asp Ala Ser Val Ser
                805                 810                 815

Pro Asp Thr Lys Phe Ile Leu Asn Asn Leu Lys Leu Asn Ile Glu Ser
            820                 825                 830

Ser Ile Gly Asp Tyr Ile Tyr Tyr Glu Lys Leu Glu Pro Val Lys Asn
            835                 840                 845

Ile Ile His Asn Ser Ile Asp Asp Leu Ile Asp Glu Phe Asn Leu Leu
            850                 855                 860

Glu Asn Val Ser Asp Glu Leu Tyr Glu Leu Lys Lys Leu Asn Asn Leu
865                 870                 875                 880

Asp Glu Lys Tyr Leu Ile Ser Phe Glu Asp Ile Ser Lys Asn Asn Ser
                885                 890                 895

Thr Tyr Ser Val Arg Phe Ile Asn Lys Ser Asn Gly Glu Ser Val Tyr
            900                 905                 910

Val Glu Thr Glu Lys Glu Ile Phe Ser Lys Tyr Ser Glu His Ile Thr
            915                 920                 925

Lys Glu Ile Ser Thr Ile Lys Asn Ser Ile Ile Thr Asp Val Asn Gly
            930                 935                 940
```

-continued

Asn Leu Leu Asp Asn Ile Gln Leu Asp His Thr Ser Gln Val Asn Thr
945                 950                 955                 960

Leu Asn Ala Ala Phe Phe Ile Gln Ser Leu Ile Asp Tyr Ser Ser Asn
            965                 970                 975

Lys Asp Val Leu Asn Asp Leu Ser Thr Ser Val Lys Val Gln Leu Tyr
            980                 985                 990

Ala Gln Leu Phe Ser Thr Gly Leu Asn Thr Ile Tyr Asp Ser Ile Gln
        995                 1000                1005

Leu Val Asn Leu Ile Ser Asn Ala Val Asn Asp Thr Ile Asn Val
    1010                1015                1020

Leu Pro Thr Ile Thr Glu Gly Ile Pro Ile Val Ser Thr Ile Leu
    1025                1030                1035

Asp Gly Ile Asn Leu Gly Ala Ala Ile Lys Glu Leu Leu Asp Glu
    1040                1045                1050

His Asp Pro Leu Leu Lys Lys Glu Leu Glu Ala Lys Val Gly Val
    1055                1060                1065

Leu Ala Ile Asn Met Ser Leu Ser Ile Ala Ala Thr Val Ala Ser
    1070                1075                1080

Ile Val Gly Ile Gly Ala Glu Val Thr Ile Phe Leu Leu Pro Ile
    1085                1090                1095

Ala Gly Ile Ser Ala Gly Ile Pro Ser Leu Val Asn Asn Glu Leu
    1100                1105                1110

Ile Leu His Asp Lys Ala Thr Ser Val Val Asn Tyr Phe Asn His
    1115                1120                1125

Leu Ser Glu Ser Lys Glu Tyr Gly Pro Leu Lys Thr Glu Asp Asp
    1130                1135                1140

Lys Ile Leu Val Pro Ile Asp Asp Leu Val Ile Ser Glu Ile Asp
    1145                1150                1155

Phe Asn Asn Asn Ser Ile Lys Leu Gly Thr Cys Asn Ile Leu Ala
    1160                1165                1170

Met Glu Gly Gly Ser Gly His Thr Val Thr Gly Asn Ile Asp His
    1175                1180                1185

Phe Phe Ser Ser Pro Tyr Ile Ser Ser His Ile Pro Ser Leu Ser
    1190                1195                1200

Val Tyr Ser Ala Ile Gly Ile Lys Thr Glu Asn Leu Asp Phe Ser
    1205                1210                1215

Lys Lys Ile Met Met Leu Pro Asn Ala Pro Ser Arg Val Phe Trp
    1220                1225                1230

Trp Glu Thr Gly Ala Val Pro Gly Leu Arg Ser Leu Glu Asn Asn
    1235                1240                1245

Gly Thr Lys Leu Leu Asp Ser Ile Arg Asp Leu Tyr Pro Gly Lys
    1250                1255                1260

Phe Tyr Trp Arg Phe Tyr Ala Phe Phe Asp Tyr Ala Ile Thr Thr
    1265                1270                1275

Leu Lys Pro Val Tyr Glu Asp Thr Asn Thr Lys Ile Lys Leu Asp
    1280                1285                1290

Lys Asp Thr Arg Asn Phe Ile Met Pro Thr Ile Thr Thr Asp Glu
    1295                1300                1305

Ile Arg Asn Lys Leu Ser Tyr Ser Phe Asp Gly Ala Gly Gly Thr
    1310                1315                1320

Tyr Ser Leu Leu Leu Ser Ser Tyr Pro Ile Ser Met Asn Ile Asn
    1325                1330                1335

Leu Ser Lys Asp Asp Leu Trp Ile Phe Asn Ile Asp Asn Glu Val

-continued

```
            1340                1345                1350

Arg Glu Ile Ser Ile Glu Asn Gly Thr Ile Lys Lys Gly Asn Leu
    1355                1360                1365

Ile Glu Asp Val Leu Ser Lys Ile Asp Ile Asn Lys Asn Lys Leu
    1370                1375                1380

Ile Ile Gly Asn Gln Thr Ile Asp Phe Ser Gly Asp Ile Asp Asn
    1385                1390                1395

Lys Asp Arg Tyr Ile Phe Leu Thr Cys Glu Leu Asp Asp Lys Ile
    1400                1405                1410

Ser Leu Ile Ile Glu Ile Asn Leu Val Ala Lys Ser Tyr Ser Leu
    1415                1420                1425

Leu Leu Ser Gly Asp Lys Asn Tyr Leu Ile Ser Asn Leu Ser Asn
    1430                1435                1440

Thr Ile Glu Lys Ile Asn Thr Leu Gly Leu Asp Ser Lys Asn Ile
    1445                1450                1455

Ala Tyr Asn Tyr Thr Asp Glu Ser Asn Asn Lys Tyr Phe Gly Ala
    1460                1465                1470

Ile Ser Lys Thr Ser Gln Lys Ser Ile Ile His Tyr Lys Lys Asp
    1475                1480                1485

Ser Lys Asn Ile Leu Glu Phe Tyr Asn Gly Ser Thr Leu Glu Phe
    1490                1495                1500

Asn Ser Lys Asp Phe Ile Ala Glu Asp Ile Asn Val Phe Met Lys
    1505                1510                1515

Asp Asp Ile Asn Thr Ile Thr Gly Lys Tyr Tyr Val Asp Asn Asn
    1520                1525                1530

Thr Asp Lys Ser Ile Asp Phe Ser Ile Ser Leu Val Ser Lys Asn
    1535                1540                1545

Gln Val Lys Val Asn Gly Leu Tyr Leu Asn Glu Ser Val Tyr Ser
    1550                1555                1560

Ser Tyr Leu Asp Phe Val Lys Asn Ser Asp Gly His His Asn Thr
    1565                1570                1575

Ser Asn Phe Met Asn Leu Phe Leu Asn Asn Ile Ser Phe Trp Lys
    1580                1585                1590

Leu Phe Gly Phe Glu Asn Ile Asn Phe Val Ile Asp Lys Tyr Phe
    1595                1600                1605

Thr Leu Val Gly Lys Thr Asn Leu Gly Tyr Val Glu Phe Ile Cys
    1610                1615                1620

Asp Asn Asn Lys Asn Ile Asp Ile Tyr Phe Gly Glu Trp Lys Thr
    1625                1630                1635

Ser Ser Ser Lys Ser Thr Ile Phe Ser Gly Asn Gly Arg Asn Val
    1640                1645                1650

Val Val Glu Pro Ile Tyr Asn Pro Asp Thr Gly Glu Asp Ile Ser
    1655                1660                1665

Thr Ser Leu Asp Phe Ser Tyr Glu Pro Leu Tyr Gly Ile Asp Arg
    1670                1675                1680

Tyr Ile Asn Lys Val Leu Ile Ala Pro Asp Leu Tyr Thr Ser Leu
    1685                1690                1695

Ile Asn Ile Asn Thr Asn Tyr Tyr Ser Asn Glu Tyr Tyr Pro Glu
    1700                1705                1710

Ile Ile Val Leu Asn Pro Asn Thr Phe His Lys Lys Val Asn Ile
    1715                1720                1725

Asn Leu Asp Ser Ser Ser Phe Glu Tyr Lys Trp Ser Thr Glu Gly
    1730                1735                1740
```

```
Ser Asp Phe Ile Leu Val Arg Tyr Leu Glu Ser Asn Lys Lys
    1745                1750            1755

Ile Leu Gln Lys Ile Arg Ile Lys Gly Ile Leu Ser Asn Thr Gln
    1760                1765            1770

Ser Phe Asn Lys Met Ser Ile Asp Phe Lys Asp Ile Lys Lys Leu
    1775                1780            1785

Ser Leu Gly Tyr Ile Met Ser Asn Phe Lys Ser Phe Asn Ser Glu
    1790                1795            1800

Asn Glu Leu Asp Arg Asp His Leu Gly Phe Lys Ile Ile Asp Asn
    1805                1810            1815

Lys Thr Tyr Tyr Tyr Asp Glu Asp Ser Lys Leu Val Lys Gly Leu
    1820                1825            1830

Ile Asn Ile Asn Asn Ser Leu Phe Tyr Phe Asp Pro Ile Glu Ser
    1835                1840            1845

Asn Leu Val Thr Gly Trp Gln Thr Ile Asn Gly Lys Lys Tyr Tyr
    1850                1855            1860

Phe Asp Ile Asn Thr Gly Ala Ala Ser Thr Ser Tyr Lys Ile Ile
    1865                1870            1875

Asn Gly Lys His Phe Tyr Phe Asn Asn Asn Gly Val Met Gln Leu
    1880                1885            1890

Gly Val Phe Lys Gly Pro Asp Gly Phe Glu Tyr Phe Ala Pro Ala
    1895                1900            1905

Asn Thr Gln Asn Asn Asn Ile Glu Gly Gln Ala Ile Val Tyr Gln
    1910                1915            1920

Ser Lys Phe Leu Thr Leu Asn Gly Lys Lys Tyr Tyr Phe Asp Asn
    1925                1930            1935

Asp Ser Lys Ala Val Thr Gly Trp Arg Ile Ile Asn Asn Glu Lys
    1940                1945            1950

Tyr Tyr Phe Asn Pro Asn Asn Ala Ile Ala Ala Val Gly Leu Gln
    1955                1960            1965

Val Ile Asp Asn Asn Lys Tyr Tyr Phe Asn Pro Asp Thr Ala Ile
    1970                1975            1980

Ile Ser Lys Gly Trp Gln Thr Val Asn Gly Ser Arg Tyr Tyr Phe
    1985                1990            1995

Asp Thr Asp Thr Ala Ile Ala Phe Asn Gly Tyr Lys Thr Ile Asp
    2000                2005            2010

Gly Lys His Phe Tyr Phe Asp Ser Asp Cys Val Val Lys Ile Gly
    2015                2020            2025

Val Phe Ser Gly Ser Asn Gly Phe Glu Tyr Phe Ala Pro Ala Asn
    2030                2035            2040

Thr Tyr Asn Asn Asn Ile Glu Gly Gln Ala Ile Val Tyr Gln Ser
    2045                2050            2055

Lys Phe Leu Thr Leu Asn Gly Lys Lys Tyr Tyr Phe Asp Asn Asn
    2060                2065            2070

Ser Lys Ala Val Thr Gly Trp Gln Thr Ile Asp Ser Lys Lys Tyr
    2075                2080            2085

Tyr Phe Asn Thr Asn Thr Ala Glu Ala Ala Thr Gly Trp Gln Thr
    2090                2095            2100

Ile Asp Gly Lys Lys Tyr Tyr Phe Asn Thr Asn Thr Ala Glu Ala
    2105                2110            2115

Ala Thr Gly Trp Gln Thr Ile Asp Gly Lys Lys Tyr Tyr Phe Asn
    2120                2125            2130
```

```
Thr Asn Thr Ser Ile Ala Ser Thr Gly Tyr Thr Ile Ile Asn Gly
    2135                2140                2145

Lys Tyr Phe Tyr Phe Asn Thr Asp Gly Ile Met Gln Ile Gly Val
    2150                2155                2160

Phe Lys Val Pro Asn Gly Phe Glu Tyr Phe Ala Pro Ala Asn Thr
    2165                2170                2175

His Asn Asn Asn Ile Glu Gly Gln Ala Ile Leu Tyr Gln Asn Lys
    2180                2185                2190

Phe Leu Thr Leu Asn Gly Lys Lys Tyr Tyr Phe Gly Ser Asp Ser
    2195                2200                2205

Lys Ala Ile Thr Gly Trp Gln Thr Ile Asp Gly Lys Lys Tyr Tyr
    2210                2215                2220

Phe Asn Pro Asn Asn Ala Ile Ala Ala Thr His Leu Cys Thr Ile
    2225                2230                2235

Asn Asn Asp Lys Tyr Tyr Phe Ser Tyr Asp Gly Ile Leu Gln Asn
    2240                2245                2250

Gly Tyr Ile Thr Ile Glu Arg Asn Asn Phe Tyr Phe Asp Ala Asn
    2255                2260                2265

Asn Glu Ser Lys Met Val Thr Gly Val Phe Lys Gly Pro Asn Gly
    2270                2275                2280

Phe Glu Tyr Phe Ala Pro Ala Asn Thr His Asn Asn Asn Ile Glu
    2285                2290                2295

Gly Gln Ala Ile Val Tyr Gln Asn Lys Phe Leu Thr Leu Asn Gly
    2300                2305                2310

Lys Lys Tyr Tyr Phe Asp Asn Asp Ser Lys Ala Val Thr Gly Trp
    2315                2320                2325

Gln Thr Ile Asp Ser Lys Lys Tyr Tyr Phe Asn Leu Asn Thr Ala
    2330                2335                2340

Val Ala Val Thr Gly Trp Gln Thr Ile Asp Gly Glu Lys Tyr Tyr
    2345                2350                2355

Phe Asn Leu Asn Thr Ala Glu Ala Ala Thr Gly Trp Gln Thr Ile
    2360                2365                2370

Asp Gly Lys Arg Tyr Tyr Phe Asn Thr Asn Thr Tyr Ile Ala Ser
    2375                2380                2385

Thr Gly Tyr Thr Ile Ile Asn Gly Lys His Phe Tyr Phe Asn Thr
    2390                2395                2400

Asp Gly Ile Met Gln Ile Gly Val Phe Lys Gly Pro Asp Gly Phe
    2405                2410                2415

Glu Tyr Phe Ala Pro Ala Asn Thr His Asn Asn Asn Ile Glu Gly
    2420                2425                2430

Gln Ala Ile Leu Tyr Gln Asn Lys Phe Leu Thr Leu Asn Gly Lys
    2435                2440                2445

Lys Tyr Tyr Phe Gly Ser Asp Ser Lys Ala Val Thr Gly Leu Arg
    2450                2455                2460

Thr Ile Asp Gly Lys Lys Tyr Tyr Phe Asn Thr Asn Thr Ala Val
    2465                2470                2475

Ala Val Thr Gly Trp Gln Thr Ile Asn Gly Lys Lys Tyr Tyr Phe
    2480                2485                2490

Asn Thr Asn Thr Tyr Ile Ala Ser Thr Gly Tyr Thr Ile Ile Ser
    2495                2500                2505

Gly Lys His Phe Tyr Phe Asn Thr Asp Gly Ile Met Gln Ile Gly
    2510                2515                2520

Val Phe Lys Gly Pro Asp Gly Phe Glu Tyr Phe Ala Pro Ala Asn
```

```
              2525                2530                2535

Thr  Asp  Ala  Asn  Asn  Ile  Glu  Gly  Gln  Ala  Ile  Arg  Tyr  Gln  Asn
          2540                2545                2550

Arg  Phe  Leu  Tyr  Leu  His  Asp  Asn  Ile  Tyr  Tyr  Phe  Gly  Asn  Asp
     2555                2560                2565

Ser  Lys  Ala  Ala  Thr  Gly  Trp  Ala  Thr  Ile  Asp  Gly  Asn  Arg  Tyr
     2570                2575                2580

Tyr  Phe  Glu  Pro  Asn  Thr  Ala  Met  Gly  Ala  Asn  Gly  Tyr  Lys  Thr
     2585                2590                2595

Ile  Asp  Asn  Lys  Asn  Phe  Tyr  Phe  Arg  Asn  Gly  Leu  Pro  Gln  Ile
     2600                2605                2610

Gly  Val  Phe  Lys  Gly  Pro  Asn  Gly  Phe  Glu  Tyr  Phe  Ala  Pro  Ala
     2615                2620                2625

Asn  Thr  Asp  Ala  Asn  Asn  Ile  Asp  Gly  Gln  Ala  Ile  Arg  Tyr  Gln
     2630                2635                2640

Asn  Arg  Phe  Leu  His  Leu  Leu  Gly  Lys  Ile  Tyr  Tyr  Phe  Gly  Asn
     2645                2650                2655

Asn  Ser  Lys  Ala  Val  Thr  Gly  Trp  Gln  Thr  Ile  Asn  Ser  Lys  Val
     2660                2665                2670

Tyr  Tyr  Phe  Met  Pro  Asp  Thr  Ala  Met  Ala  Ala  Ala  Gly  Gly  Leu
     2675                2680                2685

Phe  Glu  Ile  Asp  Gly  Val  Ile  Tyr  Phe  Phe  Gly  Val  Asp  Gly  Val
     2690                2695                2700

Lys  Ala  Pro  Gly  Ile  Tyr  Gly
     2705                2710

<210> SEQ ID NO 4
<211> LENGTH: 2366
<212> TYPE: PRT
<213> ORGANISM: Artificial Sequence
<220> FEATURE:
<223> OTHER INFORMATION: C. difficile Toxin B (Toxinotype 3)

<400> SEQUENCE: 4

Met  Ser  Leu  Val  Asn  Arg  Lys  Gln  Leu  Glu  Lys  Met  Ala  Asn  Val  Arg
1                 5                   10                  15

Phe  Arg  Val  Gln  Glu  Asp  Glu  Tyr  Val  Ala  Ile  Leu  Asp  Ala  Leu  Glu
                 20                  25                  30

Glu  Tyr  His  Asn  Met  Ser  Glu  Asn  Thr  Val  Val  Glu  Lys  Tyr  Leu  Lys
             35                  40                  45

Leu  Lys  Asp  Ile  Asn  Ser  Leu  Thr  Asp  Ile  Tyr  Ile  Asp  Thr  Tyr  Lys
50                  55                  60

Lys  Ser  Gly  Arg  Asn  Lys  Ala  Leu  Lys  Lys  Phe  Lys  Glu  Tyr  Leu  Val
65                  70                  75                  80

Thr  Glu  Val  Leu  Glu  Leu  Lys  Asn  Asn  Asn  Leu  Thr  Pro  Val  Glu  Lys
                 85                  90                  95

Asn  Leu  His  Phe  Val  Trp  Ile  Gly  Gly  Gln  Ile  Asn  Asp  Thr  Ala  Ile
             100                 105                 110

Asn  Tyr  Ile  Asn  Gln  Trp  Lys  Asp  Val  Asn  Ser  Asp  Tyr  Asn  Val  Asn
             115                 120                 125

Val  Phe  Tyr  Asp  Ser  Asn  Ala  Phe  Leu  Ile  Asn  Thr  Leu  Lys  Lys  Thr
             130                 135                 140

Ile  Val  Glu  Ser  Ala  Thr  Asn  Asp  Thr  Leu  Glu  Ser  Phe  Arg  Glu  Asn
145                 150                 155                 160

Leu  Asn  Asp  Pro  Arg  Phe  Asp  Tyr  Asn  Lys  Phe  Tyr  Arg  Lys  Arg  Met
```

```
                    165                 170                 175
Glu Ile Ile Tyr Asp Lys Gln Lys Asn Phe Ile Asn Tyr Tyr Lys Thr
                180                 185                 190

Gln Arg Glu Glu Asn Pro Asp Leu Ile Ile Asp Asp Ile Val Lys Ile
            195                 200                 205

Tyr Leu Ser Asn Glu Tyr Ser Lys Asp Ile Asp Glu Leu Asn Ser Tyr
        210                 215                 220

Ile Glu Glu Ser Leu Asn Lys Val Thr Glu Asn Ser Gly Asn Asp Val
225                 230                 235                 240

Arg Asn Phe Glu Glu Phe Lys Gly Gly Glu Ser Phe Lys Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Val Gly Val Tyr Leu Asp Val Asp
        275                 280                 285

Met Leu Pro Gly Ile Gln Pro Asp Leu Phe Glu Ser Ile Glu Lys Pro
    290                 295                 300

Ser Ser Val Thr Val Asp Phe Trp Glu Met Val Lys Leu Glu Ala Ile
305                 310                 315                 320

Met Lys Tyr Lys Glu Tyr Ile Pro Gly Tyr Thr Ser Glu His Phe Asp
                325                 330                 335

Met Leu Asp Glu Glu Val Gln Ser Ser Phe Glu Ser Val Leu Ala Ser
            340                 345                 350

Lys Ser Asp Lys Ser Glu Ile Phe Ser Ser Leu Gly Asp Met Glu Ala
        355                 360                 365

Ser Pro Leu Glu Val Lys Ile Ala Phe Asn Ser Lys Gly Ile Ile Asn
    370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Ala Phe Ile
            420                 425                 430

Asp Ser Ile Met Ala Glu Ala Asn Ala Asp Asn Gly Arg Phe Met Met
        435                 440                 445

Glu Leu Gly Lys Tyr Leu Arg Val Gly Phe Phe Pro Asp Val Lys Thr
    450                 455                 460

Thr Ile Asn Leu Ser Gly Pro Glu Ala Tyr Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
            500                 505                 510

Glu Gln Glu Met Ala Ser Leu Trp Ser Phe Asp Ala Arg Ala Lys
        515                 520                 525

Ala Gln Phe Glu Glu Tyr Lys Lys Asn Tyr Phe Glu Gly Ser Leu Gly
    530                 535                 540

Glu Asp Asp Asn Leu Asp Phe Ser Gln Asn Thr Val Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
            580                 585                 590
```

-continued

```
Ala Ala Cys Asn Leu Phe Ala Lys Thr Pro Tyr Asp Ser Val Leu Phe
        595                 600                 605

Gln Lys Asn Ile Glu Asp Ser Glu Ile Ala Tyr Tyr Tyr Asn Pro Gly
        610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
            645                 650                 655

Glu Phe Asn Thr Asp Ile Phe Ala Gly Leu Asp Val Asp Ser Leu Ser
            660                 665                 670

Thr Glu Ile Glu Thr Ala Ile Asp Leu Ala Lys Glu Asp Ile Ser Pro
            675                 680                 685

Lys Ser Ile Glu Ile Asn Leu Leu Gly Cys Asn Met Phe Ser Tyr Ser
            690                 695                 700

Val Asn Val Glu Glu Thr Tyr Pro Gly Lys Leu Leu Leu Arg Val Lys
705                 710                 715                 720

Asp Lys Val Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
                740                 745                 750

Glu Leu Leu Asp His Ser Gly Glu Trp Ile Asn Lys Glu Glu Ser Ile
            755                 760                 765

Ile Lys Asp Ile Ser Ser Lys Glu Tyr Ile Ser Phe Asn Pro Lys Glu
            770                 775                 780

Asn Lys Ile Ile Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
                805                 810                 815

Glu Lys Val Met Leu Ala Glu Cys Glu Ile Asn Val Ile Ser Asn Ile
                820                 825                 830

Asp Thr Gln Val Val Glu Gly Arg Ile Glu Glu Ala Lys Ser Leu Thr
        835                 840                 845

Ser Asp Ser Ile Asn Tyr Ile Lys Asn Glu Phe Lys Leu Ile Glu Ser
850                 855                 860

Ile Ser Asp Ala Leu Tyr Asp Leu Lys Gln Gln Asn Glu Leu Glu Glu
865                 870                 875                 880

Ser His Phe Ile Ser Phe Glu Asp Ile Leu Glu Thr Asp Glu Gly Phe
            885                 890                 895

Ser Ile Arg Phe Ile Asp Lys Glu Thr Gly Glu Ser Ile Phe Val Glu
            900                 905                 910

Thr Glu Lys Ala Ile Phe Ser Gly Tyr Ala Asn His Ile Thr Glu Glu
            915                 920                 925

Ile Ser Lys Ile Lys Gly Thr Ile Phe Asp Thr Val Asn Gly Lys Leu
            930                 935                 940

Val Lys Lys Val Asn Leu Asp Ala Thr His Glu Val Asn Thr Leu Asn
945                 950                 955                 960

Ala Ala Phe Phe Ile Gln Ser Leu Ile Glu Tyr Asn Ser Ser Lys Glu
                965                 970                 975

Ser Leu Ser Asn Leu Ser Val Ala Met Lys Val Gln Val Tyr Ala Gln
            980                 985                 990

Leu Phe Ser Thr Gly Leu Asn Thr Ile Thr Asp Ala Ala Lys Val Val
            995                 1000                1005
```

-continued

| | | | | | | | | | | |
|---|---|---|---|---|---|---|---|---|---|---|
|Glu|Leu|Val|Ser|Thr|Ala|Leu|Asp|Glu|Thr|Ile|Asp|Leu|Leu|Pro|
|1010| | | | |1015| | | | |1020| | | | |

Thr Leu Ser Glu Gly Leu Pro Val Ile Ala Thr Ile Ile Asp Gly
1025                    1030                    1035

Val Ser Leu Gly Ala Ala Ile Lys Glu Leu Ser Glu Thr Ser Asp
1040                    1045                    1050

Pro Leu Leu Arg Gln Glu Ile Glu Ala Lys Ile Gly Ile Met Ala
1055                    1060                    1065

Val Asn Leu Thr Ala Ala Thr Ala Ile Ile Thr Ser Ser Leu
1070                    1075                    1080

Gly Ile Ala Ser Gly Phe Ser Ile Leu Leu Val Pro Leu Ala Gly
1085                    1090                    1095

Ile Ser Ala Gly Ile Pro Ser Leu Val Asn Asn Glu Leu Ile Leu
1100                    1105                    1110

Arg Asp Lys Ala Thr Lys Val Val Asp Tyr Phe Ser His Ile Ser
1115                    1120                    1125

Leu Ala Glu Ser Glu Gly Ala Phe Thr Ser Leu Asp Asp Lys Ile
1130                    1135                    1140

Met Met Pro Gln Asp Asp Leu Val Ile Ser Glu Ile Asp Phe Asn
1145                    1150                    1155

Asn Asn Ser Ile Thr Leu Gly Lys Cys Glu Ile Trp Arg Met Glu
1160                    1165                    1170

Gly Gly Ser Gly His Thr Val Thr Asp Asp Ile Asp His Phe Phe
1175                    1180                    1185

Ser Ala Pro Ser Ile Thr Tyr Arg Glu Pro His Leu Ser Ile Tyr
1190                    1195                    1200

Asp Val Leu Glu Val Gln Lys Glu Glu Leu Asp Leu Ser Lys Asp
1205                    1210                    1215

Leu Met Val Leu Pro Asn Ala Pro Asn Arg Val Phe Ala Trp Glu
1220                    1225                    1230

Thr Gly Trp Thr Pro Gly Leu Arg Ser Leu Glu Asn Asp Gly Thr
1235                    1240                    1245

Lys Leu Leu Asp Arg Ile Arg Asp Asn Tyr Glu Gly Glu Phe Tyr
1250                    1255                    1260

Trp Arg Tyr Phe Ala Phe Ile Ala Asp Ala Leu Ile Thr Thr Leu
1265                    1270                    1275

Lys Pro Arg Tyr Glu Asp Thr Asn Ile Arg Ile Asn Leu Asp Ser
1280                    1285                    1290

Asn Thr Arg Ser Phe Ile Val Pro Val Ile Thr Thr Glu Tyr Ile
1295                    1300                    1305

Arg Glu Lys Leu Ser Tyr Ser Phe Tyr Gly Ser Gly Gly Thr Tyr
1310                    1315                    1320

Ala Leu Ser Leu Ser Gln Tyr Asn Met Asn Ile Asn Ile Glu Leu
1325                    1330                    1335

Asn Glu Asn Asp Thr Trp Val Ile Asp Val Asp Asn Val Val Arg
1340                    1345                    1350

Asp Val Thr Ile Glu Ser Asp Lys Ile Lys Lys Gly Asp Leu Ile
1355                    1360                    1365

Glu Asn Ile Leu Ser Lys Leu Ser Ile Glu Asp Asn Lys Ile Ile
1370                    1375                    1380

Leu Asp Asn His Glu Ile Asn Phe Ser Gly Thr Leu Asn Gly Gly
1385                    1390                    1395

Asn Gly Phe Val Ser Leu Thr Phe Ser Ile Leu Glu Gly Ile Asn

-continued

```
             1400                1405                1410

Ala Val Ile Glu Val Asp Leu Leu Ser Lys Ser Tyr Lys Val Leu
    1415                1420                1425

Ile Ser Gly Glu Leu Lys Thr Leu Met Ala Asn Ser Asn Ser Val
    1430                1435                1440

Gln Gln Lys Ile Asp Tyr Ile Gly Leu Asn Ser Glu Leu Gln Lys
    1445                1450                1455

Asn Ile Pro Tyr Ser Phe Met Asp Asp Lys Gly Lys Glu Asn Gly
    1460                1465                1470

Phe Ile Asn Cys Ser Thr Lys Glu Gly Leu Phe Val Ser Glu Leu
    1475                1480                1485

Ser Asp Val Val Leu Ile Ser Lys Val Tyr Met Asp Asn Ser Lys
    1490                1495                1500

Pro Leu Phe Gly Tyr Cys Ser Asn Asp Leu Lys Asp Val Lys Val
    1505                1510                1515

Ile Thr Lys Asp Asp Val Ile Ile Leu Thr Gly Tyr Tyr Leu Lys
    1520                1525                1530

Asp Asp Ile Lys Ile Ser Leu Ser Phe Thr Ile Gln Asp Glu Asn
    1535                1540                1545

Thr Ile Lys Leu Asn Gly Val Tyr Leu Asp Glu Asn Gly Val Ala
    1550                1555                1560

Glu Ile Leu Lys Phe Met Asn Lys Lys Gly Ser Thr Asn Thr Ser
    1565                1570                1575

Asp Ser Leu Met Ser Phe Leu Glu Ser Met Asn Ile Lys Ser Ile
    1580                1585                1590

Phe Ile Asn Ser Leu Gln Ser Asn Thr Lys Leu Ile Leu Asp Thr
    1595                1600                1605

Asn Phe Ile Ile Ser Gly Thr Thr Ser Ile Gly Gln Phe Glu Phe
    1610                1615                1620

Ile Cys Asp Lys Asp Asn Asn Ile Gln Pro Tyr Phe Ile Lys Phe
    1625                1630                1635

Asn Thr Leu Glu Thr Lys Tyr Thr Leu Tyr Val Gly Asn Arg Gln
    1640                1645                1650

Asn Met Ile Val Glu Pro Asn Tyr Asp Leu Asp Asp Ser Gly Asp
    1655                1660                1665

Ile Ser Ser Thr Val Ile Asn Phe Ser Gln Lys Tyr Leu Tyr Gly
    1670                1675                1680

Ile Asp Ser Cys Val Asn Lys Val Ile Ile Ser Pro Asn Ile Tyr
    1685                1690                1695

Thr Asp Glu Ile Asn Ile Thr Pro Ile Tyr Glu Ala Asn Asn Thr
    1700                1705                1710

Tyr Pro Glu Val Ile Val Leu Asp Thr Asn Tyr Ile Ser Glu Lys
    1715                1720                1725

Ile Asn Ile Asn Ile Asn Asp Leu Ser Ile Arg Tyr Val Trp Ser
    1730                1735                1740

Asn Asp Gly Ser Asp Phe Ile Leu Met Ser Thr Asp Glu Glu Asn
    1745                1750                1755

Lys Val Ser Gln Val Lys Ile Arg Phe Thr Asn Val Phe Lys Gly
    1760                1765                1770

Asn Thr Ile Ser Asp Lys Ile Ser Phe Asn Phe Ser Asp Lys Gln
    1775                1780                1785

Asp Val Ser Ile Asn Lys Val Ile Ser Thr Phe Thr Pro Ser Tyr
    1790                1795                1800
```

```
Tyr Val Glu Gly Leu Leu Asn Tyr Asp Leu Gly Leu Ile Ser Leu
    1805                1810                1815

Tyr Asn Glu Lys Phe Tyr Ile Asn Asn Phe Gly Met Met Val Ser
    1820                1825                1830

Gly Leu Val Tyr Ile Asn Asp Ser Leu Tyr Tyr Phe Lys Pro Pro
    1835                1840                1845

Ile Lys Asn Leu Ile Thr Gly Phe Thr Thr Ile Gly Asp Asp Lys
    1850                1855                1860

Tyr Tyr Phe Asn Pro Asp Asn Gly Gly Ala Ala Ser Val Gly Glu
    1865                1870                1875

Thr Ile Ile Asp Gly Lys Asn Tyr Tyr Phe Ser Gln Asn Gly Val
    1880                1885                1890

Leu Gln Thr Gly Val Phe Ser Thr Glu Asp Gly Phe Lys Tyr Phe
    1895                1900                1905

Ala Pro Ala Asp Thr Leu Asp Glu Asn Leu Glu Gly Glu Ala Ile
    1910                1915                1920

Asp Phe Thr Gly Lys Leu Thr Ile Asp Glu Asn Val Tyr Tyr Phe
    1925                1930                1935

Gly Asp Asn Tyr Arg Ala Ala Ile Glu Trp Gln Thr Leu Asp Asp
    1940                1945                1950

Glu Val Tyr Tyr Phe Ser Thr Asp Thr Gly Arg Ala Phe Lys Gly
    1955                1960                1965

Leu Asn Gln Ile Gly Asp Asp Lys Phe Tyr Phe Asn Ser Asp Gly
    1970                1975                1980

Ile Met Gln Lys Gly Phe Val Asn Ile Asn Asp Lys Thr Phe Tyr
    1985                1990                1995

Phe Asp Asp Ser Gly Val Met Lys Ser Gly Tyr Thr Glu Ile Asp
    2000                2005                2010

Gly Lys Tyr Phe Tyr Phe Ala Glu Asn Gly Glu Met Gln Ile Gly
    2015                2020                2025

Val Phe Asn Thr Ala Asp Gly Phe Lys Tyr Phe Ala His His Asp
    2030                2035                2040

Glu Asp Leu Gly Asn Glu Glu Gly Glu Ala Leu Ser Tyr Ser Gly
    2045                2050                2055

Ile Leu Asn Phe Asn Asn Lys Ile Tyr Tyr Phe Asp Asp Ser Phe
    2060                2065                2070

Thr Ala Val Val Gly Trp Lys Asp Leu Glu Asp Gly Ser Lys Tyr
    2075                2080                2085

Tyr Phe Asp Glu Asp Thr Ala Glu Ala Tyr Ile Gly Ile Ser Ile
    2090                2095                2100

Ile Asn Asp Gly Lys Tyr Tyr Phe Asn Asp Ser Gly Ile Met Gln
    2105                2110                2115

Ile Gly Phe Val Thr Ile Asn Asn Glu Val Phe Tyr Phe Ser Asp
    2120                2125                2130

Ser Gly Ile Val Glu Ser Gly Met Gln Asn Ile Asp Asp Asn Tyr
    2135                2140                2145

Phe Tyr Ile Asp Glu Asn Gly Leu Val Gln Ile Gly Val Phe Asp
    2150                2155                2160

Thr Ser Asp Gly Tyr Lys Tyr Phe Ala Pro Ala Asn Thr Val Asn
    2165                2170                2175

Asp Asn Ile Tyr Gly Gln Ala Val Glu Tyr Ser Gly Leu Val Arg
    2180                2185                2190
```

```
Val Gly Glu Asp Val Tyr Tyr Phe Gly Glu Thr Tyr Thr Ile Glu
    2195                2200                2205

Thr Gly Trp Ile Tyr Asp Met Glu Asn Glu Ser Asp Lys Tyr Tyr
    2210                2215                2220

Phe Asp Pro Glu Thr Lys Lys Ala Tyr Lys Gly Ile Asn Val Ile
    2225                2230                2235

Asp Asp Ile Lys Tyr Tyr Phe Asp Glu Asn Gly Ile Met Arg Thr
    2240                2245                2250

Gly Leu Ile Thr Phe Glu Asp Asn His Tyr Tyr Phe Asn Glu Asp
    2255                2260                2265

Gly Ile Met Gln Tyr Gly Tyr Leu Asn Ile Glu Asp Lys Thr Phe
    2270                2275                2280

Tyr Phe Ser Glu Asp Gly Ile Met Gln Ile Gly Val Phe Asn Thr
    2285                2290                2295

Pro Asp Gly Phe Lys Tyr Phe Ala His Gln Asn Thr Leu Asp Glu
    2300                2305                2310

Asn Phe Glu Gly Glu Ser Ile Asn Tyr Thr Gly Trp Leu Asp Leu
    2315                2320                2325

Asp Glu Lys Arg Tyr Tyr Phe Thr Asp Glu Tyr Ile Ala Ala Thr
    2330                2335                2340

Gly Ser Val Ile Ile Asp Gly Glu Glu Tyr Tyr Phe Asp Pro Asp
    2345                2350                2355

Thr Ala Gln Leu Val Ile Ser Glu
    2360                2365

<210> SEQ ID NO 5
<211> LENGTH: 1309
<212> TYPE: PRT
<213> ORGANISM: Artificial Sequence
<220> FEATURE:
<223> OTHER INFORMATION: C. difficile Toxin A 542-1850 (toxinotype 0)

<400> SEQUENCE: 5

Leu Ser Glu Asp Asn Gly Val Asp Phe Asn Lys Asn Thr Ala Leu Asp
1               5                   10                  15

Lys Asn Tyr Leu Leu Asn Asn Lys Ile Pro Ser Asn Asn Val Glu Glu
            20                  25                  30

Ala Gly Ser Lys Asn Tyr Val His Tyr Ile Ile Gln Leu Gln Gly Asp
        35                  40                  45

Asp Ile Ser Tyr Glu Ala Thr Cys Asn Leu Phe Ser Lys Asn Pro Lys
    50                  55                  60

Asn Ser Ile Ile Ile Gln Arg Asn Met Asn Glu Ser Ala Lys Ser Tyr
65                  70                  75                  80

Phe Leu Ser Asp Asp Gly Glu Ser Ile Leu Glu Leu Asn Lys Tyr Arg
                85                  90                  95

Ile Pro Glu Arg Leu Lys Asn Lys Glu Lys Val Lys Val Thr Phe Ile
            100                 105                 110

Gly His Gly Lys Asp Glu Phe Asn Thr Ser Glu Phe Ala Arg Leu Ser
        115                 120                 125

Val Asp Ser Leu Ser Asn Glu Ile Ser Ser Phe Leu Asp Thr Ile Lys
    130                 135                 140

Leu Asp Ile Ser Pro Lys Asn Val Glu Val Asn Leu Leu Gly Cys Asn
145                 150                 155                 160

Met Phe Ser Tyr Asp Phe Asn Val Glu Glu Thr Tyr Pro Gly Lys Leu
                165                 170                 175
```

```
Leu Leu Ser Ile Met Asp Lys Ile Thr Ser Thr Leu Pro Asp Val Asn
            180                 185                 190

Lys Asn Ser Ile Thr Ile Gly Ala Asn Gln Tyr Glu Val Arg Ile Asn
        195                 200                 205

Ser Glu Gly Arg Lys Glu Leu Leu Ala His Ser Gly Lys Trp Ile Asn
    210                 215                 220

Lys Glu Glu Ala Ile Met Ser Asp Leu Ser Ser Lys Glu Tyr Ile Phe
225                 230                 235                 240

Phe Asp Ser Ile Asp Asn Lys Leu Lys Ala Lys Ser Lys Asn Ile Pro
                245                 250                 255

Gly Leu Ala Ser Ile Ser Glu Asp Ile Lys Thr Leu Leu Asp Ala
            260                 265                 270

Ser Val Ser Pro Asp Thr Lys Phe Ile Leu Asn Asn Leu Lys Leu Asn
        275                 280                 285

Ile Glu Ser Ser Ile Gly Asp Tyr Ile Tyr Tyr Glu Lys Leu Glu Pro
    290                 295                 300

Val Lys Asn Ile Ile His Asn Ser Ile Asp Asp Leu Ile Asp Glu Phe
305                 310                 315                 320

Asn Leu Leu Glu Asn Val Ser Asp Glu Leu Tyr Glu Leu Lys Lys Leu
                325                 330                 335

Asn Asn Leu Asp Glu Lys Tyr Leu Ile Ser Phe Glu Asp Ile Ser Lys
            340                 345                 350

Asn Asn Ser Thr Tyr Ser Val Arg Phe Ile Asn Lys Ser Asn Gly Glu
        355                 360                 365

Ser Val Tyr Val Glu Thr Glu Lys Glu Ile Phe Ser Lys Tyr Ser Glu
    370                 375                 380

His Ile Thr Lys Glu Ile Ser Thr Ile Lys Asn Ser Ile Ile Thr Asp
385                 390                 395                 400

Val Asn Gly Asn Leu Leu Asp Asn Ile Gln Leu Asp His Thr Ser Gln
                405                 410                 415

Val Asn Thr Leu Asn Ala Ala Phe Phe Ile Gln Ser Leu Ile Asp Tyr
            420                 425                 430

Ser Ser Asn Lys Asp Val Leu Asn Asp Leu Ser Thr Ser Val Lys Val
        435                 440                 445

Gln Leu Tyr Ala Gln Leu Phe Ser Thr Gly Leu Asn Thr Ile Tyr Asp
    450                 455                 460

Ser Ile Gln Leu Val Asn Leu Ile Ser Asn Ala Val Asn Asp Thr Ile
465                 470                 475                 480

Asn Val Leu Pro Thr Ile Thr Glu Gly Ile Pro Ile Val Ser Thr Ile
                485                 490                 495

Leu Asp Gly Ile Asn Leu Gly Ala Ala Ile Lys Glu Leu Leu Asp Glu
            500                 505                 510

His Asp Pro Leu Leu Lys Lys Glu Leu Glu Ala Lys Val Gly Val Leu
        515                 520                 525

Ala Ile Asn Met Ser Leu Ser Ile Ala Ala Thr Val Ala Ser Ile Val
    530                 535                 540

Gly Ile Gly Ala Glu Val Thr Ile Phe Leu Leu Pro Ile Ala Gly Ile
545                 550                 555                 560

Ser Ala Gly Ile Pro Ser Leu Val Asn Asn Glu Leu Ile Leu His Asp
                565                 570                 575

Lys Ala Thr Ser Val Val Asn Tyr Phe Asn His Leu Ser Glu Ser Lys
            580                 585                 590

Lys Tyr Gly Pro Leu Lys Thr Glu Asp Asp Lys Ile Leu Val Pro Ile
```

```
           595                 600                 605
Asp Asp Leu Val Ile Ser Glu Ile Asp Phe Asn Asn Ser Ile Lys
610                 615                 620

Leu Gly Thr Cys Asn Ile Leu Ala Met Glu Gly Ser Gly His Thr
625                 630                 635                 640

Val Thr Gly Asn Ile Asp His Phe Phe Ser Ser Pro Ser Ile Ser Ser
                645                 650                 655

His Ile Pro Ser Leu Ser Ile Tyr Ser Ala Ile Gly Ile Glu Thr Glu
                660                 665                 670

Asn Leu Asp Phe Ser Lys Lys Ile Met Met Leu Pro Asn Ala Pro Ser
                675                 680                 685

Arg Val Phe Trp Trp Glu Thr Gly Ala Val Pro Gly Leu Arg Ser Leu
690                 695                 700

Glu Asn Asp Gly Thr Arg Leu Leu Asp Ser Ile Arg Asp Leu Tyr Pro
705                 710                 715                 720

Gly Lys Phe Tyr Trp Arg Phe Tyr Ala Phe Phe Asp Tyr Ala Ile Thr
                725                 730                 735

Thr Leu Lys Pro Val Tyr Glu Asp Thr Asn Ile Lys Ile Lys Leu Asp
                740                 745                 750

Lys Asp Thr Arg Asn Phe Ile Met Pro Thr Ile Thr Thr Asn Glu Ile
                755                 760                 765

Arg Asn Lys Leu Ser Tyr Ser Phe Asp Gly Ala Gly Gly Thr Tyr Ser
770                 775                 780

Leu Leu Leu Ser Ser Tyr Pro Ile Ser Thr Asn Ile Asn Leu Ser Lys
785                 790                 795                 800

Asp Asp Leu Trp Ile Phe Asn Ile Asp Asn Glu Val Arg Glu Ile Ser
                805                 810                 815

Ile Glu Asn Gly Thr Ile Lys Lys Gly Lys Leu Ile Lys Asp Val Leu
                820                 825                 830

Ser Lys Ile Asp Ile Asn Lys Asn Lys Leu Ile Ile Gly Asn Gln Thr
                835                 840                 845

Ile Asp Phe Ser Gly Asp Ile Asp Asn Lys Asp Arg Tyr Ile Phe Leu
850                 855                 860

Thr Cys Glu Leu Asp Asp Lys Ile Ser Leu Ile Ile Glu Ile Asn Leu
865                 870                 875                 880

Val Ala Lys Ser Tyr Ser Leu Leu Leu Ser Gly Asp Lys Asn Tyr Leu
                885                 890                 895

Ile Ser Asn Leu Ser Asn Thr Ile Glu Lys Ile Asn Thr Leu Gly Leu
                900                 905                 910

Asp Ser Lys Asn Ile Ala Tyr Asn Tyr Thr Asp Glu Ser Asn Asn Lys
                915                 920                 925

Tyr Phe Gly Ala Ile Ser Lys Thr Ser Gln Lys Ser Ile Ile His Tyr
                930                 935                 940

Lys Lys Asp Ser Lys Asn Ile Leu Glu Phe Tyr Asn Asp Ser Thr Leu
945                 950                 955                 960

Glu Phe Asn Ser Lys Asp Phe Ile Ala Glu Asp Ile Asn Val Phe Met
                965                 970                 975

Lys Asp Asp Ile Asn Thr Ile Thr Gly Lys Tyr Tyr Val Asp Asn Asn
                980                 985                 990

Thr Asp Lys Ser Ile Asp Phe Ser Ile Ser Leu Val Ser Lys Asn Gln
                995                 1000                1005

Val Lys  Val Asn Gly Leu Tyr  Leu Asn Glu Ser Val  Tyr Ser Ser
    1010                1015                1020
```

```
Tyr Leu Asp Phe Val Lys Asn Ser Asp Gly His His Asn Thr Ser
    1025                1030                1035

Asn Phe Met Asn Leu Phe Leu Asp Asn Ile Ser Phe Trp Lys Leu
    1040                1045                1050

Phe Gly Phe Glu Asn Ile Asn Phe Val Ile Asp Lys Tyr Phe Thr
    1055                1060                1065

Leu Val Gly Lys Thr Asn Leu Gly Tyr Val Glu Phe Ile Cys Asp
    1070                1075                1080

Asn Asn Lys Asn Ile Asp Ile Tyr Phe Gly Glu Trp Lys Thr Ser
    1085                1090                1095

Ser Ser Lys Ser Thr Ile Phe Ser Gly Asn Gly Arg Asn Val Val
    1100                1105                1110

Val Glu Pro Ile Tyr Asn Pro Asp Thr Gly Glu Asp Ile Ser Thr
    1115                1120                1125

Ser Leu Asp Phe Ser Tyr Glu Pro Leu Tyr Gly Ile Asp Arg Tyr
    1130                1135                1140

Ile Asn Lys Val Leu Ile Ala Pro Asp Leu Tyr Thr Ser Leu Ile
    1145                1150                1155

Asn Ile Asn Thr Asn Tyr Tyr Ser Asn Glu Tyr Tyr Pro Glu Ile
    1160                1165                1170

Ile Val Leu Asn Pro Asn Thr Phe His Lys Lys Val Asn Ile Asn
    1175                1180                1185

Leu Asp Ser Ser Ser Phe Glu Tyr Lys Trp Ser Thr Glu Gly Ser
    1190                1195                1200

Asp Phe Ile Leu Val Arg Tyr Leu Glu Glu Ser Asn Lys Lys Ile
    1205                1210                1215

Leu Gln Lys Ile Arg Ile Lys Gly Ile Leu Ser Asn Thr Gln Ser
    1220                1225                1230

Phe Asn Lys Met Ser Ile Asp Phe Lys Asp Ile Lys Lys Leu Ser
    1235                1240                1245

Leu Gly Tyr Ile Met Ser Asn Phe Lys Ser Phe Asn Ser Glu Asn
    1250                1255                1260

Glu Leu Asp Arg Asp His Leu Gly Phe Lys Ile Ile Asp Asn Lys
    1265                1270                1275

Thr Tyr Tyr Tyr Asp Glu Asp Ser Lys Leu Val Lys Gly Leu Ile
    1280                1285                1290

Asn Ile Asn Asn Ser Leu Phe Tyr Phe Asp Pro Ile Glu Phe Asn
    1295                1300                1305

Leu
```

<210> SEQ ID NO 6
<211> LENGTH: 1309
<212> TYPE: PRT
<213> ORGANISM: Artificial Sequence
<220> FEATURE:
<223> OTHER INFORMATION: C. difficile Toxin A 542-1850 (toxinotype 3)

<400> SEQUENCE: 6

```
Leu Ser Glu Asp Asn Gly Val Asp Phe Asn Lys Asn Thr Ala Leu Asp
1               5                   10                  15

Lys Asn Tyr Leu Leu Asn Asn Lys Ile Pro Ser Asn Asn Val Glu Glu
                20                  25                  30

Ala Gly Ser Lys Asn Tyr Val His Tyr Ile Ile Gln Leu Gln Gly Asp
            35                  40                  45
```

-continued

```
Asp Ile Ser Tyr Glu Ala Thr Cys Asn Leu Phe Ser Lys Asn Pro Lys
 50                  55                  60

Asn Ser Ile Ile Ile Gln Arg Asn Met Asn Glu Ser Ala Lys Ser Tyr
 65                  70                  75                  80

Phe Leu Ser Asp Asp Gly Glu Ser Ile Leu Glu Leu Asn Lys Tyr Arg
                 85                  90                  95

Ile Pro Glu Arg Leu Lys Asn Lys Glu Lys Val Lys Val Thr Phe Ile
            100                 105                 110

Gly His Gly Lys Asp Glu Phe Asn Thr Ser Glu Phe Ala Arg Leu Ser
        115                 120                 125

Val Asp Ser Leu Ser Asn Glu Ile Ser Ser Phe Leu Asp Thr Ile Lys
130                 135                 140

Leu Asp Ile Ser Pro Lys Asn Val Glu Val Asn Leu Leu Gly Cys Asn
145                 150                 155                 160

Met Phe Ser Tyr Asp Phe Asn Val Glu Glu Thr Tyr Pro Gly Lys Leu
                165                 170                 175

Leu Leu Ser Ile Met Asp Lys Ile Thr Ser Thr Leu Pro Asp Val Asn
            180                 185                 190

Lys Asp Ser Ile Thr Ile Gly Ala Asn Gln Tyr Glu Val Arg Ile Asn
        195                 200                 205

Ser Glu Gly Arg Lys Glu Leu Leu Ala His Ser Gly Lys Trp Ile Asn
210                 215                 220

Lys Glu Glu Ala Ile Met Ser Asp Leu Ser Ser Lys Glu Tyr Ile Phe
225                 230                 235                 240

Phe Asp Ser Ile Asp Asn Lys Leu Lys Ala Lys Ser Lys Asn Ile Pro
                245                 250                 255

Gly Leu Ala Ser Ile Ser Glu Asp Ile Lys Thr Leu Leu Asp Ala
            260                 265                 270

Ser Val Ser Pro Asp Thr Lys Phe Ile Leu Asn Asn Leu Lys Leu Asn
                275                 280                 285

Ile Glu Ser Ser Ile Gly Asp Tyr Ile Tyr Glu Lys Leu Glu Pro
            290                 295                 300

Val Lys Asn Ile Ile His Asn Ser Ile Asp Asp Leu Ile Asp Glu Phe
305                 310                 315                 320

Asn Leu Leu Glu Asn Val Ser Asp Glu Leu Tyr Glu Leu Lys Lys Leu
                325                 330                 335

Asn Asn Leu Asp Glu Lys Tyr Leu Ile Ser Phe Glu Asp Ile Ser Lys
            340                 345                 350

Asn Asn Ser Thr Tyr Ser Val Arg Phe Ile Asn Lys Ser Asn Gly Glu
        355                 360                 365

Ser Val Tyr Val Glu Thr Glu Lys Glu Ile Phe Ser Lys Tyr Ser Glu
370                 375                 380

His Ile Thr Lys Glu Ile Ser Thr Ile Lys Asn Ser Ile Ile Thr Asp
385                 390                 395                 400

Val Asn Gly Asn Leu Leu Asp Asn Ile Gln Leu Asp His Thr Ser Gln
                405                 410                 415

Val Asn Thr Leu Asn Ala Ala Phe Phe Ile Gln Ser Leu Ile Asp Tyr
            420                 425                 430

Ser Ser Asn Lys Asp Val Leu Asn Asp Leu Ser Thr Ser Val Lys Val
        435                 440                 445

Gln Leu Tyr Ala Gln Leu Phe Ser Thr Gly Leu Asn Thr Ile Tyr Asp
450                 455                 460

Ser Ile Gln Leu Val Asn Leu Ile Ser Asn Ala Val Asn Asp Thr Ile
```

```
            465                 470                 475                 480
Asn Val Leu Pro Thr Ile Thr Glu Gly Ile Pro Ile Val Ser Thr Ile
                485                 490                 495

Leu Asp Gly Ile Asn Leu Gly Ala Ala Ile Lys Glu Leu Leu Asp Glu
                500                 505                 510

His Asp Pro Leu Leu Lys Lys Glu Leu Glu Ala Lys Val Gly Val Leu
                515                 520                 525

Ala Ile Asn Met Ser Leu Ser Ile Ala Ala Thr Val Ala Ser Ile Val
530                 535                 540

Gly Ile Gly Ala Glu Val Thr Ile Phe Leu Leu Pro Ile Ala Gly Ile
545                 550                 555                 560

Ser Ala Gly Ile Pro Ser Leu Val Asn Asn Glu Leu Ile Leu His Asp
                565                 570                 575

Lys Ala Thr Ser Val Val Asn Tyr Phe Asn His Leu Ser Glu Ser Lys
                580                 585                 590

Glu Tyr Gly Pro Leu Lys Thr Glu Asp Asp Lys Ile Leu Val Pro Ile
                595                 600                 605

Asp Asp Leu Val Ile Ser Glu Ile Asp Phe Asn Asn Asn Ser Ile Lys
                610                 615                 620

Leu Gly Thr Cys Asn Ile Leu Ala Met Glu Gly Gly Ser Gly His Thr
625                 630                 635                 640

Val Thr Gly Asn Ile Asp His Phe Phe Ser Ser Pro Tyr Ile Ser Ser
                645                 650                 655

His Ile Pro Ser Leu Ser Val Tyr Ser Ala Ile Gly Ile Lys Thr Glu
                660                 665                 670

Asn Leu Asp Phe Ser Lys Lys Ile Met Met Leu Pro Asn Ala Pro Ser
                675                 680                 685

Arg Val Phe Trp Trp Glu Thr Gly Ala Val Pro Gly Leu Arg Ser Leu
                690                 695                 700

Glu Asn Asn Gly Thr Lys Leu Leu Asp Ser Ile Arg Asp Leu Tyr Pro
705                 710                 715                 720

Gly Lys Phe Tyr Trp Arg Phe Tyr Ala Phe Phe Asp Tyr Ala Ile Thr
                725                 730                 735

Thr Leu Lys Pro Val Tyr Glu Asp Thr Asn Thr Lys Ile Lys Leu Asp
                740                 745                 750

Lys Asp Thr Arg Asn Phe Ile Met Pro Thr Ile Thr Thr Asp Glu Ile
                755                 760                 765

Arg Asn Lys Leu Ser Tyr Ser Phe Asp Gly Ala Gly Gly Thr Tyr Ser
770                 775                 780

Leu Leu Leu Ser Ser Tyr Pro Ile Ser Met Asn Ile Asn Leu Ser Lys
785                 790                 795                 800

Asp Asp Leu Trp Ile Phe Asn Ile Asp Asn Glu Val Arg Glu Ile Ser
                805                 810                 815

Ile Glu Asn Gly Thr Ile Lys Lys Gly Asn Leu Ile Glu Asp Val Leu
                820                 825                 830

Ser Lys Ile Asp Ile Asn Lys Asn Lys Leu Ile Ile Gly Asn Gln Thr
                835                 840                 845

Ile Asp Phe Ser Gly Asp Ile Asp Asn Lys Asp Arg Tyr Ile Phe Leu
                850                 855                 860

Thr Cys Glu Leu Asp Asp Lys Ile Ser Leu Ile Ile Glu Ile Asn Leu
865                 870                 875                 880

Val Ala Lys Ser Tyr Ser Leu Leu Leu Ser Gly Asp Lys Asn Tyr Leu
                885                 890                 895
```

-continued

```
Ile Ser Asn Leu Ser Asn Thr Ile Glu Lys Ile Asn Thr Leu Gly Leu
                900                 905                 910

Asp Ser Lys Asn Ile Ala Tyr Asn Tyr Thr Asp Glu Ser Asn Asn Lys
                915                 920                 925

Tyr Phe Gly Ala Ile Ser Lys Thr Ser Gln Lys Ser Ile Ile His Tyr
                930                 935                 940

Lys Lys Asp Ser Lys Asn Ile Leu Glu Phe Tyr Asn Gly Ser Thr Leu
945                 950                 955                 960

Glu Phe Asn Ser Lys Asp Phe Ile Ala Glu Asp Ile Asn Val Phe Met
                965                 970                 975

Lys Asp Asp Ile Asn Thr Ile Thr Gly Lys Tyr Tyr Val Asp Asn Asn
                980                 985                 990

Thr Asp Lys Ser Ile Asp Phe Ser Ile Ser Leu Val Ser Lys Asn Gln
                995                 1000                1005

Val Lys Val Asn Gly Leu Tyr Leu Asn Glu Ser Val Tyr Ser Ser
            1010                1015            1020

Tyr Leu Asp Phe Val Lys Asn Ser Asp Gly His His Asn Thr Ser
            1025                1030            1035

Asn Phe Met Asn Leu Phe Leu Asn Asn Ile Ser Phe Trp Lys Leu
            1040                1045            1050

Phe Gly Phe Glu Asn Ile Asn Phe Val Ile Asp Lys Tyr Phe Thr
            1055                1060            1065

Leu Val Gly Lys Thr Asn Leu Gly Tyr Val Glu Phe Ile Cys Asp
            1070                1075            1080

Asn Asn Lys Asn Ile Asp Ile Tyr Phe Gly Glu Trp Lys Thr Ser
            1085                1090            1095

Ser Ser Lys Ser Thr Ile Phe Ser Gly Asn Gly Arg Asn Val Val
            1100                1105            1110

Val Glu Pro Ile Tyr Asn Pro Asp Thr Gly Glu Asp Ile Ser Thr
            1115                1120            1125

Ser Leu Asp Phe Ser Tyr Glu Pro Leu Tyr Gly Ile Asp Arg Tyr
            1130                1135            1140

Ile Asn Lys Val Leu Ile Ala Pro Asp Leu Tyr Thr Ser Leu Ile
            1145                1150            1155

Asn Ile Asn Thr Asn Tyr Tyr Ser Asn Glu Tyr Tyr Pro Glu Ile
            1160                1165            1170

Ile Val Leu Asn Pro Asn Thr Phe His Lys Val Asn Ile Asn
            1175                1180            1185

Leu Asp Ser Ser Ser Phe Glu Tyr Lys Trp Ser Thr Glu Gly Ser
            1190                1195            1200

Asp Phe Ile Leu Val Arg Tyr Leu Glu Glu Ser Asn Lys Lys Ile
            1205                1210            1215

Leu Gln Lys Ile Arg Ile Lys Gly Ile Leu Ser Asn Thr Gln Ser
            1220                1225            1230

Phe Asn Lys Met Ser Ile Asp Phe Lys Asp Ile Lys Lys Leu Ser
            1235                1240            1245

Leu Gly Tyr Ile Met Ser Asn Phe Lys Ser Phe Asn Ser Glu Asn
            1250                1255            1260

Glu Leu Asp Arg Asp His Leu Gly Phe Lys Ile Ile Asp Asn Lys
            1265                1270            1275

Thr Tyr Tyr Tyr Asp Glu Asp Ser Lys Leu Val Lys Gly Leu Ile
            1280                1285            1290
```

Asn Ile Asn Asn Ser Leu Phe Tyr Phe Asp Pro Ile Glu Ser Asn
1295                1300                    1305

Leu

<210> SEQ ID NO 7
<211> LENGTH: 1309
<212> TYPE: PRT
<213> ORGANISM: Artificial Sequence
<220> FEATURE:
<223> OTHER INFORMATION: C. difficile Toxin A 542-1850 (toxinotype 0)
      Cysteine protease negative

<400> SEQUENCE: 7

Leu Ser Glu Asp Asn Gly Val Asp Phe Asn Lys Asn Thr Ala Leu Asp
1               5                   10                  15

Lys Asn Tyr Leu Leu Asn Asn Lys Ile Pro Ser Asn Asn Val Glu Glu
            20                  25                  30

Ala Gly Ser Lys Asn Tyr Val His Tyr Ile Ile Gln Leu Gln Gly Asp
        35                  40                  45

Asp Ile Ser Tyr Glu Ala Thr Cys Asn Leu Phe Ser Lys Asn Pro Lys
    50                  55                  60

Asn Ser Ile Ile Ile Gln Arg Asn Met Asn Glu Ser Ala Lys Ser Tyr
65                  70                  75                  80

Phe Leu Ser Asp Asp Gly Glu Ser Ile Leu Glu Leu Asn Lys Tyr Arg
                85                  90                  95

Ile Pro Glu Arg Leu Lys Asn Lys Glu Lys Val Lys Val Thr Phe Ile
            100                 105                 110

Gly His Gly Lys Asp Glu Phe Asn Thr Ser Glu Phe Ala Arg Leu Ser
        115                 120                 125

Val Asp Ser Leu Ser Asn Glu Ile Ser Ser Phe Leu Asp Thr Ile Lys
    130                 135                 140

Leu Asp Ile Ser Pro Lys Asn Val Glu Val Asn Leu Leu Gly Ala Asn
145                 150                 155                 160

Met Phe Ser Tyr Asp Phe Asn Val Glu Glu Thr Tyr Pro Gly Lys Leu
                165                 170                 175

Leu Leu Ser Ile Met Asp Lys Ile Thr Ser Thr Leu Pro Asp Val Asn
            180                 185                 190

Lys Asn Ser Ile Thr Ile Gly Ala Asn Gln Tyr Glu Val Arg Ile Asn
        195                 200                 205

Ser Glu Gly Arg Lys Glu Leu Leu Ala His Ser Gly Lys Trp Ile Asn
    210                 215                 220

Lys Glu Glu Ala Ile Met Ser Asp Leu Ser Ser Lys Glu Tyr Ile Phe
225                 230                 235                 240

Phe Asp Ser Ile Asp Asn Lys Leu Lys Ala Lys Ser Lys Asn Ile Pro
                245                 250                 255

Gly Leu Ala Ser Ile Ser Glu Asp Ile Lys Thr Leu Leu Leu Asp Ala
            260                 265                 270

Ser Val Ser Pro Asp Thr Lys Phe Ile Leu Asn Asn Leu Lys Leu Asn
        275                 280                 285

Ile Glu Ser Ser Ile Gly Asp Tyr Ile Tyr Tyr Glu Lys Leu Glu Pro
    290                 295                 300

Val Lys Asn Ile Ile His Asn Ser Ile Asp Asp Leu Ile Asp Glu Phe
305                 310                 315                 320

Asn Leu Leu Glu Asn Val Ser Asp Glu Leu Tyr Glu Leu Lys Lys Leu
                325                 330                 335

-continued

Asn Asn Leu Asp Glu Lys Tyr Leu Ile Ser Phe Glu Asp Ile Ser Lys
            340                 345                 350

Asn Asn Ser Thr Tyr Ser Val Arg Phe Ile Asn Lys Ser Asn Gly Glu
            355                 360                 365

Ser Val Tyr Val Glu Thr Glu Lys Glu Ile Phe Ser Lys Tyr Ser Glu
    370                 375                 380

His Ile Thr Lys Glu Ile Ser Thr Ile Lys Asn Ser Ile Ile Thr Asp
385                 390                 395                 400

Val Asn Gly Asn Leu Leu Asp Asn Ile Gln Leu Asp His Thr Ser Gln
                405                 410                 415

Val Asn Thr Leu Asn Ala Ala Phe Phe Ile Gln Ser Leu Ile Asp Tyr
            420                 425                 430

Ser Ser Asn Lys Asp Val Leu Asn Asp Leu Ser Thr Ser Val Lys Val
            435                 440                 445

Gln Leu Tyr Ala Gln Leu Phe Ser Thr Gly Leu Asn Thr Ile Tyr Asp
            450                 455                 460

Ser Ile Gln Leu Val Asn Leu Ile Ser Asn Ala Val Asn Asp Thr Ile
465                 470                 475                 480

Asn Val Leu Pro Thr Ile Thr Glu Gly Ile Pro Ile Val Ser Thr Ile
                485                 490                 495

Leu Asp Gly Ile Asn Leu Gly Ala Ala Ile Lys Glu Leu Leu Asp Glu
            500                 505                 510

His Asp Pro Leu Leu Lys Lys Glu Leu Glu Ala Lys Val Gly Val Leu
            515                 520                 525

Ala Ile Asn Met Ser Leu Ser Ile Ala Ala Thr Val Ala Ser Ile Val
530                 535                 540

Gly Ile Gly Ala Glu Val Thr Ile Phe Leu Leu Pro Ile Ala Gly Ile
545                 550                 555                 560

Ser Ala Gly Ile Pro Ser Leu Val Asn Asn Glu Leu Ile Leu His Asp
                565                 570                 575

Lys Ala Thr Ser Val Val Asn Tyr Phe Asn His Leu Ser Glu Ser Lys
            580                 585                 590

Lys Tyr Gly Pro Leu Lys Thr Glu Asp Asp Lys Ile Leu Val Pro Ile
            595                 600                 605

Asp Asp Leu Val Ile Ser Glu Ile Asp Phe Asn Asn Asn Ser Ile Lys
    610                 615                 620

Leu Gly Thr Cys Asn Ile Leu Ala Met Glu Gly Gly Ser Gly His Thr
625                 630                 635                 640

Val Thr Gly Asn Ile Asp His Phe Phe Ser Ser Pro Ser Ile Ser Ser
                645                 650                 655

His Ile Pro Ser Leu Ser Ile Tyr Ser Ala Ile Gly Ile Glu Thr Glu
            660                 665                 670

Asn Leu Asp Phe Ser Lys Lys Ile Met Met Leu Pro Asn Ala Pro Ser
            675                 680                 685

Arg Val Phe Trp Trp Glu Thr Gly Ala Val Pro Gly Leu Arg Ser Leu
    690                 695                 700

Glu Asn Asp Gly Thr Arg Leu Leu Asp Ser Ile Arg Asp Leu Tyr Pro
705                 710                 715                 720

Gly Lys Phe Tyr Trp Arg Phe Tyr Ala Phe Phe Asp Tyr Ala Ile Thr
                725                 730                 735

Thr Leu Lys Pro Val Tyr Glu Asp Thr Asn Ile Lys Ile Lys Leu Asp
            740                 745                 750

Lys Asp Thr Arg Asn Phe Ile Met Pro Thr Ile Thr Thr Asn Glu Ile

```
              755                 760                 765
Arg Asn Lys Leu Ser Tyr Ser Phe Asp Gly Ala Gly Gly Thr Tyr Ser
770                 775                 780

Leu Leu Leu Ser Ser Tyr Pro Ile Ser Thr Asn Ile Asn Leu Ser Lys
785                 790                 795                 800

Asp Asp Leu Trp Ile Phe Asn Ile Asp Asn Glu Val Arg Glu Ile Ser
                    805                 810                 815

Ile Glu Asn Gly Thr Ile Lys Lys Gly Lys Leu Ile Lys Asp Val Leu
            820                 825                 830

Ser Lys Ile Asp Ile Asn Lys Asn Lys Leu Ile Ile Gly Asn Gln Thr
                835                 840                 845

Ile Asp Phe Ser Gly Asp Ile Asp Asn Lys Asp Arg Tyr Ile Phe Leu
    850                 855                 860

Thr Cys Glu Leu Asp Asp Lys Ile Ser Leu Ile Ile Glu Ile Asn Leu
865                 870                 875                 880

Val Ala Lys Ser Tyr Ser Leu Leu Leu Ser Gly Asp Lys Asn Tyr Leu
                885                 890                 895

Ile Ser Asn Leu Ser Asn Thr Ile Glu Lys Ile Asn Thr Leu Gly Leu
                900                 905                 910

Asp Ser Lys Asn Ile Ala Tyr Asn Tyr Thr Asp Glu Ser Asn Asn Lys
                915                 920                 925

Tyr Phe Gly Ala Ile Ser Lys Thr Ser Gln Lys Ser Ile Ile His Tyr
    930                 935                 940

Lys Lys Asp Ser Lys Asn Ile Leu Glu Phe Tyr Asn Asp Ser Thr Leu
945                 950                 955                 960

Glu Phe Asn Ser Lys Asp Phe Ile Ala Glu Asp Ile Asn Val Phe Met
                965                 970                 975

Lys Asp Asp Ile Asn Thr Ile Thr Gly Lys Tyr Tyr Val Asp Asn Asn
                980                 985                 990

Thr Asp Lys Ser Ile Asp Phe Ser  Ile Ser Leu Val Ser  Lys Asn Gln
                995                 1000                1005

Val Lys Val Asn Gly Leu Tyr  Leu Asn Glu Ser Val  Tyr Ser Ser
    1010                1015                1020

Tyr Leu Asp Phe Val Lys Asn  Ser Asp Gly His His  Asn Thr Ser
    1025                1030                1035

Asn Phe Met Asn Leu Phe Leu  Asp Asn Ile Ser Phe  Trp Lys Leu
    1040                1045                1050

Phe Gly Phe Glu Asn Ile Asn  Phe Val Ile Asp Lys  Tyr Phe Thr
    1055                1060                1065

Leu Val Gly Lys Thr Asn Leu  Gly Tyr Val Glu Phe  Ile Cys Asp
    1070                1075                1080

Asn Asn Lys Asn Ile Asp Ile  Tyr Phe Gly Glu Trp  Lys Thr Ser
    1085                1090                1095

Ser Ser Lys Ser Thr Ile Phe  Ser Gly Asn Gly Arg  Asn Val Val
    1100                1105                1110

Val Glu Pro Ile Tyr Asn Pro  Asp Thr Gly Glu Asp  Ile Ser Thr
    1115                1120                1125

Ser Leu Asp Phe Ser Tyr Glu  Pro Leu Tyr Gly Ile  Asp Arg Tyr
    1130                1135                1140

Ile Asn Lys Val Leu Ile Ala  Pro Asp Leu Tyr Thr  Ser Leu Ile
    1145                1150                1155

Asn Ile Asn Thr Asn Tyr Tyr  Ser Asn Glu Tyr Tyr  Pro Glu Ile
    1160                1165                1170
```

```
Ile Val Leu Asn Pro Asn Thr Phe His Lys Lys Val Asn Ile Asn
    1175                1180                1185

Leu Asp Ser Ser Ser Phe Glu Tyr Lys Trp Ser Thr Glu Gly Ser
    1190                1195                1200

Asp Phe Ile Leu Val Arg Tyr Leu Glu Glu Ser Asn Lys Lys Ile
    1205                1210                1215

Leu Gln Lys Ile Arg Ile Lys Gly Ile Leu Ser Asn Thr Gln Ser
    1220                1225                1230

Phe Asn Lys Met Ser Ile Asp Phe Lys Asp Ile Lys Lys Leu Ser
    1235                1240                1245

Leu Gly Tyr Ile Met Ser Asn Phe Lys Ser Phe Asn Ser Glu Asn
    1250                1255                1260

Glu Leu Asp Arg Asp His Leu Gly Phe Lys Ile Ile Asp Asn Lys
    1265                1270                1275

Thr Tyr Tyr Tyr Asp Glu Asp Ser Lys Leu Val Lys Gly Leu Ile
    1280                1285                1290

Asn Ile Asn Asn Ser Leu Phe Tyr Phe Asp Pro Ile Glu Phe Asn
    1295                1300                1305

Leu

<210> SEQ ID NO 8
<211> LENGTH: 1080
<212> TYPE: PRT
<213> ORGANISM: Artificial Sequence
<220> FEATURE:
<223> OTHER INFORMATION: C. difficile Toxin A 770-1850

<400> SEQUENCE: 8

Met Ser Asp Leu Ser Ser Lys Glu Tyr Ile Phe Phe Asp Ser Ile Asp
1               5                   10                  15

Asn Lys Leu Lys Ala Lys Ser Lys Asn Ile Pro Gly Le

Val Leu Asn Asp Leu Ser Thr Ser Val Lys Val Gln Leu Tyr Ala Gln
210                 215                 220

Leu Phe Ser Thr Gly Leu Asn Thr Ile Tyr Asp Ser Ile Gln Leu Val
225                 230                 235                 240

Asn Leu Ile Ser Asn Ala Val Asn Asp Thr Ile Asn Val Leu Pro Thr
                245                 250                 255

Ile Thr Glu Gly Ile Pro Ile Val Ser Thr Ile Leu Asp Gly Ile Asn
            260                 265                 270

Leu Gly Ala Ala Ile Lys Glu Leu Leu Asp Glu His Asp Pro Leu Leu
                275                 280                 285

Lys Lys Glu Leu Glu Ala Lys Val Gly Val Leu Ala Ile Asn Met Ser
290                 295                 300

Leu Ser Ile Ala Ala Thr Val Ala Ser Ile Val Gly Ile Gly Ala Glu
305                 310                 315                 320

Val Thr Ile Phe Leu Leu Pro Ile Ala Gly Ile Ser Ala Gly Ile Pro
                325                 330                 335

Ser Leu Val Asn Asn Glu Leu Ile Leu His Asp Lys Ala Thr Ser Val
                340                 345                 350

Val Asn Tyr Phe Asn His Leu Ser Glu Ser Lys Lys Tyr Gly Pro Leu
            355                 360                 365

Lys Thr Glu Asp Asp Lys Ile Leu Val Pro Ile Asp Asp Leu Val Ile
370                 375                 380

Ser Glu Ile Asp Phe Asn Asn Asn Ser Ile Lys Leu Gly Thr Cys Asn
385                 390                 395                 400

Ile Leu Ala Met Glu Gly Gly Ser Gly His Thr Val Thr Gly Asn Ile
                405                 410                 415

Asp His Phe Phe Ser Ser Pro Ser Ile Ser Ser His Ile Pro Ser Leu
                420                 425                 430

Ser Ile Tyr Ser Ala Ile Gly Ile Glu Thr Glu Asn Leu Asp Phe Ser
            435                 440                 445

Lys Lys Ile Met Met Leu Pro Asn Ala Pro Ser Arg Val Phe Trp Trp
450                 455                 460

Glu Thr Gly Ala Val Pro Gly Leu Arg Ser Leu Glu Asn Asp Gly Thr
465                 470                 475                 480

Arg Leu Leu Asp Ser Ile Arg Asp Leu Tyr Pro Gly Lys Phe Tyr Trp
                485                 490                 495

Arg Phe Tyr Ala Phe Phe Asp Tyr Ala Ile Thr Thr Leu Lys Pro Val
                500                 505                 510

Tyr Glu Asp Thr Asn Ile Lys Ile Lys Leu Asp Lys Asp Thr Arg Asn
            515                 520                 525

Phe Ile Met Pro Thr Ile Thr Thr Asn Glu Ile Arg Asn Lys Leu Ser
530                 535                 540

Tyr Ser Phe Asp Gly Ala Gly Gly Thr Tyr Ser Leu Leu Leu Ser Ser
545                 550                 555                 560

Tyr Pro Ile Ser Thr Asn Ile Asn Leu Ser Lys Asp Asp Leu Trp Ile
                565                 570                 575

Phe Asn Ile Asp Asn Glu Val Arg Glu Ile Ser Ile Glu Asn Gly Thr
                580                 585                 590

Ile Lys Lys Gly Lys Leu Ile Lys Asp Val Leu Ser Lys Ile Asp Ile
            595                 600                 605

Asn Lys Asn Lys Leu Ile Ile Gly Asn Gln Thr Ile Asp Phe Ser Gly
610                 615                 620

Asp Ile Asp Asn Lys Asp Arg Tyr Ile Phe Leu Thr Cys Glu Leu Asp

-continued

```
            625                 630                 635                 640
Asp Lys Ile Ser Leu Ile Ile Glu Ile Asn Leu Val Ala Lys Ser Tyr
                    645                 650                 655

Ser Leu Leu Leu Ser Gly Asp Lys Asn Tyr Leu Ile Ser Asn Leu Ser
            660                 665                 670

Asn Thr Ile Glu Lys Ile Asn Thr Leu Gly Leu Asp Ser Lys Asn Ile
            675                 680                 685

Ala Tyr Asn Tyr Thr Asp Glu Ser Asn Lys Tyr Phe Gly Ala Ile
            690                 695                 700

Ser Lys Thr Ser Gln Lys Ser Ile Ile His Tyr Lys Lys Asp Ser Lys
705                 710                 715                 720

Asn Ile Leu Glu Phe Tyr Asn Asp Ser Thr Leu Glu Phe Asn Ser Lys
                    725                 730                 735

Asp Phe Ile Ala Glu Asp Ile Asn Val Phe Met Lys Asp Ile Asn
                    740                 745                 750

Thr Ile Thr Gly Lys Tyr Tyr Val Asp Asn Asn Thr Asp Lys Ser Ile
            755                 760                 765

Asp Phe Ser Ile Ser Leu Val Ser Lys Asn Gln Val Lys Val Asn Gly
            770                 775                 780

Leu Tyr Leu Asn Glu Ser Val Tyr Ser Ser Tyr Leu Asp Phe Val Lys
785                 790                 795                 800

Asn Ser Asp Gly His His Asn Thr Ser Asn Phe Met Asn Leu Phe Leu
                    805                 810                 815

Asp Asn Ile Ser Phe Trp Lys Leu Phe Gly Phe Glu Asn Ile Asn Phe
                    820                 825                 830

Val Ile Asp Lys Tyr Phe Thr Leu Val Gly Lys Thr Asn Leu Gly Tyr
            835                 840                 845

Val Glu Phe Ile Cys Asp Asn Asn Lys Asn Ile Asp Ile Tyr Phe Gly
            850                 855                 860

Glu Trp Lys Thr Ser Ser Ser Lys Ser Thr Ile Phe Ser Gly Asn Gly
865                 870                 875                 880

Arg Asn Val Val Val Glu Pro Ile Tyr Asn Pro Asp Thr Gly Glu Asp
                    885                 890                 895

Ile Ser Thr Ser Leu Asp Phe Ser Tyr Glu Pro Leu Tyr Gly Ile Asp
                    900                 905                 910

Arg Tyr Ile Asn Lys Val Leu Ile Ala Pro Asp Leu Tyr Thr Ser Leu
            915                 920                 925

Ile Asn Ile Asn Thr Asn Tyr Tyr Ser Asn Glu Tyr Tyr Pro Glu Ile
            930                 935                 940

Ile Val Leu Asn Pro Asn Thr Phe His Lys Lys Val Asn Ile Asn Leu
945                 950                 955                 960

Asp Ser Ser Ser Phe Glu Tyr Lys Trp Ser Thr Glu Gly Ser Asp Phe
                    965                 970                 975

Ile Leu Val Arg Tyr Leu Glu Glu Ser Asn Lys Lys Ile Leu Gln Lys
            980                 985                 990

Ile Arg Ile Lys Gly Ile Leu Ser  Asn Thr Gln Ser Phe  Asn Lys Met
            995                 1000                1005

Ser Ile  Asp Phe Lys Asp Ile  Lys Lys Leu Ser Leu  Gly Tyr Ile
    1010                1015                1020

Met Ser  Asn Phe Lys Ser Phe  Asn Ser Glu Asn Glu  Leu Asp Arg
    1025                1030                1035

Asp His  Leu Gly Phe Lys Ile  Ile Asp Asn Lys Thr  Tyr Tyr Tyr
    1040                1045                1050
```

```
Asp Glu Asp Ser Lys Leu Val Lys Gly Leu Ile Asn Ile Asn Asn
    1055                1060                1065

Ser Leu Phe Tyr Phe Asp Pro Ile Glu Phe Asn Leu
    1070                1075                1080

<210> SEQ ID NO 9
<211> LENGTH: 721
<212> TYPE: PRT
<213> ORGANISM: Artificial Sequence
<220> FEATURE:
<223> OTHER INFORMATION: C. difficile Toxin A 1130-1850

<400> SEQUENCE: 9

Ser Glu Ser Lys Lys Tyr Gly Pro Leu Lys Thr Glu Asp Asp Lys Ile
1               5                   10                  15

Leu Val Pro Ile Asp Asp Leu Val Ile Ser Glu Ile Asp Phe Asn Asn
            20                  25                  30

Asn Ser Ile Lys Leu Gly Thr Cys Asn Ile Leu Ala Met Glu Gly Gly
        35                  40                  45

Ser Gly His Thr Val Thr Gly Asn Ile Asp His Phe Phe Ser Ser Pro
    50                  55                  60

Ser Ile Ser Ser His Ile Pro Ser Leu Ser Ile Tyr Ser Ala Ile Gly
65                  70                  75                  80

Ile Glu Thr Glu Asn Leu Asp Phe Ser Lys Lys Ile Met Met Leu Pro
                85                  90                  95

Asn Ala Pro Ser Arg Val Phe Trp Trp Glu Thr Gly Ala Val Pro Gly
            100                 105                 110

Leu Arg Ser Leu Glu Asn Asp Gly Thr Arg Leu Leu Asp Ser Ile Arg
        115                 120                 125

Asp Leu Tyr Pro Gly Lys Phe Tyr Trp Arg Phe Tyr Ala Phe Phe Asp
    130                 135                 140

Tyr Ala Ile Thr Thr Leu Lys Pro Val Tyr Glu Asp Thr Asn Ile Lys
145                 150                 155                 160

Ile Lys Leu Asp Lys Asp Thr Arg Asn Phe Ile Met Pro Thr Ile Thr
                165                 170                 175

Thr Asn Glu Ile Arg Asn Lys Leu Ser Tyr Ser Phe Asp Gly Ala Gly
            180                 185                 190

Gly Thr Tyr Ser Leu Leu Leu Ser Ser Tyr Pro Ile Ser Thr Asn Ile
        195                 200                 205

Asn Leu Ser Lys Asp Asp Leu Trp Ile Phe Asn Ile Asp Asn Glu Val
    210                 215                 220

Arg Glu Ile Ser Ile Glu Asn Gly Thr Ile Lys Lys Gly Lys Leu Ile
225                 230                 235                 240

Lys Asp Val Leu Ser Lys Ile Asp Ile Asn Lys Asn Lys Leu Ile Ile
                245                 250                 255

Gly Asn Gln Thr Ile Asp Phe Ser Gly Asp Ile Asp Asn Lys Asp Arg
            260                 265                 270

Tyr Ile Phe Leu Thr Cys Glu Leu Asp Asp Lys Ile Ser Leu Ile Ile
        275                 280                 285

Glu Ile Asn Leu Val Ala Lys Ser Tyr Ser Leu Leu Leu Ser Gly Asp
    290                 295                 300

Lys Asn Tyr Leu Ile Ser Asn Leu Ser Asn Thr Ile Glu Lys Ile Asn
305                 310                 315                 320

Thr Leu Gly Leu Asp Ser Lys Asn Ile Ala Tyr Asn Tyr Thr Asp Glu
                325                 330                 335
```

Ser Asn Asn Lys Tyr Phe Gly Ala Ile Ser Lys Thr Ser Gln Lys Ser
            340                 345                 350

Ile Ile His Tyr Lys Lys Asp Ser Lys Asn Ile Leu Glu Phe Tyr Asn
        355                 360                 365

Asp Ser Thr Leu Glu Phe Asn Ser Lys Asp Phe Ile Ala Glu Asp Ile
    370                 375                 380

Asn Val Phe Met Lys Asp Asp Ile Asn Thr Ile Thr Gly Lys Tyr Tyr
385                 390                 395                 400

Val Asp Asn Asn Thr Asp Lys Ser Ile Asp Phe Ser Ile Ser Leu Val
            405                 410                 415

Ser Lys Asn Gln Val Lys Val Asn Gly Leu Tyr Leu Asn Glu Ser Val
        420                 425                 430

Tyr Ser Ser Tyr Leu Asp Phe Val Lys Asn Ser Asp Gly His His Asn
    435                 440                 445

Thr Ser Asn Phe Met Asn Leu Phe Leu Asp Asn Ile Ser Phe Trp Lys
450                 455                 460

Leu Phe Gly Phe Glu Asn Ile Asn Phe Val Ile Asp Lys Tyr Phe Thr
465                 470                 475                 480

Leu Val Gly Lys Thr Asn Leu Gly Tyr Val Glu Phe Ile Cys Asp Asn
            485                 490                 495

Asn Lys Asn Ile Asp Ile Tyr Phe Gly Glu Trp Lys Thr Ser Ser Ser
        500                 505                 510

Lys Ser Thr Ile Phe Ser Gly Asn Gly Arg Asn Val Val Glu Pro
    515                 520                 525

Ile Tyr Asn Pro Asp Thr Gly Glu Asp Ile Ser Thr Ser Leu Asp Phe
530                 535                 540

Ser Tyr Glu Pro Leu Tyr Gly Ile Asp Arg Tyr Ile Asn Lys Val Leu
545                 550                 555                 560

Ile Ala Pro Asp Leu Tyr Thr Ser Leu Ile Asn Ile Asn Thr Asn Tyr
            565                 570                 575

Tyr Ser Asn Glu Tyr Tyr Pro Glu Ile Ile Val Leu Asn Pro Asn Thr
        580                 585                 590

Phe His Lys Lys Val Asn Ile Asn Leu Asp Ser Ser Phe Glu Tyr
    595                 600                 605

Lys Trp Ser Thr Glu Gly Ser Asp Phe Ile Leu Val Arg Tyr Leu Glu
610                 615                 620

Glu Ser Asn Lys Lys Ile Leu Gln Lys Ile Arg Ile Lys Gly Ile Leu
625                 630                 635                 640

Ser Asn Thr Gln Ser Phe Asn Lys Met Ser Ile Asp Phe Lys Asp Ile
            645                 650                 655

Lys Lys Leu Ser Leu Gly Tyr Ile Met Ser Asn Phe Lys Ser Phe Asn
        660                 665                 670

Ser Glu Asn Glu Leu Asp Arg Asp His Leu Gly Phe Lys Ile Ile Asp
    675                 680                 685

Asn Lys Thr Tyr Tyr Tyr Asp Glu Asp Ser Lys Leu Val Lys Gly Leu
690                 695                 700

Ile Asn Ile Asn Asn Ser Leu Phe Tyr Phe Asp Pro Ile Glu Phe Asn
705                 710                 715                 720

Leu

<210> SEQ ID NO 10
<211> LENGTH: 1310
<212> TYPE: PRT

<213> ORGANISM: Artificial Sequence
<220> FEATURE:
<223> OTHER INFORMATION: C. difficile Toxin B (toxinotype 0) 543-1852

<400> SEQUENCE: 10

| | | | | | | | | | | | | | | |
|---|---|---|---|---|---|---|---|---|---|---|---|---|---|---|
| Leu | Gly | Glu | Asp | Asp | Asn | Leu | Asp | Phe | Ser | Gln | Asn | Ile | Val | Val | Asp |
| 1 | | | | 5 | | | | | 10 | | | | | 15 | |
| Lys | Glu | Tyr | Leu | Leu | Glu | Lys | Ile | Ser | Ser | Leu | Ala | Arg | Ser | Ser | Glu |
| | | | 20 | | | | | 25 | | | | | 30 | | |
| Arg | Gly | Tyr | Ile | His | Tyr | Ile | Val | Gln | Leu | Gln | Gly | Asp | Lys | Ile | Ser |
| | | 35 | | | | | 40 | | | | | 45 | | | |
| Tyr | Glu | Ala | Ala | Cys | Asn | Leu | Phe | Ala | Lys | Thr | Pro | Tyr | Asp | Ser | Val |
| | 50 | | | | | 55 | | | | | 60 | | | | |
| Leu | Phe | Gln | Lys | Asn | Ile | Glu | Asp | Ser | Glu | Ile | Ala | Tyr | Tyr | Tyr | Asn |
| 65 | | | | | 70 | | | | | 75 | | | | | 80 |
| Pro | Gly | Asp | Gly | Glu | Ile | Gln | Glu | Ile | Asp | Lys | Tyr | Lys | Ile | Pro | Ser |
| | | | | 85 | | | | | 90 | | | | | 95 | |
| Ile | Ile | Ser | Asp | Arg | Pro | Lys | Ile | Lys | Leu | Thr | Phe | Ile | Gly | His | Gly |
| | | | 100 | | | | | 105 | | | | | 110 | | |
| Lys | Asp | Glu | Phe | Asn | Thr | Asp | Ile | Phe | Ala | Gly | Phe | Asp | Val | Asp | Ser |
| | | | 115 | | | | | 120 | | | | | 125 | | |
| Leu | Ser | Thr | Glu | Ile | Glu | Ala | Ala | Ile | Asp | Leu | Ala | Lys | Glu | Asp | Ile |
| | | 130 | | | | | 135 | | | | | 140 | | | |
| Ser | Pro | Lys | Ser | Ile | Glu | Ile | Asn | Leu | Leu | Gly | Cys | Asn | Met | Phe | Ser |
| 145 | | | | | 150 | | | | | 155 | | | | | 160 |
| Tyr | Ser | Ile | Asn | Val | Glu | Glu | Thr | Tyr | Pro | Gly | Lys | Leu | Leu | Leu | Lys |
| | | | | 165 | | | | | 170 | | | | | 175 | |
| Val | Lys | Asp | Lys | Ile | Ser | Glu | Leu | Met | Pro | Ser | Ile | Ser | Gln | Asp | Ser |
| | | | 180 | | | | | 185 | | | | | 190 | | |
| Ile | Ile | Val | Ser | Ala | Asn | Gln | Tyr | Glu | Val | Arg | Ile | Asn | Ser | Glu | Gly |
| | | 195 | | | | | 200 | | | | | 205 | | | |
| Arg | Arg | Glu | Leu | Leu | Asp | His | Ser | Gly | Glu | Trp | Ile | Asn | Lys | Glu | Glu |
| | 210 | | | | | 215 | | | | | 220 | | | | |
| Ser | Ile | Ile | Lys | Asp | Ile | Ser | Ser | Lys | Glu | Tyr | Ile | Ser | Phe | Asn | Pro |
| 225 | | | | | 230 | | | | | 235 | | | | | 240 |
| Lys | Glu | Asn | Lys | Ile | Thr | Val | Lys | Ser | Lys | Asn | Leu | Pro | Glu | Leu | Ser |
| | | | | 245 | | | | | 250 | | | | | 255 | |
| Thr | Leu | Leu | Gln | Glu | Ile | Arg | Asn | Asn | Ser | Asn | Ser | Ser | Asp | Ile | Glu |
| | | | 260 | | | | | 265 | | | | | 270 | | |
| Leu | Glu | Glu | Lys | Val | Met | Leu | Thr | Glu | Cys | Glu | Ile | Asn | Val | Ile | Ser |
| | | 275 | | | | | 280 | | | | | 285 | | | |
| Asn | Ile | Asp | Thr | Gln | Ile | Val | Glu | Glu | Arg | Ile | Glu | Glu | Ala | Lys | Asn |
| | 290 | | | | | 295 | | | | | 300 | | | | |
| Leu | Thr | Ser | Asp | Ser | Ile | Asn | Tyr | Ile | Lys | Asp | Glu | Phe | Lys | Leu | Ile |
| 305 | | | | | 310 | | | | | 315 | | | | | 320 |
| Glu | Ser | Ile | Ser | Asp | Ala | Leu | Cys | Asp | Leu | Lys | Gln | Gln | Asn | Glu | Leu |
| | | | | 325 | | | | | 330 | | | | | 335 | |
| Glu | Asp | Ser | His | Phe | Ile | Ser | Phe | Glu | Asp | Ile | Ser | Glu | Thr | Asp | Glu |
| | | | 340 | | | | | 345 | | | | | 350 | | |
| Gly | Phe | Ser | Ile | Arg | Phe | Ile | Asn | Lys | Glu | Thr | Gly | Glu | Ser | Ile | Phe |
| | | 355 | | | | | 360 | | | | | 365 | | | |
| Val | Glu | Thr | Glu | Lys | Thr | Ile | Phe | Ser | Glu | Tyr | Ala | Asn | His | Ile | Thr |
| | 370 | | | | | 375 | | | | | 380 | | | | |
| Glu | Glu | Ile | Ser | Lys | Ile | Lys | Gly | Thr | Ile | Phe | Asp | Thr | Val | Asn | Gly |

-continued

```
            385                 390                 395                 400
Lys Leu Val Lys Lys Val Asn Leu Asp Thr Thr His Glu Val Asn Thr
                    405                 410                 415

Leu Asn Ala Ala Phe Phe Ile Gln Ser Leu Ile Glu Tyr Asn Ser Ser
                    420                 425                 430

Lys Glu Ser Leu Ser Asn Leu Ser Val Ala Met Lys Val Gln Val Tyr
                    435                 440                 445

Ala Gln Leu Phe Ser Thr Gly Leu Asn Thr Ile Thr Asp Ala Ala Lys
                    450                 455                 460

Val Val Glu Leu Val Ser Thr Ala Leu Asp Glu Thr Ile Asp Leu Leu
465                 470                 475                 480

Pro Thr Leu Ser Glu Gly Leu Pro Ile Ile Ala Thr Ile Ile Asp Gly
                    485                 490                 495

Val Ser Leu Gly Ala Ala Ile Lys Glu Leu Ser Glu Thr Ser Asp Pro
                    500                 505                 510

Leu Leu Arg Gln Glu Ile Glu Ala Lys Ile Gly Ile Met Ala Val Asn
                    515                 520                 525

Leu Thr Thr Ala Thr Thr Ala Ile Ile Thr Ser Ser Leu Gly Ile Ala
                    530                 535                 540

Ser Gly Phe Ser Ile Leu Leu Val Pro Leu Ala Gly Ile Ser Ala Gly
545                 550                 555                 560

Ile Pro Ser Leu Val Asn Asn Glu Leu Val Leu Arg Asp Lys Ala Thr
                    565                 570                 575

Lys Val Val Asp Tyr Phe Lys His Val Ser Leu Val Glu Thr Glu Gly
                    580                 585                 590

Val Phe Thr Leu Leu Asp Asp Lys Ile Met Met Pro Gln Asp Asp Leu
                    595                 600                 605

Val Ile Ser Glu Ile Asp Phe Asn Asn Asn Ser Ile Val Leu Gly Lys
                    610                 615                 620

Cys Glu Ile Trp Arg Met Glu Gly Gly Ser Gly His Thr Val Thr Asp
625                 630                 635                 640

Asp Ile Asp His Phe Phe Ser Ala Pro Ser Ile Thr Tyr Arg Glu Pro
                    645                 650                 655

His Leu Ser Ile Tyr Asp Val Leu Glu Val Gln Lys Glu Glu Leu Asp
                    660                 665                 670

Leu Ser Lys Asp Leu Met Val Leu Pro Asn Ala Pro Asn Arg Val Phe
                    675                 680                 685

Ala Trp Glu Thr Gly Trp Thr Pro Gly Leu Arg Ser Leu Glu Asn Asp
                    690                 695                 700

Gly Thr Lys Leu Leu Asp Arg Ile Arg Asp Asn Tyr Glu Gly Glu Phe
705                 710                 715                 720

Tyr Trp Arg Tyr Phe Ala Phe Ile Ala Asp Ala Leu Ile Thr Thr Leu
                    725                 730                 735

Lys Pro Arg Tyr Glu Asp Thr Asn Ile Arg Ile Asn Leu Asp Ser Asn
                    740                 745                 750

Thr Arg Ser Phe Ile Val Pro Ile Ile Thr Thr Glu Tyr Ile Arg Glu
                    755                 760                 765

Lys Leu Ser Tyr Ser Phe Tyr Gly Ser Gly Gly Thr Tyr Ala Leu Ser
                    770                 775                 780

Leu Ser Gln Tyr Asn Met Gly Ile Asn Ile Glu Leu Ser Glu Ser Asp
785                 790                 795                 800

Val Trp Ile Ile Asp Val Asp Asn Val Val Arg Asp Val Thr Ile Glu
                    805                 810                 815
```

-continued

Ser Asp Lys Ile Lys Lys Gly Asp Leu Ile Glu Gly Ile Leu Ser Thr
                820             825             830

Leu Ser Ile Glu Glu Asn Lys Ile Ile Leu Asn Ser His Glu Ile Asn
            835             840             845

Phe Ser Gly Glu Val Asn Gly Ser Asn Gly Phe Val Ser Leu Thr Phe
        850             855             860

Ser Ile Leu Glu Gly Ile Asn Ala Ile Ile Glu Val Asp Leu Ser
865         870             875             880

Lys Ser Tyr Lys Leu Leu Ile Ser Gly Glu Leu Lys Ile Leu Met Leu
                885             890             895

Asn Ser Asn His Ile Gln Gln Lys Ile Asp Tyr Ile Gly Phe Asn Ser
            900             905             910

Glu Leu Gln Lys Asn Ile Pro Tyr Ser Phe Val Asp Ser Gly Gly Lys
        915             920             925

Glu Asn Gly Phe Ile Asn Gly Ser Thr Lys Glu Gly Leu Phe Val Ser
    930             935             940

Glu Leu Pro Asp Val Val Leu Ile Ser Lys Val Tyr Met Asp Asp Ser
945             950             955             960

Lys Pro Ser Phe Gly Tyr Tyr Ser Asn Asn Leu Lys Asp Val Lys Val
                965             970             975

Ile Thr Lys Asp Asn Val Asn Ile Leu Thr Gly Tyr Tyr Leu Lys Asp
            980             985             990

Asp Ile Lys Ile Ser Leu Ser Leu Thr Leu Gln Asp Glu Lys Thr Ile
        995             1000            1005

Lys Leu Asn Ser Val His Leu Asp Glu Ser Gly Val Ala Glu Ile
    1010            1015            1020

Leu Lys Phe Met Asn Arg Lys Gly Asn Thr Asn Thr Ser Asp Ser
    1025            1030            1035

Leu Met Ser Phe Leu Glu Ser Met Asn Ile Lys Ser Ile Phe Val
    1040            1045            1050

Asn Phe Leu Gln Ser Asn Ile Lys Phe Ile Leu Asp Ala Asn Phe
    1055            1060            1065

Ile Ile Ser Gly Thr Thr Ser Ile Gly Gln Phe Glu Phe Ile Cys
    1070            1075            1080

Asp Glu Asn Asp Asn Ile Gln Pro Tyr Phe Ile Lys Phe Asn Thr
    1085            1090            1095

Leu Glu Thr Asn Tyr Thr Leu Tyr Val Gly Asn Arg Gln Asn Met
    1100            1105            1110

Ile Val Glu Pro Asn Tyr Asp Leu Asp Asp Ser Gly Asp Ile Ser
    1115            1120            1125

Ser Thr Val Ile Asn Phe Ser Gln Lys Tyr Leu Tyr Gly Ile Asp
    1130            1135            1140

Ser Cys Val Asn Lys Val Val Ile Ser Pro Asn Ile Tyr Thr Asp
    1145            1150            1155

Glu Ile Asn Ile Thr Pro Val Tyr Glu Thr Asn Asn Thr Tyr Pro
    1160            1165            1170

Glu Val Ile Val Leu Asp Ala Asn Tyr Ile Asn Glu Lys Ile Asn
    1175            1180            1185

Val Asn Ile Asn Asp Leu Ser Ile Arg Tyr Val Trp Ser Asn Asp
    1190            1195            1200

Gly Asn Asp Phe Ile Leu Met Ser Thr Ser Glu Glu Asn Lys Val
    1205            1210            1215

```
Ser Gln Val Lys Ile Arg Phe Val Asn Val Phe Lys Asp Lys Thr
    1220                1225                1230

Leu Ala Asn Lys Leu Ser Phe Asn Phe Ser Asp Lys Gln Asp Val
    1235                1240                1245

Pro Val Ser Glu Ile Ile Leu Ser Phe Thr Pro Ser Tyr Tyr Glu
    1250                1255                1260

Asp Gly Leu Ile Gly Tyr Asp Leu Gly Leu Val Ser Leu Tyr Asn
    1265                1270                1275

Glu Lys Phe Tyr Ile Asn Asn Phe Gly Met Met Val Ser Gly Leu
    1280                1285                1290

Ile Tyr Ile Asn Asp Ser Leu Tyr Tyr Phe Lys Pro Pro Val Asn
    1295                1300                1305

Asn Leu
    1310

<210> SEQ ID NO 11
<211> LENGTH: 1310
<212> TYPE: PRT
<213> ORGANISM: Artificial Sequence
<220> FEATURE:
<223> OTHER INFORMATION: C. difficile Toxin B (toxinotype 3) 543-1852

<400> SEQUENCE: 11

Leu Gly Glu Asp Asp Asn Leu Asp Phe Ser Gln Asn Thr Val Asp
1               5                   10                  15

Lys Glu Tyr Leu Leu Glu Lys Ile Ser Ser Leu Ala Arg Ser Ser
                20                  25                  30

Arg Gly Tyr Ile His Tyr Ile Val Gln Leu Gln Gly Asp Lys Ile Ser
                35                  40                  45

Tyr Glu Ala Ala Cys Asn Leu Phe Ala Lys Thr Pro Tyr Asp Ser Val
    50                  55                  60

Leu Phe Gln Lys Asn Ile Glu Asp Ser Glu Ile Ala Tyr Tyr Asn
65                  70                  75                  80

Pro Gly Asp Gly Glu Ile Gln Glu Ile Asp Lys Tyr Lys Ile Pro Ser
                    85                  90                  95

Ile Ile Ser Asp Arg Pro Lys Ile Lys Leu Thr Phe Ile Gly His Gly
                    100                 105                 110

Lys Asp Glu Phe Asn Thr Asp Ile Phe Ala Gly Leu Asp Val Asp Ser
                    115                 120                 125

Leu Ser Thr Glu Ile Glu Thr Ala Ile Asp Leu Ala Lys Glu Asp Ile
    130                 135                 140

Ser Pro Lys Ser Ile Glu Ile Asn Leu Leu Gly Cys Asn Met Phe Ser
145                 150                 155                 160

Tyr Ser Val Asn Val Glu Glu Thr Tyr Pro Gly Lys Leu Leu Leu Arg
                165                 170                 175

Val Lys Asp Lys Val Ser Glu Leu Met Pro Ser Ile Ser Gln Asp Ser
                180                 185                 190

Ile Ile Val Ser Ala Asn Gln Tyr Glu Val Arg Ile Asn Ser Glu Gly
                195                 200                 205

Arg Arg Glu Leu Leu Asp His Ser Gly Glu Trp Ile Asn Lys Glu Glu
    210                 215                 220

Ser Ile Ile Lys Asp Ile Ser Ser Lys Glu Tyr Ile Ser Phe Asn Pro
225                 230                 235                 240

Lys Glu Asn Lys Ile Ile Val Lys Ser Lys Asn Leu Pro Glu Leu Ser
                245                 250                 255
```

-continued

```
Thr Leu Leu Gln Glu Ile Arg Asn Asn Ser Asn Ser Ser Asp Ile Glu
            260                 265                 270

Leu Glu Glu Lys Val Met Leu Ala Glu Cys Glu Ile Asn Val Ile Ser
        275                 280                 285

Asn Ile Asp Thr Gln Val Val Glu Gly Arg Ile Glu Glu Ala Lys Ser
    290                 295                 300

Leu Thr Ser Asp Ser Ile Asn Tyr Ile Lys Asn Glu Phe Lys Leu Ile
305                 310                 315                 320

Glu Ser Ile Ser Asp Ala Leu Tyr Asp Leu Lys Gln Gln Asn Glu Leu
                325                 330                 335

Glu Glu Ser His Phe Ile Ser Phe Glu Asp Ile Leu Gly Thr Asp Glu
            340                 345                 350

Gly Phe Ser Ile Arg Phe Ile Asp Lys Glu Thr Gly Glu Ser Ile Phe
        355                 360                 365

Val Glu Thr Glu Lys Ala Ile Phe Ser Glu Tyr Ala Asn His Ile Thr
    370                 375                 380

Glu Glu Ile Ser Lys Ile Lys Gly Thr Ile Phe Asp Thr Val Asn Gly
385                 390                 395                 400

Lys Leu Val Lys Lys Val Asn Leu Asp Ala Thr His Glu Val Asn Thr
                405                 410                 415

Leu Asn Ala Ala Phe Phe Ile Gln Ser Leu Ile Glu Tyr Asn Ser Ser
            420                 425                 430

Lys Glu Ser Leu Ser Asn Leu Ser Val Ala Met Lys Val Gln Val Tyr
        435                 440                 445

Ala Gln Leu Phe Ser Thr Gly Leu Asn Thr Ile Thr Asp Ala Ala Lys
    450                 455                 460

Val Val Glu Leu Val Ser Thr Ala Leu Asp Glu Thr Ile Asp Leu Leu
465                 470                 475                 480

Pro Thr Leu Ser Glu Gly Leu Pro Val Ile Ala Thr Ile Ile Asp Gly
                485                 490                 495

Val Ser Leu Gly Ala Ala Ile Lys Glu Leu Ser Glu Thr Ser Asp Pro
            500                 505                 510

Leu Leu Arg Gln Glu Ile Glu Ala Lys Ile Gly Ile Met Ala Val Asn
        515                 520                 525

Leu Thr Ala Ala Thr Thr Ala Ile Ile Thr Ser Ser Leu Gly Ile Ala
    530                 535                 540

Ser Gly Phe Ser Ile Leu Leu Val Pro Leu Ala Gly Ile Ser Ala Gly
545                 550                 555                 560

Ile Pro Ser Leu Val Asn Asn Glu Leu Ile Leu Arg Asp Lys Ala Thr
                565                 570                 575

Lys Val Val Asp Tyr Phe Ser His Ile Ser Leu Ala Glu Ser Glu Gly
            580                 585                 590

Ala Phe Thr Ser Leu Asp Asp Lys Ile Met Met Pro Gln Asp Asp Leu
        595                 600                 605

Val Ile Ser Glu Ile Asp Phe Asn Asn Ser Ile Thr Leu Gly Lys
    610                 615                 620

Cys Glu Ile Trp Arg Met Glu Gly Gly Ser Gly His Thr Val Thr Asp
625                 630                 635                 640

Asp Ile Asp His Phe Phe Ser Ala Pro Ser Ile Thr Tyr Arg Glu Pro
                645                 650                 655

His Leu Ser Ile Tyr Asp Val Leu Glu Val Gln Lys Glu Glu Leu Asp
            660                 665                 670

Leu Ser Lys Asp Leu Met Val Leu Pro Asn Ala Pro Asn Arg Val Phe
```

```
                675                 680                 685
Ala Trp Glu Thr Gly Trp Thr Pro Gly Leu Arg Ser Leu Glu Asn Asp
690                 695                 700
Gly Thr Lys Leu Leu Asp Arg Ile Arg Asp Asn Tyr Glu Gly Glu Phe
705                 710                 715                 720
Tyr Trp Arg Tyr Phe Ala Phe Ile Ala Asp Ala Leu Ile Thr Thr Leu
                725                 730                 735
Lys Pro Arg Tyr Glu Asp Thr Asn Ile Arg Ile Asn Leu Asp Ser Asn
                740                 745                 750
Thr Arg Ser Phe Ile Val Pro Val Ile Thr Thr Glu Tyr Ile Arg Glu
                755                 760                 765
Lys Leu Ser Tyr Ser Phe Tyr Gly Ser Gly Gly Thr Tyr Ala Leu Ser
                770                 775                 780
Leu Ser Gln Tyr Asn Met Asn Ile Asn Ile Glu Leu Asn Glu Asn Asp
785                 790                 795                 800
Thr Trp Val Ile Asp Val Asp Asn Val Val Arg Asp Val Thr Ile Glu
                805                 810                 815
Ser Asp Lys Ile Lys Lys Gly Asp Leu Ile Glu Asn Ile Leu Ser Lys
                820                 825                 830
Leu Ser Ile Glu Asp Asn Lys Ile Ile Leu Asp Asn His Glu Ile Asn
                835                 840                 845
Phe Ser Gly Thr Leu Asn Gly Gly Asn Gly Phe Val Ser Leu Thr Phe
850                 855                 860
Ser Ile Leu Glu Gly Ile Asn Ala Val Ile Glu Val Asp Leu Leu Ser
865                 870                 875                 880
Lys Ser Tyr Lys Val Leu Ile Ser Gly Glu Leu Lys Thr Leu Met Ala
                885                 890                 895
Asn Ser Asn Ser Val Gln Gln Lys Ile Asp Tyr Ile Gly Leu Asn Ser
                900                 905                 910
Glu Leu Gln Lys Asn Ile Pro Tyr Ser Phe Met Asp Asp Lys Gly Lys
                915                 920                 925
Glu Asn Gly Phe Ile Asn Cys Ser Thr Lys Glu Gly Leu Phe Val Ser
930                 935                 940
Glu Leu Ser Asp Val Val Leu Ile Ser Lys Val Tyr Met Asp Asn Ser
945                 950                 955                 960
Lys Pro Leu Phe Gly Tyr Cys Ser Asn Asp Leu Lys Asp Val Lys Val
                965                 970                 975
Ile Thr Lys Asp Asp Val Ile Ile Leu Thr Gly Tyr Tyr Leu Lys Asp
                980                 985                 990
Asp Ile Lys Ile Ser Leu Ser Phe Thr Ile Gln Asp Glu Asn Thr Ile
                995                 1000                1005
Lys Leu Asn Gly Val Tyr Leu Asp Glu Asn Gly Val Ala Glu Ile
                1010                1015                1020
Leu Lys Phe Met Asn Lys Lys Gly Ser Thr Asn Thr Ser Asp Ser
                1025                1030                1035
Leu Met Ser Phe Leu Glu Ser Met Asn Ile Lys Ser Ile Phe Ile
                1040                1045                1050
Asn Ser Leu Gln Ser Asn Thr Lys Leu Ile Leu Asp Thr Asn Phe
                1055                1060                1065
Ile Ile Ser Gly Thr Thr Ser Ile Gly Gln Phe Glu Phe Ile Cys
                1070                1075                1080
Asp Lys Asp Asn Asn Ile Gln Pro Tyr Phe Ile Lys Phe Asn Thr
                1085                1090                1095
```

```
Leu Glu Thr Lys Tyr Thr Leu Tyr Val Gly Asn Arg Gln Asn Met
         1100                1105                1110

Ile Val Glu Pro Asn Tyr Asp Leu Asp Asp Ser Gly Asp Ile Ser
         1115                1120                1125

Ser Thr Val Ile Asn Phe Ser Gln Lys Tyr Leu Tyr Gly Ile Asp
         1130                1135                1140

Ser Cys Val Asn Lys Val Ile Ile Ser Pro Asn Ile Tyr Thr Asp
         1145                1150                1155

Glu Ile Asn Ile Thr Pro Ile Tyr Glu Ala Asn Asn Thr Tyr Pro
         1160                1165                1170

Glu Val Ile Val Leu Asp Thr Asn Tyr Ile Ser Glu Lys Ile Asn
         1175                1180                1185

Ile Asn Ile Asn Asp Leu Ser Ile Arg Tyr Val Trp Ser Asn Asp
         1190                1195                1200

Gly Ser Asp Phe Ile Leu Met Ser Thr Asp Glu Glu Asn Lys Val
         1205                1210                1215

Ser Gln Val Lys Ile Arg Phe Thr Asn Val Phe Lys Gly Asn Thr
         1220                1225                1230

Ile Ser Asp Lys Ile Ser Phe Asn Phe Ser Asp Lys Gln Asp Val
         1235                1240                1245

Ser Ile Asn Lys Val Ile Ser Thr Phe Thr Pro Ser Tyr Tyr Val
         1250                1255                1260

Glu Gly Leu Leu Asn Tyr Asp Leu Gly Leu Ile Ser Leu Tyr Asn
         1265                1270                1275

Glu Lys Phe Tyr Ile Asn Asn Phe Gly Met Met Val Ser Gly Leu
         1280                1285                1290

Val Tyr Ile Asn Asp Ser Leu Tyr Tyr Phe Lys Pro Pro Ile Lys
         1295                1300                1305

Asn Leu
    1310

<210> SEQ ID NO 12
<211> LENGTH: 1310
<212> TYPE: PRT
<213> ORGANISM: Artificial Sequence
<220> FEATURE:
<223> OTHER INFORMATION: C. difficile Toxin B 543-1852 Cysteine protease
      negative

<400> SEQUENCE: 12

Leu Gly Glu Asp Asp Asn Leu Asp Phe Ser Gln Asn Ile Val Val Asp
1               5                   10                  15

Lys Glu Tyr Leu Leu Glu Lys Ile Ser Ser Leu Ala Arg Ser Ser Glu
            20                  25                  30

Arg Gly Tyr Ile His Tyr Ile Val Gln Leu Gln Gly Asp Lys Ile Ser
        35                  40                  45

Tyr Glu Ala Ala Cys Asn Leu Phe Ala Lys Thr Pro Tyr Asp Ser Val
    50                  55                  60

Leu Phe Gln Lys Asn Ile Glu Asp Ser Glu Ile Ala Tyr Tyr Tyr Asn
65                  70                  75                  80

Pro Gly Asp Gly Glu Ile Gln Glu Ile Asp Lys Tyr Lys Ile Pro Ser
                85                  90                  95

Ile Ile Ser Asp Arg Pro Lys Ile Lys Leu Thr Phe Ile Gly His Gly
            100                 105                 110

Lys Asp Glu Phe Asn Thr Asp Ile Phe Ala Gly Phe Asp Val Asp Ser
```

```
            115                 120                 125
Leu Ser Thr Glu Ile Glu Ala Ala Ile Asp Leu Ala Lys Glu Asp Ile
        130                 135                 140

Ser Pro Lys Ser Ile Glu Ile Asn Leu Leu Gly Ala Asn Met Phe Ser
145                 150                 155                 160

Tyr Ser Ile Asn Val Glu Glu Thr Tyr Pro Gly Lys Leu Leu Leu Lys
                165                 170                 175

Val Lys Asp Lys Ile Ser Glu Leu Met Pro Ser Ile Ser Gln Asp Ser
            180                 185                 190

Ile Ile Val Ser Ala Asn Gln Tyr Glu Val Arg Ile Asn Ser Glu Gly
        195                 200                 205

Arg Arg Glu Leu Leu Asp His Ser Gly Glu Trp Ile Asn Lys Glu Glu
    210                 215                 220

Ser Ile Ile Lys Asp Ile Ser Ser Lys Glu Tyr Ile Ser Phe Asn Pro
225                 230                 235                 240

Lys Glu Asn Lys Ile Thr Val Lys Ser Lys Asn Leu Pro Glu Leu Ser
                245                 250                 255

Thr Leu Leu Gln Glu Ile Arg Asn Asn Ser Asn Ser Ser Asp Ile Glu
            260                 265                 270

Leu Glu Glu Lys Val Met Leu Thr Glu Cys Glu Ile Asn Val Ile Ser
        275                 280                 285

Asn Ile Asp Thr Gln Ile Val Glu Glu Arg Ile Glu Glu Ala Lys Asn
    290                 295                 300

Leu Thr Ser Asp Ser Ile Asn Tyr Ile Lys Asp Glu Phe Lys Leu Ile
305                 310                 315                 320

Glu Ser Ile Ser Asp Ala Leu Cys Asp Leu Lys Gln Gln Asn Glu Leu
                325                 330                 335

Glu Asp Ser His Phe Ile Ser Phe Glu Asp Ile Ser Glu Thr Asp Glu
            340                 345                 350

Gly Phe Ser Ile Arg Phe Ile Asn Lys Glu Thr Gly Glu Ser Ile Phe
        355                 360                 365

Val Glu Thr Glu Lys Thr Ile Phe Ser Glu Tyr Ala Asn His Ile Thr
    370                 375                 380

Glu Glu Ile Ser Lys Ile Lys Gly Thr Ile Phe Asp Thr Val Asn Gly
385                 390                 395                 400

Lys Leu Val Lys Lys Val Asn Leu Asp Thr Thr His Glu Val Asn Thr
                405                 410                 415

Leu Asn Ala Ala Phe Phe Ile Gln Ser Leu Ile Glu Tyr Asn Ser Ser
            420                 425                 430

Lys Glu Ser Leu Ser Asn Leu Ser Val Ala Met Lys Val Gln Val Tyr
        435                 440                 445

Ala Gln Leu Phe Ser Thr Gly Leu Asn Thr Ile Thr Asp Ala Ala Lys
    450                 455                 460

Val Val Glu Leu Val Ser Thr Ala Leu Asp Glu Thr Ile Asp Leu Leu
465                 470                 475                 480

Pro Thr Leu Ser Glu Gly Leu Pro Ile Ile Ala Thr Ile Ile Asp Gly
                485                 490                 495

Val Ser Leu Gly Ala Ala Ile Lys Glu Leu Ser Glu Thr Ser Asp Pro
            500                 505                 510

Leu Leu Arg Gln Glu Ile Glu Ala Lys Ile Gly Ile Met Ala Val Asn
        515                 520                 525

Leu Thr Thr Ala Thr Thr Ala Ile Ile Thr Ser Ser Leu Gly Ile Ala
    530                 535                 540
```

```
Ser Gly Phe Ser Ile Leu Leu Val Pro Leu Ala Gly Ile Ser Ala Gly
545                 550                 555                 560

Ile Pro Ser Leu Val Asn Asn Glu Leu Val Leu Arg Asp Lys Ala Thr
            565                 570                 575

Lys Val Val Asp Tyr Phe Lys His Val Ser Leu Val Glu Thr Glu Gly
                580                 585                 590

Val Phe Thr Leu Leu Asp Asp Lys Ile Met Met Pro Gln Asp Asp Leu
            595                 600                 605

Val Ile Ser Glu Ile Asp Phe Asn Asn Asn Ser Ile Val Leu Gly Lys
        610                 615                 620

Cys Glu Ile Trp Arg Met Glu Gly Gly Ser Gly His Thr Val Thr Asp
625                 630                 635                 640

Asp Ile Asp His Phe Phe Ser Ala Pro Ser Ile Thr Tyr Arg Glu Pro
                645                 650                 655

His Leu Ser Ile Tyr Asp Val Leu Glu Val Gln Lys Glu Glu Leu Asp
            660                 665                 670

Leu Ser Lys Asp Leu Met Val Leu Pro Asn Ala Pro Asn Arg Val Phe
        675                 680                 685

Ala Trp Glu Thr Gly Trp Thr Pro Gly Leu Arg Ser Leu Glu Asn Asp
690                 695                 700

Gly Thr Lys Leu Leu Asp Arg Ile Arg Asp Asn Tyr Glu Gly Glu Phe
705                 710                 715                 720

Tyr Trp Arg Tyr Phe Ala Phe Ile Ala Asp Ala Leu Ile Thr Thr Leu
                725                 730                 735

Lys Pro Arg Tyr Glu Asp Thr Asn Ile Arg Ile Asn Leu Asp Ser Asn
            740                 745                 750

Thr Arg Ser Phe Ile Val Pro Ile Ile Thr Thr Glu Tyr Ile Arg Glu
        755                 760                 765

Lys Leu Ser Tyr Ser Phe Tyr Gly Ser Gly Thr Tyr Ala Leu Ser
770                 775                 780

Leu Ser Gln Tyr Asn Met Gly Ile Asn Ile Glu Leu Ser Glu Ser Asp
785                 790                 795                 800

Val Trp Ile Ile Asp Val Asp Asn Val Val Arg Asp Val Thr Ile Glu
                805                 810                 815

Ser Asp Lys Ile Lys Lys Gly Asp Leu Ile Glu Gly Ile Leu Ser Thr
            820                 825                 830

Leu Ser Ile Glu Glu Asn Lys Ile Ile Leu Asn Ser His Glu Ile Asn
        835                 840                 845

Phe Ser Gly Glu Val Asn Gly Ser Asn Gly Phe Val Ser Leu Thr Phe
850                 855                 860

Ser Ile Leu Glu Gly Ile Asn Ala Ile Glu Val Asp Leu Leu Ser
865                 870                 875                 880

Lys Ser Tyr Lys Leu Leu Ile Ser Gly Glu Leu Lys Ile Leu Met Leu
                885                 890                 895

Asn Ser Asn His Ile Gln Gln Lys Ile Asp Tyr Ile Gly Phe Asn Ser
            900                 905                 910

Glu Leu Gln Lys Asn Ile Pro Tyr Ser Phe Val Asp Ser Glu Gly Lys
        915                 920                 925

Glu Asn Gly Phe Ile Asn Gly Ser Thr Lys Glu Gly Leu Phe Val Ser
930                 935                 940

Glu Leu Pro Asp Val Val Leu Ile Ser Lys Val Tyr Met Asp Asp Ser
945                 950                 955                 960
```

Lys Pro Ser Phe Gly Tyr Tyr Ser Asn Asn Leu Lys Asp Val Lys Val
                965                 970                 975

Ile Thr Lys Asp Asn Val Asn Ile Leu Thr Gly Tyr Tyr Leu Lys Asp
            980                 985                 990

Asp Ile Lys Ile Ser Leu Ser Leu Thr Leu Gln Asp Glu Lys Thr Ile
        995                 1000                1005

Lys Leu Asn Ser Val His Leu Asp Glu Ser Gly Val Ala Glu Ile
    1010                1015                1020

Leu Lys Phe Met Asn Arg Lys Gly Asn Thr Asn Thr Ser Asp Ser
    1025                1030                1035

Leu Met Ser Phe Leu Glu Ser Met Asn Ile Lys Ser Ile Phe Val
    1040                1045                1050

Asn Phe Leu Gln Ser Asn Ile Lys Phe Ile Leu Asp Ala Asn Phe
    1055                1060                1065

Ile Ile Ser Gly Thr Thr Ser Ile Gly Gln Phe Glu Phe Ile Cys
    1070                1075                1080

Asp Glu Asn Asp Asn Ile Gln Pro Tyr Phe Ile Lys Phe Asn Thr
    1085                1090                1095

Leu Glu Thr Asn Tyr Thr Leu Tyr Val Gly Asn Arg Gln Asn Met
    1100                1105                1110

Ile Val Glu Pro Asn Tyr Asp Leu Asp Asp Ser Gly Asp Ile Ser
    1115                1120                1125

Ser Thr Val Ile Asn Phe Ser Gln Lys Tyr Leu Tyr Gly Ile Asp
    1130                1135                1140

Ser Cys Val Asn Lys Val Val Ile Ser Pro Asn Ile Tyr Thr Asp
    1145                1150                1155

Glu Ile Asn Ile Thr Pro Val Tyr Glu Thr Asn Asn Thr Tyr Pro
    1160                1165                1170

Glu Val Ile Val Leu Asp Ala Asn Tyr Ile Asn Glu Lys Ile Asn
    1175                1180                1185

Val Asn Ile Asn Asp Leu Ser Ile Arg Tyr Val Trp Ser Asn Asp
    1190                1195                1200

Gly Asn Asp Phe Ile Leu Met Ser Thr Ser Glu Glu Asn Lys Val
    1205                1210                1215

Ser Gln Val Lys Ile Arg Phe Val Asn Val Phe Lys Asp Lys Thr
    1220                1225                1230

Leu Ala Asn Lys Leu Ser Phe Asn Phe Ser Asp Lys Gln Asp Val
    1235                1240                1245

Pro Val Ser Glu Ile Ile Leu Ser Phe Thr Pro Ser Tyr Tyr Glu
    1250                1255                1260

Asp Gly Leu Ile Gly Tyr Asp Leu Gly Leu Val Ser Leu Tyr Asn
    1265                1270                1275

Glu Lys Phe Tyr Ile Asn Asn Phe Gly Met Met Val Ser Gly Leu
    1280                1285                1290

Ile Tyr Ile Asn Asp Ser Leu Tyr Tyr Phe Lys Pro Pro Val Asn
    1295                1300                1305

Asn Leu
    1310

<210> SEQ ID NO 13
<211> LENGTH: 1086
<212> TYPE: PRT
<213> ORGANISM: Artificial Sequence
<220> FEATURE:
<223> OTHER INFORMATION: C. difficile Toxin B 767-1852

<400> SEQUENCE: 13

```
Ser Ile Ile Lys Asp Ile Ser Ser Lys Glu Tyr Ile Ser Phe Asn Pro
1               5                   10                  15

Lys Glu Asn Lys Ile Thr Val Lys Ser Lys Asn Leu Pro Glu Leu Ser
            20                  25                  30

Thr Leu Leu Gln Glu Ile Arg Asn Asn Ser Asn Ser Ser Asp Ile Glu
        35                  40                  45

Leu Glu Glu Lys Val Met Leu Thr Glu Cys Glu Ile Asn Val Ile Ser
    50                  55                  60

Asn Ile Asp Thr Gln Ile Val Glu Glu Arg Ile Glu Glu Ala Lys Asn
65                  70                  75                  80

Leu Thr Ser Asp Ser Ile Asn Tyr Ile Lys Asp Glu Phe Lys Leu Ile
                85                  90                  95

Glu Ser Ile Ser Asp Ala Leu Cys Asp Leu Lys Gln Gln Asn Glu Leu
            100                 105                 110

Glu Asp Ser His Phe Ile Ser Phe Glu Asp Ile Ser Thr Asp Glu
            115                 120                 125

Gly Phe Ser Ile Arg Phe Ile Asn Lys Glu Thr Gly Glu Ser Ile Phe
130                 135                 140

Val Glu Thr Glu Lys Thr Ile Phe Ser Glu Tyr Ala Asn His Ile Thr
145                 150                 155                 160

Glu Glu Ile Ser Lys Ile Lys Gly Thr Ile Phe Asp Thr Val Asn Gly
                165                 170                 175

Lys Leu Val Lys Lys Val Asn Leu Asp Thr Thr His Glu Val Asn Thr
            180                 185                 190

Leu Asn Ala Ala Phe Phe Ile Gln Ser Leu Ile Glu Tyr Asn Ser Ser
        195                 200                 205

Lys Glu Ser Leu Ser Asn Leu Ser Val Ala Met Lys Val Gln Val Tyr
    210                 215                 220

Ala Gln Leu Phe Ser Thr Gly Leu Asn Thr Ile Thr Asp Ala Ala Lys
225                 230                 235                 240

Val Val Glu Leu Val Ser Thr Ala Leu Asp Glu Thr Ile Asp Leu Leu
                245                 250                 255

Pro Thr Leu Ser Glu Gly Leu Pro Ile Ile Ala Thr Ile Ile Asp Gly
            260                 265                 270

Val Ser Leu Gly Ala Ala Ile Lys Glu Leu Ser Glu Thr Ser Asp Pro
        275                 280                 285

Leu Leu Arg Gln Glu Ile Glu Ala Lys Ile Gly Ile Met Ala Val Asn
    290                 295                 300

Leu Thr Thr Ala Thr Thr Ala Ile Ile Thr Ser Ser Leu Gly Ile Ala
305                 310                 315                 320

Ser Gly Phe Ser Ile Leu Leu Val Pro Leu Ala Gly Ile Ser Ala Gly
                325                 330                 335

Ile Pro Ser Leu Val Asn Asn Glu Leu Val Leu Arg Asp Lys Ala Thr
            340                 345                 350

Lys Val Val Asp Tyr Phe Lys His Val Ser Leu Val Glu Thr Glu Gly
        355                 360                 365

Val Phe Thr Leu Leu Asp Asp Lys Ile Met Met Pro Gln Asp Asp Leu
    370                 375                 380

Val Ile Ser Glu Ile Asp Phe Asn Asn Asn Ser Ile Val Leu Gly Lys
385                 390                 395                 400

Cys Glu Ile Trp Arg Met Glu Gly Gly Ser Gly His Thr Val Thr Asp
```

-continued

```
                405                 410                 415
Asp Ile Asp His Phe Ser Ala Pro Ser Ile Thr Tyr Arg Glu Pro
            420                 425                 430

His Leu Ser Ile Tyr Asp Val Leu Glu Val Gln Lys Glu Glu Leu Asp
        435                 440                 445

Leu Ser Lys Asp Leu Met Val Leu Pro Asn Ala Pro Asn Arg Val Phe
450                 455                 460

Ala Trp Glu Thr Gly Trp Thr Pro Gly Leu Arg Ser Leu Glu Asn Asp
465                 470                 475                 480

Gly Thr Lys Leu Leu Asp Arg Ile Arg Asp Asn Tyr Glu Gly Glu Phe
                485                 490                 495

Tyr Trp Arg Tyr Phe Ala Phe Ile Ala Asp Ala Leu Ile Thr Thr Leu
            500                 505                 510

Lys Pro Arg Tyr Glu Asp Thr Asn Ile Arg Ile Asn Leu Asp Ser Asn
        515                 520                 525

Thr Arg Ser Phe Ile Val Pro Ile Ile Thr Thr Glu Tyr Ile Arg Glu
    530                 535                 540

Lys Leu Ser Tyr Ser Phe Tyr Gly Ser Gly Gly Thr Tyr Ala Leu Ser
545                 550                 555                 560

Leu Ser Gln Tyr Asn Met Gly Ile Asn Ile Glu Leu Ser Glu Ser Asp
                565                 570                 575

Val Trp Ile Ile Asp Val Asp Asn Val Val Arg Asp Val Thr Ile Glu
            580                 585                 590

Ser Asp Lys Ile Lys Lys Gly Asp Leu Ile Glu Gly Ile Leu Ser Thr
        595                 600                 605

Leu Ser Ile Glu Glu Asn Lys Ile Ile Leu Asn Ser His Glu Ile Asn
    610                 615                 620

Phe Ser Gly Glu Val Asn Gly Ser Asn Gly Phe Val Ser Leu Thr Phe
625                 630                 635                 640

Ser Ile Leu Glu Gly Ile Asn Ala Ile Ile Glu Val Asp Leu Leu Ser
                645                 650                 655

Lys Ser Tyr Lys Leu Leu Ile Ser Gly Glu Leu Lys Ile Leu Met Leu
            660                 665                 670

Asn Ser Asn His Ile Gln Gln Lys Ile Asp Tyr Ile Gly Phe Asn Ser
        675                 680                 685

Glu Leu Gln Lys Asn Ile Pro Tyr Ser Phe Val Asp Ser Glu Gly Lys
    690                 695                 700

Glu Asn Gly Phe Ile Asn Gly Ser Thr Lys Glu Gly Leu Phe Val Ser
705                 710                 715                 720

Glu Leu Pro Asp Val Val Leu Ile Ser Lys Val Tyr Met Asp Asp Ser
                725                 730                 735

Lys Pro Ser Phe Gly Tyr Tyr Ser Asn Asn Leu Lys Asp Val Lys Val
            740                 745                 750

Ile Thr Lys Asp Asn Val Asn Ile Leu Thr Gly Tyr Tyr Leu Lys Asp
        755                 760                 765

Asp Ile Lys Ile Ser Leu Ser Leu Thr Leu Gln Asp Glu Lys Thr Ile
    770                 775                 780

Lys Leu Asn Ser Val His Leu Asp Glu Ser Gly Val Ala Glu Ile Leu
785                 790                 795                 800

Lys Phe Met Asn Arg Lys Gly Asn Thr Asn Thr Ser Asp Ser Leu Met
                805                 810                 815

Ser Phe Leu Glu Ser Met Asn Ile Lys Ser Ile Phe Val Asn Phe Leu
            820                 825                 830
```

```
Gln Ser Asn Ile Lys Phe Ile Leu Asp Ala Asn Phe Ile Ile Ser Gly
        835                 840                 845

Thr Thr Ser Ile Gly Gln Phe Glu Phe Ile Cys Asp Glu Asn Asp Asn
    850                 855                 860

Ile Gln Pro Tyr Phe Ile Lys Phe Asn Thr Leu Glu Thr Asn Tyr Thr
865                 870                 875                 880

Leu Tyr Val Gly Asn Arg Gln Asn Met Ile Val Glu Pro Asn Tyr Asp
            885                 890                 895

Leu Asp Asp Ser Gly Asp Ile Ser Ser Thr Val Ile Asn Phe Ser Gln
            900                 905                 910

Lys Tyr Leu Tyr Gly Ile Asp Ser Cys Val Asn Lys Val Val Ile Ser
        915                 920                 925

Pro Asn Ile Tyr Thr Asp Glu Ile Asn Ile Thr Pro Val Tyr Glu Thr
    930                 935                 940

Asn Asn Thr Tyr Pro Glu Val Ile Val Leu Asp Ala Asn Tyr Ile Asn
945                 950                 955                 960

Glu Lys Ile Asn Val Asn Ile Asn Asp Leu Ser Ile Arg Tyr Val Trp
            965                 970                 975

Ser Asn Asp Gly Asn Asp Phe Ile Leu Met Ser Thr Ser Glu Glu Asn
            980                 985                 990

Lys Val Ser Gln Val Lys Ile Arg Phe Val Asn Val Phe Lys Asp Lys
        995                 1000                1005

Thr Leu Ala Asn Lys Leu Ser Phe Asn Phe Ser Asp Lys Gln Asp
    1010                1015                1020

Val Pro Val Ser Glu Ile Ile Leu Ser Phe Thr Pro Ser Tyr Tyr
    1025                1030                1035

Glu Asp Gly Leu Ile Gly Tyr Asp Leu Gly Leu Val Ser Leu Tyr
    1040                1045                1050

Asn Glu Lys Phe Tyr Ile Asn Asn Phe Gly Met Met Val Ser Gly
    1055                1060                1065

Leu Ile Tyr Ile Asn Asp Ser Leu Tyr Tyr Phe Lys Pro Pro Val
    1070                1075                1080

Asn Asn Leu
    1085

<210> SEQ ID NO 14
<211> LENGTH: 708
<212> TYPE: PRT
<213> ORGANISM: Artificial Sequence
<220> FEATURE:
<223> OTHER INFORMATION: C. difficile Toxin B 1145-1852

<400> SEQUENCE: 14

Met Pro Gln Asp Asp Leu Val Ile Ser Glu Ile Asp Phe Asn Asn Asn
1               5                   10                  15

Ser Ile Val Leu Gly Lys Cys Glu Ile Trp Arg Met Glu Gly Gly Ser
            20                  25                  30

Gly His Thr Val Thr Asp Asp Ile Asp His Phe Phe Ser Ala Pro Ser
        35                  40                  45

Ile Thr Tyr Arg Glu Pro His Leu Ser Ile Tyr Asp Val Leu Glu Val
    50                  55                  60

Gln Lys Glu Glu Leu Asp Leu Ser Lys Asp Leu Met Val Leu Pro Asn
65                  70                  75                  80

Ala Pro Asn Arg Val Phe Ala Trp Glu Thr Gly Trp Thr Pro Gly Leu
                85                  90                  95
```

-continued

```
Arg Ser Leu Glu Asn Asp Gly Thr Lys Leu Leu Asp Arg Ile Arg Asp
            100                 105                 110

Asn Tyr Glu Gly Glu Phe Tyr Trp Arg Tyr Phe Ala Phe Ile Ala Asp
            115                 120                 125

Ala Leu Ile Thr Thr Leu Lys Pro Arg Tyr Glu Asp Thr Asn Ile Arg
        130                 135                 140

Ile Asn Leu Asp Ser Asn Thr Arg Ser Phe Ile Val Pro Ile Ile Thr
145                 150                 155                 160

Thr Glu Tyr Ile Arg Glu Lys Leu Ser Tyr Ser Phe Tyr Gly Ser Gly
                165                 170                 175

Gly Thr Tyr Ala Leu Ser Leu Ser Gln Tyr Asn Met Gly Ile Asn Ile
            180                 185                 190

Glu Leu Ser Glu Ser Asp Val Trp Ile Ile Asp Val Asp Asn Val Val
        195                 200                 205

Arg Asp Val Thr Ile Glu Ser Asp Lys Ile Lys Lys Gly Asp Leu Ile
    210                 215                 220

Glu Gly Ile Leu Ser Thr Leu Ser Ile Glu Glu Asn Lys Ile Ile Leu
225                 230                 235                 240

Asn Ser His Glu Ile Asn Phe Ser Gly Glu Val Asn Gly Ser Asn Gly
                245                 250                 255

Phe Val Ser Leu Thr Phe Ser Ile Leu Glu Gly Ile Asn Ala Ile Ile
            260                 265                 270

Glu Val Asp Leu Leu Ser Lys Ser Tyr Lys Leu Leu Ile Ser Gly Glu
        275                 280                 285

Leu Lys Ile Leu Met Leu Asn Ser Asn His Ile Gln Gln Lys Ile Asp
    290                 295                 300

Tyr Ile Gly Phe Asn Ser Glu Leu Gln Lys Asn Ile Pro Tyr Ser Phe
305                 310                 315                 320

Val Asp Ser Glu Gly Lys Glu Asn Gly Phe Ile Asn Gly Ser Thr Lys
                325                 330                 335

Glu Gly Leu Phe Val Ser Glu Leu Pro Asp Val Val Leu Ile Ser Lys
            340                 345                 350

Val Tyr Met Asp Asp Ser Lys Pro Ser Phe Gly Tyr Tyr Ser Asn Asn
        355                 360                 365

Leu Lys Asp Val Lys Val Ile Thr Lys Asp Asn Val Asn Ile Leu Thr
    370                 375                 380

Gly Tyr Tyr Leu Lys Asp Asp Ile Lys Ile Ser Leu Ser Leu Thr Leu
385                 390                 395                 400

Gln Asp Glu Lys Thr Ile Lys Leu Asn Ser Val His Leu Asp Glu Ser
                405                 410                 415

Gly Val Ala Glu Ile Leu Lys Phe Met Asn Arg Lys Gly Asn Thr Asn
            420                 425                 430

Thr Ser Asp Ser Leu Met Ser Phe Leu Glu Ser Met Asn Ile Lys Ser
        435                 440                 445

Ile Phe Val Asn Phe Leu Gln Ser Asn Ile Lys Phe Ile Leu Asp Ala
    450                 455                 460

Asn Phe Ile Ile Ser Gly Thr Thr Ser Ile Gly Gln Phe Glu Phe Ile
465                 470                 475                 480

Cys Asp Glu Asn Asp Asn Ile Gln Pro Tyr Phe Ile Lys Phe Asn Thr
                485                 490                 495

Leu Glu Thr Asn Tyr Thr Leu Tyr Val Gly Asn Arg Gln Asn Met Ile
            500                 505                 510
```

Val Glu Pro Asn Tyr Asp Leu Asp Asp Ser Gly Asp Ile Ser Ser Thr
            515                 520                 525

Val Ile Asn Phe Ser Gln Lys Tyr Leu Tyr Gly Ile Asp Ser Cys Val
    530                 535                 540

Asn Lys Val Val Ile Ser Pro Asn Ile Tyr Thr Asp Glu Ile Asn Ile
545                 550                 555                 560

Thr Pro Val Tyr Glu Thr Asn Asn Thr Tyr Pro Glu Val Ile Val Leu
                565                 570                 575

Asp Ala Asn Tyr Ile Asn Glu Lys Ile Asn Val Asn Ile Asn Asp Leu
            580                 585                 590

Ser Ile Arg Tyr Val Trp Ser Asn Asp Gly Asn Asp Phe Ile Leu Met
        595                 600                 605

Ser Thr Ser Glu Glu Asn Lys Val Ser Gln Val Lys Ile Arg Phe Val
    610                 615                 620

Asn Val Phe Lys Asp Lys Thr Leu Ala Asn Lys Leu Ser Phe Asn Phe
625                 630                 635                 640

Ser Asp Lys Gln Asp Val Pro Val Ser Glu Ile Ile Leu Ser Phe Thr
                645                 650                 655

Pro Ser Tyr Tyr Glu Asp Gly Leu Ile Gly Tyr Asp Leu Gly Leu Val
            660                 665                 670

Ser Leu Tyr Asn Glu Lys Phe Tyr Ile Asn Asn Phe Gly Met Met Val
        675                 680                 685

Ser Gly Leu Ile Tyr Ile Asn Asp Ser Leu Tyr Tyr Phe Lys Pro Pro
    690                 695                 700

Val Asn Asn Leu
705

<210> SEQ ID NO 15
<211> LENGTH: 503
<212> TYPE: PRT
<213> ORGANISM: Artificial Sequence
<220> FEATURE:
<223> OTHER INFORMATION: C. difficile Toxin B 1350-1852

<400> SEQUENCE: 15

Asn Val Val Arg Asp Val Thr Ile Glu Ser Asp Lys Ile Lys Lys Gly
1               5                   10                  15

Asp Leu Ile Glu Gly Ile Leu Ser Thr Leu Ser Ile Glu Glu Asn Lys
            20                  25                  30

Ile Ile Leu Asn Ser His Glu Ile Asn Phe Ser Gly Glu Val Asn Gly
        35                  40                  45

Ser Asn Gly Phe Val Ser Leu Thr Phe Ser Ile Leu Glu Gly Ile Asn
    50                  55                  60

Ala Ile Ile Glu Val Asp Leu Leu Ser Lys Ser Tyr Lys Leu Leu Ile
65                  70                  75                  80

Ser Gly Glu Leu Lys Ile Leu Met Leu Asn Ser Asn His Ile Gln Gln
                85                  90                  95

Lys Ile Asp Tyr Ile Gly Phe Asn Ser Glu Leu Gln Lys Asn Ile Pro
            100                 105                 110

Tyr Ser Phe Val Asp Ser Glu Gly Lys Glu Asn Gly Phe Ile Asn Gly
        115                 120                 125

Ser Thr Lys Glu Gly Leu Phe Val Ser Glu Leu Pro Asp Val Val Leu
    130                 135                 140

Ile Ser Lys Val Tyr Met Asp Asp Ser Lys Pro Ser Phe Gly Tyr Tyr
145                 150                 155                 160

```
Ser Asn Asn Leu Lys Asp Val Lys Val Ile Thr Lys Asp Asn Val Asn
                165                 170                 175

Ile Leu Thr Gly Tyr Tyr Leu Lys Asp Ile Lys Ile Ser Leu Ser
            180                 185                 190

Leu Thr Leu Gln Asp Glu Lys Thr Ile Lys Leu Asn Ser Val His Leu
        195                 200                 205

Asp Glu Ser Gly Val Ala Glu Ile Leu Lys Phe Met Asn Arg Lys Gly
    210                 215                 220

Asn Thr Asn Thr Ser Asp Ser Leu Met Ser Phe Leu Glu Ser Met Asn
225                 230                 235                 240

Ile Lys Ser Ile Phe Val Asn Phe Leu Gln Ser Asn Ile Lys Phe Ile
                245                 250                 255

Leu Asp Ala Asn Phe Ile Ile Ser Gly Thr Thr Ser Ile Gly Gln Phe
            260                 265                 270

Glu Phe Ile Cys Asp Glu Asn Asp Asn Ile Gln Pro Tyr Phe Ile Lys
        275                 280                 285

Phe Asn Thr Leu Glu Thr Asn Tyr Thr Leu Tyr Val Gly Asn Arg Gln
    290                 295                 300

Asn Met Ile Val Glu Pro Asn Tyr Asp Leu Asp Asp Ser Gly Asp Ile
305                 310                 315                 320

Ser Ser Thr Val Ile Asn Phe Ser Gln Lys Tyr Leu Tyr Gly Ile Asp
                325                 330                 335

Ser Cys Val Asn Lys Val Val Ile Ser Pro Asn Ile Tyr Thr Asp Glu
            340                 345                 350

Ile Asn Ile Thr Pro Val Tyr Glu Thr Asn Asn Thr Tyr Pro Glu Val
        355                 360                 365

Ile Val Leu Asp Ala Asn Tyr Ile Asn Glu Lys Ile Asn Val Asn Ile
    370                 375                 380

Asn Asp Leu Ser Ile Arg Tyr Val Trp Ser Asn Asp Gly Asn Asp Phe
385                 390                 395                 400

Ile Leu Met Ser Thr Ser Glu Glu Asn Lys Val Ser Gln Val Lys Ile
                405                 410                 415

Arg Phe Val Asn Val Phe Lys Asp Lys Thr Leu Ala Asn Lys Leu Ser
            420                 425                 430

Phe Asn Phe Ser Asp Lys Gln Asp Val Pro Val Ser Glu Ile Ile Leu
        435                 440                 445

Ser Phe Thr Pro Ser Tyr Tyr Glu Asp Gly Leu Ile Gly Tyr Asp Leu
    450                 455                 460

Gly Leu Val Ser Leu Tyr Asn Glu Lys Phe Tyr Ile Asn Asn Phe Gly
465                 470                 475                 480

Met Met Val Ser Gly Leu Ile Tyr Ile Asn Asp Ser Leu Tyr Tyr Phe
                485                 490                 495

Lys Pro Pro Val Asn Asn Leu
                500

<210> SEQ ID NO 16
<211> LENGTH: 375
<212> TYPE: PRT
<213> ORGANISM: Artificial Sequence
<220> FEATURE:
<223> OTHER INFORMATION: Protein domain from amino acid residues 27-401
      of C. difficile CD2767

<400> SEQUENCE: 16

Ser Asn Asp Lys Glu Met Arg Ala Ala Trp Ile Ser Thr Val Tyr Asn
1               5                   10                  15
```

```
Leu Asp Trp Pro Lys Thr Lys Asn Asn Glu Ala Lys Gln Lys Lys Glu
            20                  25                  30

Tyr Thr Asp Leu Leu Asp Lys Leu Lys Ser Val Gly Ile Asn Thr Ala
                35                  40                  45

Val Val Gln Val Arg Pro Lys Ser Asp Ala Leu Tyr Lys Ser Asn Ile
 50                  55                  60

Asn Pro Trp Ser Glu Tyr Leu Thr Gly Thr Gln Gly Lys Asp Pro Gly
 65                  70                  75                  80

Tyr Asp Pro Leu Pro Phe Leu Ile Glu Glu Ala His Lys Arg Gly Met
                    85                  90                  95

Glu Phe His Ala Trp Phe Asn Pro Tyr Arg Ile Thr Met Ala Asp Glu
            100                 105                 110

Ser Ile Asp Lys Leu Pro Ala Asn His Pro Ala Lys Lys Asn Pro Ser
                115                 120                 125

Trp Val Val Lys His Gly Asn Lys Tyr Tyr Asp Pro Gly Leu Pro
            130                 135                 140

Glu Val Arg Lys Tyr Ile Val Asp Ser Ile Ala Glu Val Val Gln Asn
145                 150                 155                 160

Tyr Asp Ile Asp Gly Val His Phe Asp Asp Tyr Phe Pro Gly Val
                    165                 170                 175

Ser Phe Asn Asp Thr Ala Thr Tyr Gln Lys Tyr Gly Lys Gly Gln Asn
                180                 185                 190

Lys Asp Asp Trp Arg Arg Glu Asn Val Asn Thr Leu Leu Arg Asp Val
            195                 200                 205

Lys Ala Ser Ile Lys Ser Ile Lys Pro Asn Val Val Phe Gly Val Ser
            210                 215                 220

Pro Ala Gly Ile Trp Arg Asn Lys Ser Ser Asp Pro Thr Gly Ser Asp
225                 230                 235                 240

Thr Ser Gly Asn Glu Ser Tyr Val Gly Thr Tyr Ala Asp Thr Arg Ala
                245                 250                 255

Trp Ile Lys Gln Gly Leu Ile Asp Tyr Val Val Pro Gln Leu Tyr Trp
                260                 265                 270

Pro Ile Gly Leu Lys Ala Ala Asp Tyr Ser Lys Leu Val Ala Trp Trp
                275                 280                 285

Ala Asn Glu Val Lys Gly Thr Asn Val Asp Leu Tyr Ile Gly Gln Gly
290                 295                 300

Ile Tyr Lys Gln Gly Gln Ser Ser Tyr Gly Gly Gln Asn Ile Ala Lys
305                 310                 315                 320

Glu Ile Val Gln Gln Val Thr Leu Asn Arg Lys Tyr Ser Glu Ile Lys
                325                 330                 335

Gly Ser Met Tyr Phe Ser Ala Lys Asp Ile Ala Asn Ser Thr Ser Ile
                340                 345                 350

Gln Lys Asp Leu Lys Ser Leu Tyr Ser Ser Ser Glu Glu Pro Val Thr
                355                 360                 365

Pro Pro Ser Asn Val Lys Val
                370                 375

<210> SEQ ID NO 17
<211> LENGTH: 1711
<212> TYPE: PRT
<213> ORGANISM: Artificial Sequence
<220> FEATURE:
<223> OTHER INFORMATION: CD2767 (27-401) Toxin A (542-1850)-fusion
      protein in an expression construct
```

```
<400> SEQUENCE: 17

Met Gly Ser Ser His His His His His His Ser Ser Gly Leu Val Pro
 1               5                  10                  15

Arg Gly Ser His Met Ser Asn Asp Lys Glu Met Arg Ala Ala Trp Ile
             20                  25                  30

Ser Thr Val Tyr Asn Leu Asp Trp Pro Lys Thr Lys Asn Asn Glu Ala
         35                  40                  45

Lys Gln Lys Lys Glu Tyr Thr Asp Leu Leu Asp Lys Leu Lys Ser Val
     50                  55                  60

Gly Ile Asn Thr Ala Val Val Gln Val Arg Pro Lys Ser Asp Ala Leu
 65                  70                  75                  80

Tyr Lys Ser Asn Ile Asn Pro Trp Ser Glu Tyr Leu Thr Gly Thr Gln
             85                  90                  95

Gly Lys Asp Pro Gly Tyr Asp Pro Leu Pro Phe Leu Ile Glu Glu Ala
            100                 105                 110

His Lys Arg Gly Met Glu Phe His Ala Trp Phe Asn Pro Tyr Arg Ile
        115                 120                 125

Thr Met Ala Asp Glu Ser Ile Asp Lys Leu Pro Ala Asn His Pro Ala
    130                 135                 140

Lys Lys Asn Pro Ser Trp Val Val Lys His Gly Asn Lys Tyr Tyr Tyr
145                 150                 155                 160

Asp Pro Gly Leu Pro Glu Val Arg Lys Tyr Ile Val Asp Ser Ile Ala
                165                 170                 175

Glu Val Val Gln Asn Tyr Asp Ile Asp Gly Val His Phe Asp Asp Tyr
            180                 185                 190

Phe Tyr Pro Gly Val Ser Phe Asn Asp Thr Ala Thr Tyr Gln Lys Tyr
        195                 200                 205

Gly Lys Gly Gln Asn Lys Asp Asn Trp Arg Arg Glu Asn Val Asn Thr
    210                 215                 220

Leu Leu Arg Asp Val Lys Ala Ser Ile Lys Ser Ile Lys Pro Asn Val
225                 230                 235                 240

Val Phe Gly Val Ser Pro Ala Gly Ile Trp Arg Asn Lys Ser Ser Asp
                245                 250                 255

Pro Thr Gly Ser Asp Thr Ser Gly Asn Glu Ser Tyr Val Gly Thr Tyr
            260                 265                 270

Ala Asp Thr Arg Ala Trp Ile Lys Gln Gly Leu Ile Asp Tyr Val Val
        275                 280                 285

Pro Gln Leu Tyr Trp Pro Ile Gly Leu Lys Ala Ala Asp Tyr Ser Lys
    290                 295                 300

Leu Val Ala Trp Trp Ala Asn Glu Val Lys Gly Thr Asn Val Asp Leu
305                 310                 315                 320

Tyr Ile Gly Gln Gly Ile Tyr Lys Gln Gly Ser Ser Tyr Gly Gly
                325                 330                 335

Gln Asn Ile Ala Lys Glu Ile Val Gln Gln Val Thr Leu Asn Arg Lys
        340                 345                 350

Tyr Ser Glu Ile Lys Gly Ser Met Tyr Phe Ser Ala Lys Asp Ile Ala
    355                 360                 365

Asn Ser Thr Ser Ile Gln Lys Asp Leu Lys Ser Leu Tyr Ser Ser Ser
370                 375                 380

Glu Glu Pro Val Thr Pro Pro Ser Asn Val Lys Val Ala Ala Ala Pro
385                 390                 395                 400

Phe Thr Leu Ser Glu Asp Asn Gly Val Asp Phe Asn Lys Asn Thr Ala
                405                 410                 415
```

```
Leu Asp Lys Asn Tyr Leu Leu Asn Asn Lys Ile Pro Ser Asn Asn Val
            420                 425                 430

Glu Glu Ala Gly Ser Lys Asn Tyr Val His Tyr Ile Ile Gln Leu Gln
            435                 440                 445

Gly Asp Asp Ile Ser Tyr Glu Ala Thr Cys Asn Leu Phe Ser Lys Asn
            450                 455                 460

Pro Lys Asn Ser Ile Ile Ile Gln Arg Asn Met Asn Glu Ser Ala Lys
465                 470                 475                 480

Ser Tyr Phe Leu Ser Asp Gly Glu Ser Ile Leu Glu Leu Asn Lys
                485                 490                 495

Tyr Arg Ile Pro Glu Arg Leu Lys Asn Lys Glu Lys Val Lys Val Thr
                500                 505                 510

Phe Ile Gly His Gly Lys Asp Glu Phe Asn Thr Ser Glu Phe Ala Arg
            515                 520                 525

Leu Ser Val Asp Ser Leu Ser Asn Glu Ile Ser Ser Phe Leu Asp Thr
            530                 535                 540

Ile Lys Leu Asp Ile Ser Pro Lys Asn Val Glu Val Asn Leu Leu Gly
545                 550                 555                 560

Ser Asn Met Phe Ser Tyr Asp Phe Asn Val Glu Glu Thr Tyr Pro Gly
                565                 570                 575

Lys Leu Leu Ser Ile Met Asp Lys Ile Thr Ser Thr Leu Pro Asp
                580                 585                 590

Val Asn Lys Asn Ser Ile Thr Ile Gly Ala Asn Gln Tyr Glu Val Arg
            595                 600                 605

Ile Asn Ser Glu Gly Arg Lys Glu Leu Leu Ala His Ser Gly Lys Trp
            610                 615                 620

Ile Asn Lys Glu Glu Ala Ile Met Ser Asp Leu Ser Ser Lys Glu Tyr
625                 630                 635                 640

Ile Phe Phe Asp Ser Ile Asp Asn Lys Leu Lys Ala Lys Ser Lys Asn
                645                 650                 655

Ile Pro Gly Leu Ala Ser Ile Ser Glu Asp Ile Lys Thr Leu Leu Leu
                660                 665                 670

Asp Ala Ser Val Ser Pro Asp Thr Lys Phe Ile Leu Asn Asn Leu Lys
            675                 680                 685

Leu Asn Ile Glu Ser Ser Ile Gly Asp Tyr Ile Tyr Tyr Glu Lys Leu
            690                 695                 700

Glu Pro Val Lys Asn Ile Ile His Asn Ser Ile Asp Asp Leu Ile Asp
705                 710                 715                 720

Glu Phe Asn Leu Leu Glu Asn Val Ser Asp Glu Leu Tyr Glu Leu Lys
                725                 730                 735

Lys Leu Asn Asn Leu Asp Glu Lys Tyr Leu Ile Ser Phe Glu Asp Ile
            740                 745                 750

Ser Lys Asn Asn Ser Thr Tyr Ser Val Arg Phe Ile Asn Lys Ser Asn
            755                 760                 765

Gly Glu Ser Val Tyr Val Glu Thr Lys Glu Ile Phe Ser Lys Tyr
            770                 775                 780

Ser Glu His Ile Thr Lys Glu Ile Ser Thr Ile Lys Asn Ser Ile Ile
785                 790                 795                 800

Thr Asp Val Asn Gly Asn Leu Leu Asp Asn Ile Gln Leu Asp His Thr
                805                 810                 815

Ser Gln Val Asn Thr Leu Asn Ala Ala Phe Phe Ile Gln Ser Leu Ile
                820                 825                 830
```

```
Asp Tyr Ser Ser Asn Lys Asp Val Leu Asn Asp Leu Ser Thr Ser Val
        835                 840                 845

Lys Val Gln Leu Tyr Ala Gln Leu Phe Ser Thr Gly Leu Asn Thr Ile
850                 855                 860

Tyr Asp Ser Ile Gln Leu Val Asn Leu Ile Ser Asn Ala Val Asn Asp
865                 870                 875                 880

Thr Ile Asn Val Leu Pro Thr Ile Thr Glu Gly Ile Pro Ile Val Ser
                885                 890                 895

Thr Ile Leu Asp Gly Ile Asn Leu Gly Ala Ala Ile Lys Glu Leu Leu
            900                 905                 910

Asp Glu His Asp Pro Leu Leu Lys Lys Glu Leu Glu Ala Lys Val Gly
        915                 920                 925

Val Leu Ala Ile Asn Met Ser Leu Ser Ile Ala Ala Thr Val Ala Ser
930                 935                 940

Ile Val Gly Ile Gly Ala Glu Val Thr Ile Phe Leu Leu Pro Ile Ala
945                 950                 955                 960

Gly Ile Ser Ala Gly Ile Pro Ser Leu Val Asn Asn Glu Leu Ile Leu
                965                 970                 975

His Asp Lys Ala Thr Ser Val Val Asn Tyr Phe Asn His Leu Ser Glu
            980                 985                 990

Ser Lys Lys Tyr Gly Pro Leu Lys Thr Glu Asp Asp Lys Ile Leu Val
        995                 1000                1005

Pro Ile Asp Asp Leu Val Ile Ser Glu Ile Asp Phe Asn Asn Asn
    1010                1015                1020

Ser Ile Lys Leu Gly Thr Cys Asn Ile Leu Ala Met Glu Gly Gly
    1025                1030                1035

Ser Gly His Thr Val Thr Gly Asn Ile Asp His Phe Phe Ser Ser
    1040                1045                1050

Pro Ser Ile Ser Ser His Ile Pro Ser Leu Ser Ile Tyr Ser Ala
    1055                1060                1065

Ile Gly Ile Glu Thr Glu Asn Leu Asp Phe Ser Lys Lys Ile Met
    1070                1075                1080

Met Leu Pro Asn Ala Pro Ser Arg Val Phe Trp Trp Glu Thr Gly
    1085                1090                1095

Ala Val Pro Gly Leu Arg Ser Leu Glu Asn Asp Gly Thr Arg Leu
    1100                1105                1110

Leu Asp Ser Ile Arg Asp Leu Tyr Pro Gly Lys Phe Tyr Trp Arg
    1115                1120                1125

Phe Tyr Ala Phe Phe Asp Tyr Ala Ile Thr Thr Leu Lys Pro Val
    1130                1135                1140

Tyr Glu Asp Thr Asn Ile Lys Ile Lys Leu Asp Lys Asp Thr Arg
    1145                1150                1155

Asn Phe Ile Met Pro Thr Ile Thr Thr Asn Glu Ile Arg Asn Lys
    1160                1165                1170

Leu Ser Tyr Ser Phe Asp Gly Ala Gly Gly Thr Tyr Ser Leu Leu
    1175                1180                1185

Leu Ser Ser Tyr Pro Ile Ser Thr Asn Ile Asn Leu Ser Lys Asp
    1190                1195                1200

Asp Leu Trp Ile Phe Asn Ile Asp Asn Glu Val Arg Glu Ile Ser
    1205                1210                1215

Ile Glu Asn Gly Thr Ile Lys Lys Gly Lys Leu Ile Lys Asp Val
    1220                1225                1230

Leu Ser Lys Ile Asp Ile Asn Lys Asn Lys Leu Ile Ile Gly Asn
```

```
                1235                1240                1245

Gln Thr Ile Asp Phe Ser Gly Asp Ile Asp Asn Lys Asp Arg Tyr
        1250                1255                1260

Ile Phe Leu Thr Cys Glu Leu Asp Asp Lys Ile Ser Leu Ile Ile
        1265                1270                1275

Glu Ile Asn Leu Val Ala Lys Ser Tyr Ser Leu Leu Leu Ser Gly
        1280                1285                1290

Asp Lys Asn Tyr Leu Ile Ser Asn Leu Ser Asn Ile Ile Glu Lys
        1295                1300                1305

Ile Asn Thr Leu Gly Leu Asp Ser Lys Asn Ile Ala Tyr Asn Tyr
        1310                1315                1320

Thr Asp Glu Ser Asn Asn Lys Tyr Phe Gly Ala Ile Ser Lys Thr
        1325                1330                1335

Ser Gln Lys Ser Ile Ile His Tyr Lys Lys Asp Ser Lys Asn Ile
        1340                1345                1350

Leu Glu Phe Tyr Asn Asp Ser Thr Leu Glu Phe Asn Ser Lys Asp
        1355                1360                1365

Phe Ile Ala Glu Asp Ile Asn Val Phe Met Lys Asp Asp Ile Asn
        1370                1375                1380

Thr Ile Thr Gly Lys Tyr Tyr Val Asp Asn Asn Thr Asp Lys Ser
        1385                1390                1395

Ile Asp Phe Ser Ile Ser Leu Val Ser Lys Asn Gln Val Lys Val
        1400                1405                1410

Asn Gly Leu Tyr Leu Asn Glu Ser Val Tyr Ser Ser Tyr Leu Asp
        1415                1420                1425

Phe Val Lys Asn Ser Asp Gly His His Asn Thr Ser Asn Phe Met
        1430                1435                1440

Asn Leu Phe Leu Asp Asn Ile Ser Phe Trp Lys Leu Phe Gly Phe
        1445                1450                1455

Glu Asn Ile Asn Phe Val Ile Asp Lys Tyr Phe Thr Leu Val Gly
        1460                1465                1470

Lys Thr Asn Leu Gly Tyr Val Glu Phe Ile Cys Asp Asn Asn Lys
        1475                1480                1485

Asn Ile Asp Ile Tyr Phe Gly Glu Trp Lys Thr Ser Ser Ser Lys
        1490                1495                1500

Ser Thr Ile Phe Ser Gly Asn Gly Arg Asn Val Val Val Glu Pro
        1505                1510                1515

Ile Tyr Asn Pro Asp Thr Gly Glu Asp Ile Ser Thr Ser Leu Asp
        1520                1525                1530

Phe Ser Tyr Glu Pro Leu Tyr Gly Ile Asp Arg Tyr Ile Asn Lys
        1535                1540                1545

Val Leu Ile Ala Pro Asp Leu Tyr Thr Ser Leu Ile Asn Ile Asn
        1550                1555                1560

Thr Asn Tyr Tyr Ser Asn Glu Tyr Tyr Pro Glu Ile Ile Val Leu
        1565                1570                1575

Asn Pro Asn Thr Phe His Lys Lys Val Asn Ile Asn Leu Asp Ser
        1580                1585                1590

Ser Ser Phe Glu Tyr Lys Trp Ser Thr Glu Gly Ser Asp Phe Ile
        1595                1600                1605

Leu Val Arg Tyr Leu Glu Glu Ser Asn Lys Lys Ile Leu Gln Lys
        1610                1615                1620

Ile Arg Ile Lys Gly Ile Leu Ser Asn Thr Gln Ser Phe Asn Lys
        1625                1630                1635
```

-continued

Met Ser Ile Asp Phe Lys Asp Ile Lys Lys Leu Ser Leu Gly Tyr
1640                1645                1650

Ile Met Ser Asn Phe Lys Ser Phe Asn Ser Glu Asn Glu Leu Asp
    1655                1660                1665

Arg Asp His Leu Gly Phe Lys Ile Ile Asp Asn Lys Thr Tyr Tyr
    1670                1675                1680

Tyr Asp Glu Asp Ser Lys Leu Val Lys Gly Leu Ile Asn Ile Asn
    1685                1690                1695

Asn Ser Leu Phe Tyr Phe Asp Pro Ile Glu Phe Asn Leu
    1700                1705                1710

<210> SEQ ID NO 18
<211> LENGTH: 1461
<212> TYPE: PRT
<213> ORGANISM: Artificial Sequence
<220> FEATURE:
<223> OTHER INFORMATION: CD2767 (27-401) Toxin 6 (767-1852)-fusion
      protein in an expression construct

<400> SEQUENCE: 18

Ser Asn Asp Lys Glu Met Arg Ala Ala Trp Ile Ser Thr Val Tyr Asn
1               5                   10                  15

Leu Asp Trp Pro Lys Thr Lys Asn Asn Glu Ala Lys Gln Lys Lys Glu
            20                  25                  30

Tyr Thr Asp Leu Leu Asp Lys Leu Lys Ser Val Gly Ile Asn Thr Ala
        35                  40                  45

Val Val Gln Val Arg Pro Lys Ser Asp Ala Leu Tyr Lys Ser Asn Ile
50                  55                  60

Asn Pro Trp Ser Glu Tyr Leu Thr Gly Thr Gln Gly Lys Asp Pro Gly
65                  70                  75                  80

Tyr Asp Pro Leu Pro Phe Leu Ile Glu Glu Ala His Lys Arg Gly Met
                85                  90                  95

Glu Phe His Ala Trp Phe Asn Pro Tyr Arg Ile Thr Met Ala Asp Glu
            100                 105                 110

Ser Ile Asp Lys Leu Pro Ala Asn His Pro Ala Lys Lys Asn Pro Ser
        115                 120                 125

Trp Val Val Lys His Gly Asn Lys Tyr Tyr Asp Pro Gly Leu Pro
    130                 135                 140

Glu Val Arg Lys Tyr Ile Val Asp Ser Ile Ala Glu Val Val Gln Asn
145                 150                 155                 160

Tyr Asp Ile Asp Gly Val His Phe Asp Asp Tyr Phe Tyr Pro Gly Val
                165                 170                 175

Ser Phe Asn Asp Thr Ala Thr Tyr Gln Lys Tyr Gly Lys Gly Gln Asn
            180                 185                 190

Lys Asp Asp Trp Arg Arg Glu Asn Val Asn Thr Leu Leu Arg Asp Val
        195                 200                 205

Lys Ala Ser Ile Lys Ser Ile Lys Pro Asn Val Val Phe Gly Val Ser
    210                 215                 220

Pro Ala Gly Ile Trp Arg Asn Lys Ser Ser Pro Thr Gly Ser Asp
225                 230                 235                 240

Thr Ser Gly Asn Glu Ser Tyr Val Gly Thr Tyr Ala Asp Thr Arg Ala
                245                 250                 255

Trp Ile Lys Gln Gly Leu Ile Asp Tyr Val Val Pro Gln Leu Tyr Trp
            260                 265                 270

Pro Ile Gly Leu Lys Ala Ala Asp Tyr Ser Lys Leu Val Ala Trp Trp

```
            275                 280                 285
Ala Asn Glu Val Lys Gly Thr Asn Val Asp Leu Tyr Ile Gly Gln Gly
290                 295                 300

Ile Tyr Lys Gln Gly Gln Ser Ser Tyr Gly Gly Gln Asn Ile Ala Lys
305                 310                 315                 320

Glu Ile Val Gln Gln Val Thr Leu Asn Arg Lys Tyr Ser Glu Ile Lys
                325                 330                 335

Gly Ser Met Tyr Phe Ser Ala Lys Asp Ile Ala Asn Ser Thr Ser Ile
                340                 345                 350

Gln Lys Asp Leu Lys Ser Leu Tyr Ser Ser Glu Glu Pro Val Thr
            355                 360                 365

Pro Pro Ser Asn Val Lys Val Ser Ile Ile Lys Asp Ile Ser Ser Lys
370                 375                 380

Glu Tyr Ile Ser Phe Asn Pro Lys Glu Asn Lys Ile Thr Val Lys Ser
385                 390                 395                 400

Lys Asn Leu Pro Glu Leu Ser Thr Leu Leu Gln Glu Ile Arg Asn Asn
                405                 410                 415

Ser Asn Ser Ser Asp Ile Glu Leu Glu Glu Lys Val Met Leu Thr Glu
            420                 425                 430

Cys Glu Ile Asn Val Ile Ser Asn Ile Asp Thr Gln Ile Val Glu Glu
            435                 440                 445

Arg Ile Glu Glu Ala Lys Asn Leu Thr Ser Asp Ser Ile Asn Tyr Ile
450                 455                 460

Lys Asp Glu Phe Lys Leu Ile Glu Ser Ile Ser Asp Ala Leu Cys Asp
465                 470                 475                 480

Leu Lys Gln Gln Asn Glu Leu Glu Asp Ser His Phe Ile Ser Phe Glu
                485                 490                 495

Asp Ile Ser Glu Thr Asp Glu Gly Phe Ser Ile Arg Phe Ile Asn Lys
            500                 505                 510

Glu Thr Gly Glu Ser Ile Phe Val Gly Thr Glu Lys Thr Ile Phe Ser
            515                 520                 525

Glu Tyr Ala Asn His Ile Thr Glu Glu Ile Ser Lys Ile Lys Gly Thr
530                 535                 540

Ile Phe Asp Thr Val Asn Gly Lys Leu Val Lys Lys Val Asn Leu Asp
545                 550                 555                 560

Thr Thr His Glu Val Asn Thr Leu Asn Ala Ala Phe Phe Ile Gln Ser
                565                 570                 575

Leu Ile Glu Tyr Asn Ser Ser Lys Glu Ser Leu Ser Asn Leu Ser Val
            580                 585                 590

Ala Met Lys Val Gln Val Tyr Ala Gln Leu Phe Ser Thr Gly Leu Asn
            595                 600                 605

Thr Ile Thr Asp Ala Ala Lys Val Val Glu Leu Val Ser Thr Ala Leu
610                 615                 620

Asp Glu Thr Ile Asp Leu Leu Pro Thr Leu Ser Glu Gly Leu Pro Ile
625                 630                 635                 640

Ile Ala Thr Ile Ile Asp Gly Val Ser Leu Gly Ala Ala Ile Lys Glu
                645                 650                 655

Leu Ser Glu Thr Ser Asp Pro Leu Leu Arg Gln Glu Ile Glu Ala Lys
            660                 665                 670

Ile Gly Ile Met Ala Val Asn Leu Thr Thr Ala Thr Thr Ala Ile Ile
            675                 680                 685

Thr Ser Ser Leu Gly Ile Ala Ser Gly Phe Ser Ile Leu Leu Val Pro
            690                 695                 700
```

```
Leu Ala Gly Ile Ser Ala Gly Ile Pro Ser Leu Val Asn Asn Glu Leu
705                 710                 715                 720

Val Leu Arg Asp Lys Ala Thr Lys Val Val Asp Tyr Phe Lys His Val
                725                 730                 735

Ser Leu Val Glu Thr Glu Gly Val Phe Thr Leu Leu Asp Lys Ile
            740                 745                 750

Met Met Pro Gln Asp Asp Leu Val Ile Ser Glu Ile Asp Phe Asn Asn
                755                 760                 765

Asn Ser Ile Val Leu Gly Lys Cys Glu Ile Trp Arg Met Glu Gly Gly
770                 775                 780

Ser Gly His Thr Val Thr Asp Asp Ile Asp His Phe Ser Ala Pro
785                 790                 795                 800

Ser Ile Thr Tyr Arg Glu Pro His Leu Ser Ile Tyr Asp Val Leu Glu
                805                 810                 815

Val Gln Lys Glu Glu Leu Asp Leu Ser Lys Asp Leu Met Val Leu Pro
            820                 825                 830

Asn Ala Pro Asn Arg Val Phe Ala Trp Glu Thr Gly Trp Thr Pro Gly
            835                 840                 845

Leu Arg Ser Leu Glu Asn Asp Gly Thr Lys Leu Leu Asp Arg Ile Arg
    850                 855                 860

Asp Asn Tyr Glu Gly Glu Phe Tyr Trp Arg Tyr Phe Ala Phe Ile Ala
865                 870                 875                 880

Asp Ala Leu Ile Thr Thr Leu Lys Pro Arg Tyr Glu Asp Thr Asn Ile
                885                 890                 895

Arg Ile Asn Leu Asp Ser Asn Thr Arg Ser Phe Ile Val Pro Ile Ile
                900                 905                 910

Thr Thr Glu Tyr Ile Arg Glu Lys Leu Ser Tyr Ser Phe Tyr Gly Ser
            915                 920                 925

Gly Gly Thr Tyr Ala Leu Ser Leu Ser Gln Tyr Asn Met Gly Ile Asn
    930                 935                 940

Ile Glu Leu Ser Glu Ser Asp Val Trp Ile Ile Asp Val Asp Asn Val
945                 950                 955                 960

Val Arg Asp Val Thr Ile Glu Ser Asp Lys Ile Lys Lys Gly Asp Leu
                965                 970                 975

Ile Glu Gly Ile Leu Ser Thr Leu Ser Ile Glu Glu Asn Lys Ile Ile
            980                 985                 990

Leu Asn Ser His Glu Ile Asn Phe Ser Gly Glu Val Asn Gly Ser Asn
        995                 1000                1005

Gly Phe Val Ser Leu Thr Phe Ser Ile Leu Glu Gly Ile Asn Ala
    1010                1015                1020

Ile Ile Glu Val Asp Leu Leu Ser Lys Ser Tyr Lys Leu Leu Ile
    1025                1030                1035

Ser Gly Glu Leu Lys Ile Leu Met Leu Asn Ser Asn His Ile Gln
    1040                1045                1050

Gln Lys Ile Asp Tyr Ile Gly Phe Asn Ser Glu Leu Gln Lys Asn
    1055                1060                1065

Ile Pro Tyr Ser Phe Val Asp Ser Glu Gly Lys Glu Asn Gly Phe
    1070                1075                1080

Ile Asn Gly Ser Thr Lys Glu Gly Leu Phe Val Ser Glu Leu Pro
    1085                1090                1095

Asp Val Val Leu Ile Ser Lys Val Tyr Met Asp Asp Ser Lys Pro
    1100                1105                1110
```

```
Ser Phe Gly Tyr Tyr Ser Asn Asn Leu Lys Asp Val Lys Val Ile
1115                1120                1125

Thr Lys Asp Asn Val Asn Ile Leu Thr Gly Tyr Tyr Leu Lys Asp
1130                1135                1140

Asp Ile Lys Ile Ser Leu Ser Leu Thr Leu Gln Asp Glu Lys Thr
1145                1150                1155

Ile Lys Leu Asn Ser Val His Leu Asp Glu Ser Gly Val Ala Glu
1160                1165                1170

Ile Leu Lys Phe Met Asn Arg Lys Gly Asn Thr Asn Thr Ser Asp
1175                1180                1185

Ser Leu Met Ser Phe Leu Glu Ser Met Asn Ile Lys Ser Ile Phe
1190                1195                1200

Val Asn Phe Leu Gln Ser Asn Ile Lys Phe Ile Leu Asp Ala Asn
1205                1210                1215

Phe Ile Ile Ser Gly Thr Thr Ser Ile Gly Gln Phe Glu Phe Ile
1220                1225                1230

Cys Asp Glu Asn Asp Asn Ile Gln Pro Tyr Phe Ile Lys Phe Asn
1235                1240                1245

Thr Leu Glu Thr Asn Tyr Thr Leu Tyr Val Gly Asn Arg Gln Asn
1250                1255                1260

Met Ile Val Glu Pro Asn Tyr Asp Leu Asp Asp Ser Gly Asp Ile
1265                1270                1275

Ser Ser Thr Val Ile Asn Phe Ser Gln Lys Tyr Leu Tyr Gly Ile
1280                1285                1290

Asp Ser Cys Val Asn Lys Val Val Ile Ser Pro Asn Ile Tyr Thr
1295                1300                1305

Asp Glu Ile Asn Ile Thr Pro Val Tyr Glu Thr Asn Asn Thr Tyr
1310                1315                1320

Pro Glu Val Ile Val Leu Asp Ala Asn Tyr Ile Asn Glu Lys Ile
1325                1330                1335

Asn Val Asn Ile Asn Asp Leu Ser Ile Arg Tyr Val Trp Ser Asn
1340                1345                1350

Asp Gly Asn Asp Phe Ile Leu Met Ser Thr Ser Glu Glu Asn Lys
1355                1360                1365

Val Ser Gln Val Lys Ile Arg Phe Val Asn Val Phe Lys Asp Lys
1370                1375                1380

Thr Leu Ala Asn Lys Leu Ser Phe Asn Phe Ser Asp Lys Gln Asp
1385                1390                1395

Val Pro Val Ser Glu Ile Ile Leu Ser Phe Thr Pro Ser Tyr Tyr
1400                1405                1410

Glu Asp Gly Leu Ile Gly Tyr Asp Leu Gly Leu Val Ser Leu Tyr
1415                1420                1425

Asn Glu Lys Phe Tyr Ile Asn Asn Phe Gly Met Met Val Ser Gly
1430                1435                1440

Leu Ile Tyr Ile Asn Asp Ser Leu Tyr Tyr Phe Lys Pro Pro Val
1445                1450                1455

Asn Asn Leu
1460

<210> SEQ ID NO 19
<211> LENGTH: 1455
<212> TYPE: PRT
<213> ORGANISM: Artificial Sequence
<220> FEATURE:
<223> OTHER INFORMATION: Toxin A (residues 542 -1850; TxACPD) within the
``` construct: 6His-Thioredoxin-TxACPD

<400> SEQUENCE: 19

```
Met Gly Ser Ser His His His His His His Ser His Met Ala Ser Asp
1               5                   10                  15

Lys Ile Ile His Leu Thr Asp Asp Ser Phe Asp Thr Asp Val Leu Lys
            20                  25                  30

Ala Asp Gly Ala Ile Leu Val Asp Phe Trp Ala Glu Trp Cys Gly Pro
        35                  40                  45

Cys Lys Met Ile Ala Pro Ile Leu Asp Glu Ile Ala Asp Glu Tyr Gln
    50                  55                  60

Gly Lys Leu Thr Val Ala Lys Leu Asn Ile Asp Gln Asn Pro Gly Thr
65                  70                  75                  80

Ala Pro Lys Tyr Gly Ile Arg Gly Ile Pro Thr Leu Leu Leu Phe Lys
                85                  90                  95

Asn Gly Glu Val Ala Ala Thr Lys Val Gly Ala Leu Ser Lys Gly Gln
            100                 105                 110

Leu Lys Glu Phe Leu Asp Ala Asn Leu Ala Arg Ala Leu Val Pro Arg
        115                 120                 125

Gly Ser Val Thr Ser Leu Tyr Lys Lys Ala Gly Ser Ala Ala Ala Pro
130                 135                 140

Phe Thr Leu Ser Glu Asp Asn Gly Val Asp Phe Asn Lys Asn Thr Ala
145                 150                 155                 160

Leu Asp Lys Asn Tyr Leu Leu Asn Asn Lys Ile Pro Ser Asn Asn Val
                165                 170                 175

Glu Glu Ala Gly Ser Lys Asn Tyr Val His Tyr Ile Ile Gln Leu Gln
            180                 185                 190

Gly Asp Asp Ile Ser Tyr Glu Ala Thr Cys Asn Leu Phe Ser Lys Asn
        195                 200                 205

Pro Lys Asn Ser Ile Ile Ile Gln Arg Asn Met Asn Glu Ser Ala Lys
    210                 215                 220

Ser Tyr Phe Leu Ser Asp Asp Gly Glu Ser Ile Leu Glu Leu Asn Lys
225                 230                 235                 240

Tyr Arg Ile Pro Glu Arg Leu Lys Asn Lys Glu Lys Val Lys Val Thr
                245                 250                 255

Phe Ile Gly His Gly Lys Asp Glu Phe Asn Thr Ser Glu Phe Ala Arg
            260                 265                 270

Leu Ser Val Asp Ser Leu Ser Asn Glu Ile Ser Ser Phe Leu Asp Thr
        275                 280                 285

Ile Lys Leu Asp Ile Ser Pro Lys Asn Val Glu Val Asn Leu Leu Gly
    290                 295                 300

Ser Asn Met Phe Ser Tyr Asp Phe Asn Val Glu Glu Thr Tyr Pro Gly
305                 310                 315                 320

Lys Leu Leu Leu Ser Ile Met Asp Lys Ile Thr Ser Thr Leu Pro Asp
                325                 330                 335

Val Asn Lys Asn Ser Ile Thr Ile Gly Ala Asn Gln Tyr Glu Val Arg
            340                 345                 350

Ile Asn Ser Glu Gly Arg Lys Glu Leu Leu Ala His Ser Gly Lys Trp
        355                 360                 365

Ile Asn Lys Glu Glu Ala Ile Met Ser Asp Leu Ser Ser Lys Glu Tyr
    370                 375                 380

Ile Phe Phe Asp Ser Ile Asp Asn Lys Leu Lys Ala Lys Ser Lys Asn
385                 390                 395                 400
```

-continued

```
Ile Pro Gly Leu Ala Ser Ile Ser Glu Asp Ile Lys Thr Leu Leu Leu
                405                 410                 415
Asp Ala Ser Val Ser Pro Asp Thr Lys Phe Ile Leu Asn Asn Leu Lys
            420                 425                 430
Leu Asn Ile Glu Ser Ser Ile Gly Asp Tyr Ile Tyr Tyr Glu Lys Leu
        435                 440                 445
Glu Pro Val Lys Asn Ile Ile His Asn Ser Ile Asp Asp Leu Ile Asp
    450                 455                 460
Glu Phe Asn Leu Leu Glu Asn Val Ser Asp Glu Leu Tyr Glu Leu Lys
465                 470                 475                 480
Lys Leu Asn Asn Leu Asp Glu Lys Tyr Leu Ile Ser Phe Glu Asp Ile
                485                 490                 495
Ser Lys Asn Asn Ser Thr Tyr Ser Val Arg Phe Ile Asn Lys Ser Asn
            500                 505                 510
Gly Glu Ser Val Tyr Val Glu Thr Glu Lys Glu Ile Phe Ser Lys Tyr
        515                 520                 525
Ser Glu His Ile Thr Lys Glu Ile Ser Thr Ile Lys Asn Ser Ile Ile
    530                 535                 540
Thr Asp Val Asn Gly Asn Leu Leu Asp Asn Ile Gln Leu Asp His Thr
545                 550                 555                 560
Ser Gln Val Asn Thr Leu Asn Ala Ala Phe Phe Ile Gln Ser Leu Ile
                565                 570                 575
Asp Tyr Ser Ser Asn Lys Asp Val Leu Asn Asp Leu Ser Thr Ser Val
            580                 585                 590
Lys Val Gln Leu Tyr Ala Gln Leu Phe Ser Thr Gly Leu Asn Thr Ile
        595                 600                 605
Tyr Asp Ser Ile Gln Leu Val Asn Leu Ile Ser Asn Ala Val Asn Asp
    610                 615                 620
Thr Ile Asn Val Leu Pro Thr Ile Thr Glu Gly Ile Pro Ile Val Ser
625                 630                 635                 640
Thr Ile Leu Asp Gly Ile Asn Leu Gly Ala Ala Ile Lys Glu Leu Leu
                645                 650                 655
Asp Glu His Asp Pro Leu Leu Lys Lys Glu Leu Glu Ala Lys Val Gly
            660                 665                 670
Val Leu Ala Ile Asn Met Ser Leu Ser Ile Ala Ala Thr Val Ala Ser
        675                 680                 685
Ile Val Gly Ile Gly Ala Glu Val Thr Ile Phe Leu Leu Pro Ile Ala
    690                 695                 700
Gly Ile Ser Ala Gly Ile Pro Ser Leu Val Asn Asn Glu Leu Ile Leu
705                 710                 715                 720
His Asp Lys Ala Thr Ser Val Val Asn Tyr Phe Asn His Leu Ser Glu
                725                 730                 735
Ser Lys Lys Tyr Gly Pro Leu Lys Thr Glu Asp Asp Lys Ile Leu Val
            740                 745                 750
Pro Ile Asp Asp Leu Val Ile Ser Glu Ile Asp Phe Asn Asn Asn Ser
        755                 760                 765
Ile Lys Leu Gly Thr Cys Asn Ile Leu Ala Met Glu Gly Gly Ser Gly
    770                 775                 780
His Thr Val Thr Gly Asn Ile Asp His Phe Phe Ser Ser Pro Ser Ile
785                 790                 795                 800
Ser Ser His Ile Pro Ser Leu Ser Ile Tyr Ser Ala Ile Gly Ile Glu
                805                 810                 815
Thr Glu Asn Leu Asp Phe Ser Lys Lys Ile Met Met Leu Pro Asn Ala
```

```
                820                 825                 830
Pro Ser Arg Val Phe Trp Trp Glu Thr Gly Ala Val Pro Gly Leu Arg
                    835                 840                 845
Ser Leu Glu Asn Asp Gly Thr Arg Leu Leu Asp Ser Ile Arg Asp Leu
850                 855                 860
Tyr Pro Gly Lys Phe Tyr Trp Arg Phe Tyr Ala Phe Phe Asp Tyr Ala
865                 870                 875                 880
Ile Thr Thr Leu Lys Pro Val Tyr Glu Asp Thr Asn Ile Lys Ile Lys
                    885                 890                 895
Leu Asp Lys Asp Thr Arg Asn Phe Ile Met Pro Thr Ile Thr Thr Asn
                900                 905                 910
Glu Ile Arg Asn Lys Leu Ser Tyr Ser Phe Asp Gly Ala Gly Gly Thr
                915                 920                 925
Tyr Ser Leu Leu Leu Ser Ser Tyr Pro Ile Ser Thr Asn Ile Asn Leu
930                 935                 940
Ser Lys Asp Asp Leu Trp Ile Phe Asn Ile Asp Asn Glu Val Arg Glu
945                 950                 955                 960
Ile Ser Ile Glu Asn Gly Thr Ile Lys Lys Gly Lys Leu Ile Lys Asp
                965                 970                 975
Val Leu Ser Lys Ile Asp Ile Asn Lys Asn Lys Leu Ile Ile Gly Asn
                    980                 985                 990
Gln Thr Ile Asp Phe Ser Gly Asp Ile Asp Asn Lys Asp Arg Tyr Ile
                995                 1000                1005
Phe Leu Thr Cys Glu Leu Asp Asp Lys Ile Ser Leu Ile Ile Glu
        1010                1015                1020
Ile Asn Leu Val Ala Lys Ser Tyr Ser Leu Leu Leu Ser Gly Asp
        1025                1030                1035
Lys Asn Tyr Leu Ile Ser Asn Leu Ser Asn Ile Ile Glu Lys Ile
        1040                1045                1050
Asn Thr Leu Gly Leu Asp Ser Lys Asn Ile Ala Tyr Asn Tyr Thr
        1055                1060                1065
Asp Glu Ser Asn Asn Lys Tyr Phe Gly Ala Ile Ser Lys Thr Ser
        1070                1075                1080
Gln Lys Ser Ile Ile His Tyr Lys Lys Asp Ser Lys Asn Ile Leu
        1085                1090                1095
Glu Phe Tyr Asn Asp Ser Thr Leu Glu Phe Asn Ser Lys Asp Phe
        1100                1105                1110
Ile Ala Glu Asp Ile Asn Val Phe Met Lys Asp Asp Ile Asn Thr
        1115                1120                1125
Ile Thr Gly Lys Tyr Tyr Val Asp Asn Asn Thr Asp Lys Ser Ile
        1130                1135                1140
Asp Phe Ser Ile Ser Leu Val Ser Lys Asn Gln Val Lys Val Asn
        1145                1150                1155
Gly Leu Tyr Leu Asn Glu Ser Val Tyr Ser Ser Tyr Leu Asp Phe
        1160                1165                1170
Val Lys Asn Ser Asp Gly His His Asn Thr Ser Asn Phe Met Asn
        1175                1180                1185
Leu Phe Leu Asp Asn Ile Ser Phe Trp Lys Leu Phe Gly Phe Glu
        1190                1195                1200
Asn Ile Asn Phe Val Ile Asp Lys Tyr Phe Thr Leu Val Gly Lys
        1205                1210                1215
Thr Asn Leu Gly Tyr Val Glu Phe Ile Cys Asp Asn Asn Lys Asn
        1220                1225                1230
```

```
Ile Asp  Ile Tyr Phe Gly Glu  Trp Lys Thr Ser Ser  Ser Lys Ser
    1235                 1240                 1245

Thr Ile  Phe Ser Gly Asn Gly  Arg Asn Val Val Val  Glu Pro Ile
    1250                 1255                 1260

Tyr Asn  Pro Asp Thr Gly Glu  Asp Ile Ser Thr Ser  Leu Asp Phe
    1265                 1270                 1275

Ser Tyr  Glu Pro Leu Tyr Gly  Ile Asp Arg Tyr Ile  Asn Lys Val
    1280                 1285                 1290

Leu Ile  Ala Pro Asp Leu Tyr  Thr Ser Leu Ile Asn  Ile Asn Thr
    1295                 1300                 1305

Asn Tyr  Tyr Ser Asn Glu Tyr  Tyr Pro Glu Ile Ile  Val Leu Asn
    1310                 1315                 1320

Pro Asn  Thr Phe His Lys Lys  Val Asn Ile Asn Leu  Asp Ser Ser
    1325                 1330                 1335

Ser Phe  Glu Tyr Lys Trp Ser  Thr Glu Gly Ser Asp  Phe Ile Leu
    1340                 1345                 1350

Val Arg  Tyr Leu Glu Glu Ser  Asn Lys Lys Ile Leu  Gln Lys Ile
    1355                 1360                 1365

Arg Ile  Lys Gly Ile Leu Ser  Asn Thr Gln Ser Phe  Asn Lys Met
    1370                 1375                 1380

Ser Ile  Asp Phe Lys Asp Ile  Lys Lys Leu Ser Leu  Gly Tyr Ile
    1385                 1390                 1395

Met Ser  Asn Phe Lys Ser Phe  Asn Ser Glu Asn Glu  Leu Asp Arg
    1400                 1405                 1410

Asp His  Leu Gly Phe Lys Ile  Ile Asp Asn Lys Thr  Tyr Tyr Tyr
    1415                 1420                 1425

Asp Glu  Asp Ser Lys Leu Val  Lys Gly Leu Ile Asn  Ile Asn Asn
    1430                 1435                 1440

Ser Leu  Phe Tyr Phe Asp Pro  Ile Glu Phe Asn Leu
    1445                 1450                 1455
```

<210> SEQ ID NO 20
<211> LENGTH: 1256
<212> TYPE: PRT
<213> ORGANISM: Artificial Sequence
<220> FEATURE:
<223> OTHER INFORMATION: Toxin B (residues 767 -1852; TxBc) within the construct: 6His-Thioredoxin-TxBc

<400> SEQUENCE: 20

```
Met Gly Ser Ser His His His His His His Ser His Met Ala Ser Asp
1               5                   10                  15

Lys Ile Ile His Leu Thr Asp Asp Ser Phe Asp Thr Asp Val Leu Lys
            20                  25                  30

Ala Asp Gly Ala Ile Leu Val Asp Phe Trp Ala Glu Trp Cys Gly Pro
        35                  40                  45

Cys Lys Met Ile Ala Pro Ile Leu Asp Glu Ile Ala Asp Glu Tyr Gln
    50                  55                  60

Gly Lys Leu Thr Val Ala Lys Leu Asn Ile Asp Gln Asn Pro Gly Thr
65                  70                  75                  80

Ala Pro Lys Tyr Gly Ile Arg Gly Ile Pro Thr Leu Leu Leu Phe Lys
                85                  90                  95

Asn Gly Glu Val Ala Ala Thr Lys Val Gly Ala Leu Ser Lys Gly Gln
            100                 105                 110

Leu Lys Glu Phe Leu Asp Ala Asn Leu Ala Arg Ala Leu Val Pro Arg

```
            115                 120                 125
Gly Ser Val Thr Ser Leu Tyr Lys Lys Ala Gly Ser Ala Ala Ala Pro
    130                 135                 140

Phe Thr Ser Ile Ile Lys Asp Ile Ser Ser Lys Glu Tyr Ile Ser Phe
145                 150                 155                 160

Asn Pro Lys Glu Asn Lys Ile Thr Val Lys Ser Lys Asn Leu Pro Glu
                165                 170                 175

Leu Ser Thr Leu Leu Gln Glu Ile Arg Asn Asn Ser Asn Ser Ser Asp
            180                 185                 190

Ile Glu Leu Glu Glu Lys Val Met Leu Thr Glu Cys Glu Ile Asn Val
        195                 200                 205

Ile Ser Asn Ile Asp Thr Gln Ile Val Glu Glu Arg Ile Glu Glu Ala
        210                 215                 220

Lys Asn Leu Thr Ser Asp Ser Ile Asn Tyr Ile Lys Asp Glu Phe Lys
225                 230                 235                 240

Leu Ile Glu Ser Ile Ser Asp Ala Leu Cys Asp Leu Lys Gln Gln Asn
                245                 250                 255

Glu Leu Glu Asp Ser His Phe Ile Ser Phe Glu Asp Ile Ser Glu Thr
            260                 265                 270

Asp Glu Gly Phe Ser Ile Arg Phe Ile Asn Lys Glu Thr Gly Glu Ser
        275                 280                 285

Ile Phe Val Glu Thr Glu Lys Thr Ile Phe Ser Glu Tyr Ala Asn His
        290                 295                 300

Ile Thr Glu Glu Ile Ser Lys Ile Lys Gly Thr Ile Phe Asp Thr Val
305                 310                 315                 320

Asn Gly Lys Leu Val Lys Lys Val Asn Leu Asp Thr Thr His Glu Val
                325                 330                 335

Asn Thr Leu Asn Ala Ala Phe Phe Ile Gln Ser Leu Ile Glu Tyr Asn
            340                 345                 350

Ser Ser Lys Glu Ser Leu Ser Asn Leu Ser Val Ala Met Lys Val Gln
        355                 360                 365

Val Tyr Ala Gln Leu Phe Ser Thr Gly Leu Asn Thr Ile Thr Asp Ala
        370                 375                 380

Ala Lys Val Val Glu Leu Val Ser Thr Ala Leu Asp Glu Thr Ile Asp
385                 390                 395                 400

Leu Leu Pro Thr Leu Ser Glu Gly Leu Pro Ile Ile Ala Thr Ile Ile
                405                 410                 415

Asp Gly Val Ser Leu Gly Ala Ala Ile Lys Glu Leu Ser Glu Thr Ser
            420                 425                 430

Asp Pro Leu Leu Arg Gln Glu Ile Glu Ala Lys Ile Gly Ile Met Ala
        435                 440                 445

Val Asn Leu Thr Thr Ala Thr Thr Ala Ile Ile Thr Ser Ser Leu Gly
        450                 455                 460

Ile Ala Ser Gly Phe Ser Ile Leu Leu Val Pro Leu Ala Gly Ile Ser
465                 470                 475                 480

Ala Gly Ile Pro Ser Leu Val Asn Asn Glu Leu Val Leu Arg Asp Lys
                485                 490                 495

Ala Thr Lys Val Val Asp Tyr Phe Lys His Val Ser Leu Val Glu Thr
            500                 505                 510

Glu Gly Val Phe Thr Leu Leu Asp Asp Lys Ile Met Met Pro Gln Asp
        515                 520                 525

Asp Leu Val Ile Ser Glu Ile Asp Phe Asn Asn Asn Ser Ile Val Leu
        530                 535                 540
```

```
Gly Lys Cys Glu Ile Trp Arg Met Glu Gly Ser Gly His Thr Val
545                 550                 555                 560

Thr Asp Asp Ile Asp His Phe Phe Ser Ala Pro Ser Ile Thr Tyr Arg
                565                 570                 575

Glu Pro His Leu Ser Ile Tyr Asp Val Leu Glu Val Gln Lys Glu Glu
            580                 585                 590

Leu Asp Leu Ser Lys Asp Leu Met Val Leu Pro Asn Ala Pro Asn Arg
            595                 600                 605

Val Phe Ala Trp Glu Thr Gly Trp Thr Pro Gly Leu Arg Ser Leu Glu
610                 615                 620

Asn Asp Gly Thr Lys Leu Leu Asp Arg Ile Arg Asp Asn Tyr Glu Gly
625                 630                 635                 640

Glu Phe Tyr Trp Arg Tyr Phe Ala Phe Ile Ala Asp Ala Leu Ile Thr
                645                 650                 655

Thr Leu Lys Pro Arg Tyr Glu Asp Thr Asn Ile Arg Ile Asn Leu Asp
            660                 665                 670

Ser Asn Thr Arg Ser Phe Ile Val Pro Ile Ile Thr Thr Glu Tyr Ile
            675                 680                 685

Arg Glu Lys Leu Ser Tyr Ser Phe Tyr Gly Ser Gly Thr Tyr Ala
            690                 695                 700

Leu Ser Leu Ser Gln Tyr Asn Met Gly Ile Asn Ile Glu Leu Ser Glu
705                 710                 715                 720

Ser Asp Val Trp Ile Ile Asp Val Asp Asn Val Val Arg Asp Val Thr
                725                 730                 735

Ile Glu Ser Asp Lys Ile Lys Lys Gly Asp Leu Ile Glu Gly Ile Leu
            740                 745                 750

Ser Thr Leu Ser Ile Glu Glu Asn Lys Ile Ile Leu Asn Ser His Glu
            755                 760                 765

Ile Asn Phe Ser Gly Glu Val Asn Gly Ser Asn Gly Phe Val Ser Leu
770                 775                 780

Thr Phe Ser Ile Leu Glu Gly Ile Asn Ala Ile Ile Glu Val Asp Leu
785                 790                 795                 800

Leu Ser Lys Ser Tyr Lys Leu Leu Ile Ser Gly Glu Leu Lys Ile Leu
                805                 810                 815

Met Leu Asn Ser Asn His Ile Gln Gln Lys Ile Asp Tyr Ile Gly Phe
            820                 825                 830

Asn Ser Glu Leu Gln Lys Asn Ile Pro Tyr Ser Phe Val Asp Ser Glu
            835                 840                 845

Gly Lys Glu Asn Gly Phe Ile Asn Gly Ser Thr Lys Glu Gly Leu Phe
850                 855                 860

Val Ser Glu Leu Pro Asp Val Val Leu Ile Ser Lys Val Tyr Met Asp
865                 870                 875                 880

Asp Ser Lys Pro Ser Phe Gly Tyr Tyr Ser Asn Asn Leu Lys Asp Val
                885                 890                 895

Lys Val Ile Thr Lys Asp Asn Val Asn Ile Leu Thr Gly Tyr Tyr Leu
            900                 905                 910

Lys Asp Asp Ile Lys Ile Ser Leu Ser Leu Thr Leu Gln Asp Glu Lys
            915                 920                 925

Thr Ile Lys Leu Asn Ser Val His Leu Asp Glu Ser Gly Val Ala Glu
930                 935                 940

Ile Leu Lys Phe Met Asn Arg Lys Gly Asn Thr Asn Thr Ser Asp Ser
945                 950                 955                 960
```

-continued

```
Leu Met Ser Phe Leu Glu Ser Met Asn Ile Lys Ser Ile Phe Val Asn
                965                 970                 975
Phe Leu Gln Ser Asn Ile Lys Phe Ile Leu Asp Ala Asn Phe Ile Ile
            980                 985                 990
Ser Gly Thr Thr Ser Ile Gly Gln Phe Glu Phe Ile Cys Asp Glu Asn
        995                 1000                1005
Asp Asn Ile Gln Pro Tyr Phe Ile Lys Phe Asn Thr Leu Glu Thr
    1010                1015                1020
Asn Tyr Thr Leu Tyr Val Gly Asn Arg Gln Asn Met Ile Val Glu
    1025                1030                1035
Pro Asn Tyr Asp Leu Asp Asp Ser Gly Asp Ile Ser Ser Thr Val
    1040                1045                1050
Ile Asn Phe Ser Gln Lys Tyr Leu Tyr Gly Ile Asp Ser Cys Val
    1055                1060                1065
Asn Lys Val Val Ile Ser Pro Asn Ile Tyr Thr Asp Glu Ile Asn
    1070                1075                1080
Ile Thr Pro Val Tyr Glu Thr Asn Asn Thr Tyr Pro Glu Val Ile
    1085                1090                1095
Val Leu Asp Ala Asn Tyr Ile Asn Glu Lys Ile Asn Val Asn Ile
    1100                1105                1110
Asn Asp Leu Ser Ile Arg Tyr Val Trp Ser Asn Asp Gly Asn Asp
    1115                1120                1125
Phe Ile Leu Met Ser Thr Ser Glu Glu Asn Lys Val Ser Gln Val
    1130                1135                1140
Lys Ile Arg Phe Val Asn Val Phe Lys Asp Lys Thr Leu Ala Asn
    1145                1150                1155
Lys Leu Ser Phe Asn Phe Ser Asp Lys Gln Asp Val Pro Val Ser
    1160                1165                1170
Glu Ile Ile Leu Ser Phe Thr Pro Ser Tyr Tyr Glu Asp Gly Leu
    1175                1180                1185
Ile Gly Tyr Asp Leu Gly Leu Val Ser Leu Tyr Asn Glu Lys Phe
    1190                1195                1200
Tyr Ile Asn Asn Phe Gly Met Met Val Ser Gly Leu Ile Tyr Ile
    1205                1210                1215
Asn Asp Ser Leu Tyr Tyr Phe Lys Pro Pro Val Asn Asn Leu Lys
    1220                1225                1230
Gly Gly Arg Ala Asp Pro Ala Phe Leu Tyr Lys Val Val Ser Ala
    1235                1240                1245
Trp Ser His Pro Gln Phe Glu Lys
    1250                1255
```

The invention claimed is:

1. A polypeptide, comprising an amino acid sequence having at least 80% sequence identity with an amino acid sequence consisting of residues 1400-1800 of a *Clostridium difficile* (*C. difficile*) Toxin B sequence corresponding to SEQ ID NO:2 or SEQ ID NO:4;

with the proviso that the polypeptide does not include one or more of the Repeat Units (RU) located between amino acid residues 1853-2366 of said *C. difficile* Toxin B sequence.

2. The polypeptide according to claim 1, wherein said polypeptide does not include the amino acid sequence provided by amino acid residues 1853-2366 of said *C. difficile* Toxin B sequence.

3. The polypeptide according to claim 1, wherein the polypeptide comprises an amino acid sequence having at least 80% sequence identity with an amino acid sequence consisting of residues 1145-1852, residues 767-1852, or residues 543-1852 of said *C. difficile* Toxin B sequence.

4. The polypeptide according to claim 1, wherein said polypeptide further comprises a second amino acid sequence; wherein said second amino acid sequence is the amino acid sequence of one or more of a bacterial surface layer protein, NusA, thioredoxin, maltose-binding protein, or an ubiquitin-like peptide, or a fragment of any of said second amino acid sequences.

5. The polypeptide according to claim 4, wherein the second amino acid sequence comprises the amino acid sequence of a *C. difficile* surface layer protein.

6. The polypeptide according to claim 5, wherein the amino acid sequence of the *C. difficile* surface layer protein comprises an amino acid sequence that has at least 80% sequence identity with amino acid residues 27-401 of the CD2767 peptide of SEQ ID NO:16.

7. A method of inducing an immune response in a subject, said method comprising administering an effective amount of a polypeptide according to claim 1.

8. A method of inducing an immune response in a subject, said method comprising administering an effective amount of a polypeptide according to claim 2.

9. A method of inducing an immune response in a subject, said method comprising administering an effective amount of a polypeptide according to claim 3.

10. A method of inducing an immune response in a subject, said method comprising administering an effective amount of a polypeptide according to claim 4.

11. A method of inducing an immune response in a subject, said method comprising administering an effective amount of a polypeptide according to claim 5.

12. A method of inducing an immune response in a subject, said method comprising administering an effective amount of a polypeptide according to claim 6.

* * * * *